(12) United States Patent
Roose et al.

(10) Patent No.: US 10,676,792 B2
(45) Date of Patent: Jun. 9, 2020

(54) PROGNOSTIC AND DIAGNOSTIC METHODS FOR COLORECTAL CANCER

(71) Applicant: The Regents of the University of California, Oakland, CA (US)

(72) Inventors: Jeroen Roose, Mill Valley, CA (US); Philippe Depeille, San Francisco, CA (US); Robert Warren, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/563,493

(22) PCT Filed: Mar. 31, 2016

(86) PCT No.: PCT/US2016/025334
§ 371 (c)(1),
(2) Date: Sep. 29, 2017

(87) PCT Pub. No.: WO2016/161153
PCT Pub. Date: Oct. 6, 2016

(65) Prior Publication Data
US 2019/0119755 A1    Apr. 25, 2019

Related U.S. Application Data

(60) Provisional application No. 62/141,537, filed on Apr. 1, 2015.

(51) Int. Cl.
*C12Q 1/6886* (2018.01)
*G01N 33/574* (2006.01)
*G16B 25/00* (2019.01)

(52) U.S. Cl.
CPC ..... *C12Q 1/6886* (2013.01); *G01N 33/57419* (2013.01); *G01N 33/57484* (2013.01); *G16B 25/00* (2019.02); *C12Q 2600/106* (2013.01); *C12Q 2600/118* (2013.01); *C12Q 2600/156* (2013.01); *C12Q 2600/158* (2013.01); *G01N 2800/52* (2013.01); *Y02A 90/26* (2018.01)

(58) Field of Classification Search
CPC .......... G01N 33/574; G01N 33/57407; G01N 33/57415; G01N 33/57423; G01N 33/57438
See application file for complete search history.

(56) References Cited

U.S. PATENT DOCUMENTS

| | | | |
|---|---|---|---|
| 2006/0281122 A1* | 12/2006 | Bryant | C12Q 1/6886 435/6.16 |
| 2009/0023149 A1 | 1/2009 | Knudsen | |
| 2011/0251087 A1* | 10/2011 | Glinsky | C12Q 1/6886 506/9 |
| 2013/0316921 A1 | 11/2013 | Cohen et al. | |
| 2014/0018405 A1 | 1/2014 | Zahn et al. | |

FOREIGN PATENT DOCUMENTS

WO    2014/145181 A1    9/2014

OTHER PUBLICATIONS

Manna et al. (J. Immunology 2013 191:2837-2846) (Year: 2013).*
Normanno et al. (Nature Review Clinical Oncology Sep. 2009 6: 519-527) (Year: 2009).*
Depeille et al., Abstract LB-206: The Ras exchange factor RasGRP1 opposes proliferative EGFR-SOS1 Ras signals and restricts intestinal epithelial cell growth, Cancer Research, Oct. 2014, vol. 74, Abstract.
PCT/US16/25334, International Search Report and Written Opinion, dated Sep. 20, 2016, pp. 1-14.

* cited by examiner

*Primary Examiner* — Peter J Reddig
(74) *Attorney, Agent, or Firm* — Kilpatrick Townsend & Stockton LLP

(57) ABSTRACT

Provided herein are methods for selecting a drug therapy for a patient with cancer, such as colorectal cancer, pancreatic cancer, lung cancer or breast cancer. The method includes determining or measuring the level of RasGRP1 polynucleotide or polypeptide in a sample from the patient. Also provided herein are methods for determining the likelihood of a good prognosis for a patient with cancer. Additionally, provided herein are methods for predicting the likelihood of a negative clinical response to an anti-EGFR therapy in a subject with cancer.

21 Claims, 30 Drawing Sheets
Specification includes a Sequence Listing.

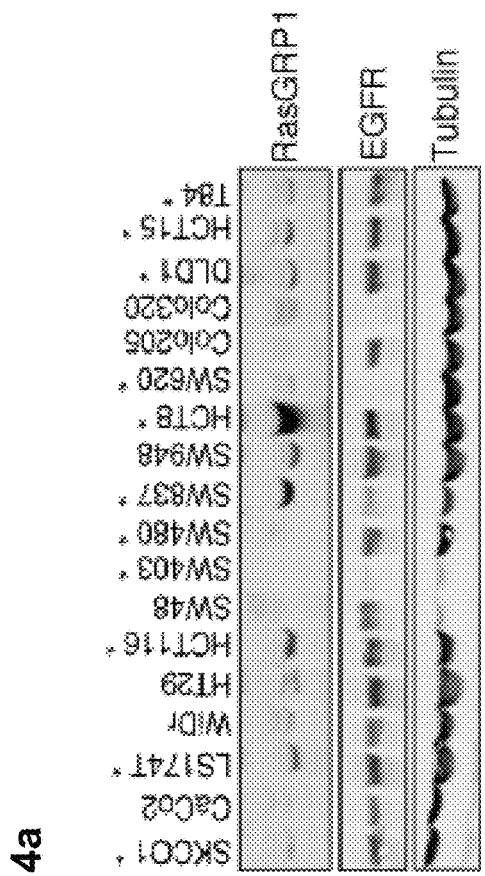
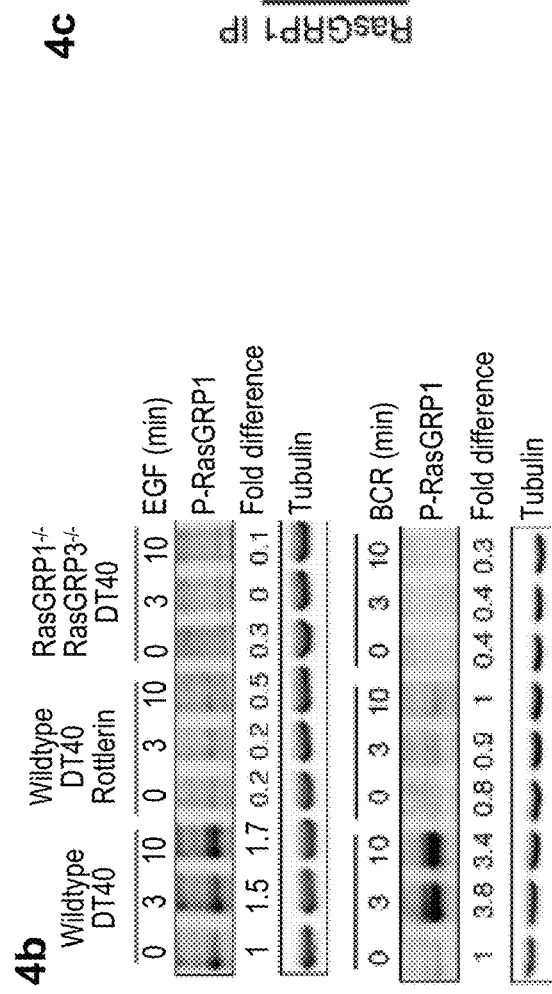
FIGS. 4a-4c

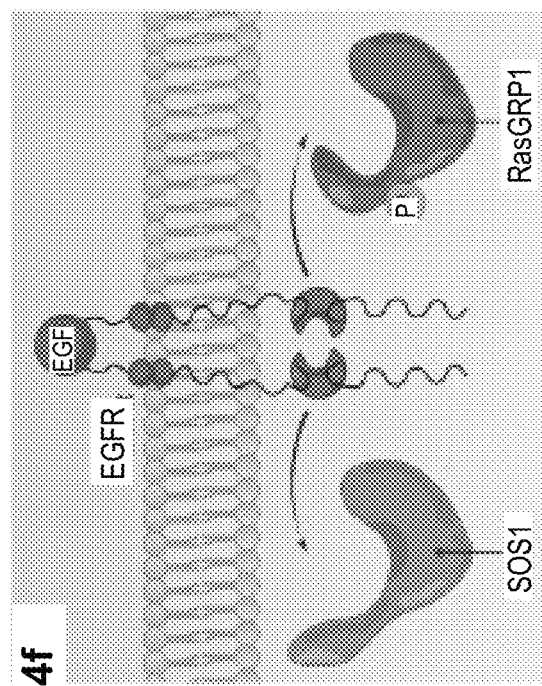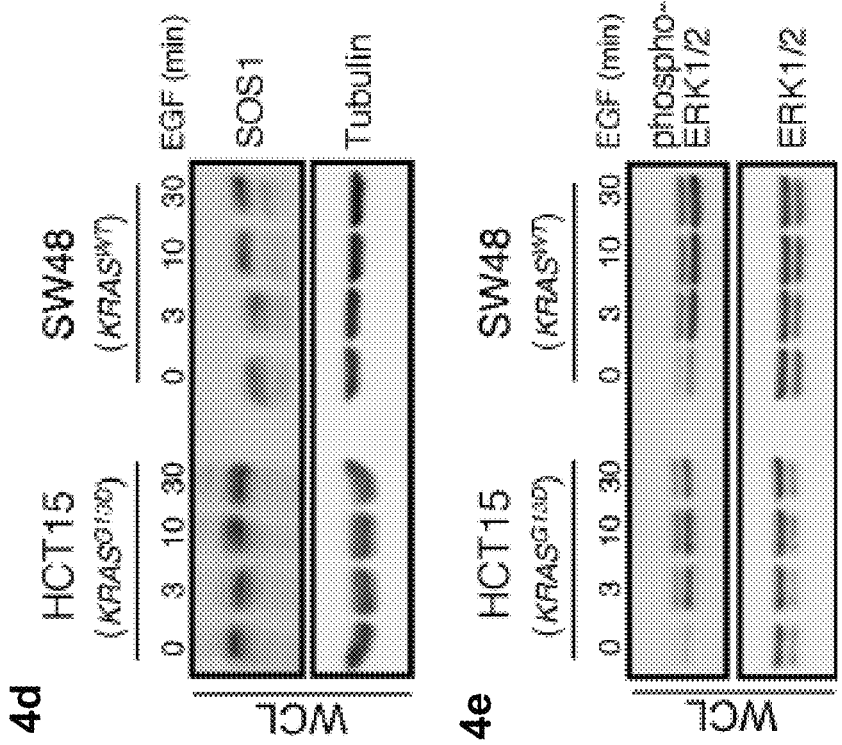
FIGS. 4d-4f

5a

5b

5c

11a

11b

15a

15b

PROGNOSTIC AND DIAGNOSTIC METHODS FOR COLORECTAL CANCER

CROSS-REFERENCES TO RELATED APPLICATIONS

The present application is a 35 U.S.C. § 371 U.S. National Phase of PCT/US2016/025334, filed Mar. 31, 2016, which claims benefit of priority to U.S. Provisional Patent Application No. 62/141,537, filed Apr. 1, 2015, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under grants no. U54 CA143874 and P01 AI091580 awarded by the National Institutes of Health. The Government has certain rights in the invention.

REFERENCE TO SUBMISSION OF A SEQUENCE LISTING AS A TEXT FILE

The Sequence Listing written in file 1005552_ST25.txt created on Sep. 29, 2017, 4,173 bytes, machine format IBM-PC, MS-Windows operating system, is hereby incorporated by reference in its entirety for all purposes.

BACKGROUND OF THE INVENTION

Colorectal cancer (CRC) causes 655,000 deaths worldwide per year and is the third most common cancer in the United States. Patients with late-stage CRC have limited treatment options and molecular therapies are highly desired. The epidermal growth factor receptor (EGFR) plays a growth-promoting role in many types of cancer. Inhibition of EGFR signals by EGFR blocking antibodies and by EGFR kinase inhibitors is a successful molecular therapy for lung cancer patients. Despite widespread expression of EGFR in CRC, clinical trials with anti-EGFR therapy have been largely disappointing for CRC. Patients with mutations in KRAS have not responded well in these trials. Moreover, stratification of CRC patients based on the presence or absence of KRAS mutations has not been an effective or sensitive prognostic or predictive method.

In clinical trials of panitumumab (Vectibix®) and cetuximab (Erbitux®), patients with $KRAS^{mut}$ tumors did not benefit from these drugs. However, other studies have shown that a subpopulation of CRC patients with $KRAS^{mut}$ tumors do respond to anti-EGFR therapies. Thus, $KRAS^{wt}$ and $KRAS^{mut}$ status alone are not effective indicators of anti-EGFR response.

BRIEF SUMMARY OF ASPECTS THE INVENTION

In one aspect, provided herein is a method for selecting a drug therapy for a subject with cancer, e.g., colorectal cancer, pancreatic cancer, lung cancer or breast cancer. The method includes (a) determining the level of RasGRP1 in a sample obtained from the subject; and (b) selecting a non anti-EGFR therapy for the subject if the level of RasGRP1 is higher than a threshold value. The sample from the subject can be a tumor biopsy sample, a circulating tumor cell, or a fine needle aspirate. The level of RasGRP1 can be the level, amount or concentration of RasGRP1 polynucleotide or the level, amount or concentration of RasGRP1 polypeptide in the sample. In some embodiments, the level of RasGRP1 polynucleotide is determined using an amplification assay or a hybridization assay. In some instances, the amplification assay is a probe-based quantitative amplification assay, such as a TaqMan® assay. In some embodiments, the level of RasGRP1 polypeptide is determined using an immunoassay, immunohistochemistry, western blot or mass spectrometry. The method can also include determining the presence or absence of a KRAS mutation in an equivalent sample obtained from the subject, wherein the KRAS mutation is G12C, G12R, G12S, G12A, G12D, G12V, G13C, G13R, G13S, G13A, G13D, G13V, G34T, G34A, G34C, G35T, G35C, G35A, G37T, G37C, G37A, G48T, G38A, G38A, Q61K, Q61L, Q61R, Q61H, K117N, A146P, A146T or A146V.

In some embodiments, the method can also include administering an effective amount of the non anti-EGFR therapy to the subject to alleviate at least one symptom of the cancer. The non anti-EGFR therapy can be a BRAF inhibitor, IGFR inhibitor, MEK inhibitor, PI3K inhibitor, VEGR inhibitor or other kinase inhibitor.

In second aspect, provided herein is a method for predicting a likelihood of a good prognosis for a subject with cancer, such as colorectal cancer, pancreatic cancer, lung cancer or breast cancer. The method includes (a) determining the level of RasGRP1 in a sample obtained from the subject; and (b) predicting a likelihood of a good prognosis for the subject if the level of RasGRP1 is higher than a threshold value. A good prognosis includes overall survival, progression-free survival, or response to therapy. If the level of RasGRP1 is lower than a threshold value, a likelihood of a poor prognosis for the subject is predicted. The method can also include determining the presence or absence of a KRAS mutation in an equivalent sample obtained from the subject, wherein the KRAS mutation is G12C, G12R, G12S, G12A, G12D, G12V, G13C, G13R, G13S, G13A, G13D, G13V, G34T, G34A, G34C, G35T, G35C, G35A, G37T, G37C, G37A, G48T, G38A, G38A, Q61K, Q61L, Q61R, Q61H, K117N, A146P, A146T or A146V. Additionally, the method can include predicting that the subject will not respond to an anti-EGFR therapy. If it is determined that the subject is a non-responder to an anti-EGFR therapy, a non anti-EGFR therapy can be recommended or administered to the subject.

The sample obtained from the subject can be such as a tumor biopsy sample, a circulating tumor cell, or a fine needle aspirate. The level of RasGRP1 can be the level, amount or concentration of RasGRP1 polynucleotide or the level, amount or concentration of RasGRP1 polypeptide in the sample. In some embodiments, the level of RasGRP1 polynucleotide is determined using an amplification assay or a hybridization assay. In some instances, the amplification assay is a probe-based quantitative polymerase chain reaction assay, such as a TaqMan® assay. In some embodiments, the level of RasGRP1 polypeptide is determined using an immunoassay, immunohistochemistry, western blot or mass spectrometry.

In third aspect, provided herein is a method for predicting a likelihood of a negative clinical response to an anti-EGFR therapy in a subject with cancer, such as colorectal cancer, pancreatic cancer, lung cancer or breast cancer. The method includes (a) d determining the level of RasGRP1 in a sample obtained from the subject, such as a tumor biopsy sample, a circulating tumor cell, and a fine needle aspirate, and (b) predicting a likelihood of a negative clinical response to the anti-EGFR therapy if the level of RasGRP1 is higher than a control value. The method can also include determining the presence or absence of a KRAS mutation in an equivalent sample obtained from the subject, wherein the KRAS mutation is G12C, G12R, G12S, G12A, G12D, G12V, G13C, G13R, G13S, G13A, G13D, G13V, G34T, G34A, G34C, G35T, G35C, G35A, G37T, G37C, G37A, G48T, G38A, G38A, Q61K, Q61L, Q61R, Q61H, K117N, A146P, A146T, A146V or a combination thereof. The level of RasGRP1 can be the level, amount or concentration of RasGRP1 polynucleotide or the level, amount or concentration of RasGRP1 polypeptide in the sample. In some embodiments, the level of RasGRP1 polynucleotide is determined using an amplification assay or a hybridization assay. In some instances, the amplification assay is a probe-based quantitative polymerase chain reaction assay, such as a TaqMan® assay. In some embodiments, the level of RasGRP1 polypeptide is determined using an immunoassay, immunohistochemistry, western blot or mass spectrometry.

The method can also include administering an effective amount of the non anti-EGFR therapy to the subject to alleviate at least one symptom of the cancer. In some instances, the non anti-EGFR therapy includes a BRAF inhibitor, AKT inhibitor, MEK inhibitor, cMET inhibitor, VEGR inhibitor or other kinase inhibitor.

Optionally, the method can include predicting a likelihood of a positive clinical response to the anti-EGFR therapy in the subject if the level of RasGRP1 is lower than a threshold value. As such, the method can also comprise recommending or administering an anti-EGFR therapy to the subject. In some cases, the he anti-EGFR therapy is an EGFR blocking antibody or an EGFR inhibitor drug.

BRIEF DESCRIPTION OF THE DRAWINGS

FIGS. 1a and 1b are representative results of 3 or more independent experiments. Plots showing RasGRP1 mRNA expression z-scores versus copy number value in NCI-60 Cell Lines were obtained via cBio Portal (FIG. 1c). Each blue dot represents one cell line. Some colorectal cancer cell lines and leukemia cell lines were noted as reference. Plots showing RasGRP1 mRNA expression z-scores versus copy number value in 56 colorectal cancer cell lines (FIG. 1d). Various colorectal cancer cell lines used in our study were noted on the plot. RasGRP1 mRNA expression z-scores versus copy number value in human colon cancer patients (n=276) from TCGA (The Cancer Genome Atlas) Colorectal Adenocarcinoma dataset (FIG. 1e). Each dot represents a sample with either, no mutation on RasGRP1 (blue), missense mutation (red, n=5) or nonsense (yellow). RasGRP1 mRNA expression z-scores are plotted against KRAS mRNA expression z-scores for the 276 patient samples in FIG. 1e (FIG. 1f). Colors represent mutational status. RasGRP1 mRNA expression determined by Taqman PCR on liver metastases samples surgically removed from 30 colorectal cancer patients (FIG. 1g). Oncomine analysis was performed to examine RASGRP1 expression in human colon adenocarcinoma (n=101) (dark blue boxplot) and normal colon (n=19) (light blue boxplot) using online TCGA microarray data (FIG. 1h). RASGRP1 levels are decreased in colon adenocarcinoma compared with normal tissues (p=6.73E-10, fold change=−2.244).

(FIG. 2l) Two mice per genotype and fifty villi per mouse were counted and averages±s.e.m are depicted. ***p<0.001 (t-test).

FIGS. 3a-3h show that loss of one or two Rasgrp1 alleles exacerbates serrated dysplasia of KRasG12D epithelium. Representative sections of colon with H&E (FIG. 3a) or Ki67 stainings (FIG. 3b), revealing the serrated dysplasia of the colonic epithelium in KRas$^{G12D}$ mice that is further exacerbated with loss of Rasgrp1. Scale bars, 50 μm. Quantification of diving cells in crypts regions of the colon following a short-term (2 hr.) in vivo BrdU labeling assay (FIG. 3c). Five mice per genotype and fifty crypts per mouse were counted and averages±s.e.m are depicted. *p<0.05, ***p<0.0001. Representative images of colonic section with Alcian blue staining to reveal goblet cells (FIG. 3d). Quantification and statistical analysis of the frequency of goblet cells in the distal colon (FIG. 3e). Three mice per genotype and fifty open crypts per mouse were counted and averages±s.e.m are depicted. *p<0.05, p<0.001. Representative H&E-stained sections of small intestine demonstrating the branched villi in KRas$^{G12D}$ and KRas$^{G12D}$:Rasgrp1$^{-/-}$ mice (FIGS. 3f-3h). Scale bars, 50 μm. Quantification of branching villi in the small intestine following the approach of FIG. 2C (FIG. 3i). *p<0.0001. Higher magnifications of branching villi (FIGS. 3j-3l) with Ki67 stainings (FIGS. 3n-3p). Detail of the aberrant transit-amplifying (T/A) zone in KRas$^{G12D}$:Rasgrp1$^{-/-}$ small intestine (from FIGS. 3l and 3p) (FIGS. 3m and 3q). All mice were euthanized at 6 months of age.

FIGS. 4a-4f show that EGFR connects to both RasGRP1 and SOS1. Detection of RasGRP1- and EGFR-expression by western blot in eighteen colorectal cancer (CRC) cell lines. Asterisks indicate KRAS mutations (KRASMUT) (FIG. 4a). RasGRP1 phosphorylation in EGF- or BCR-stimulated DT40 B cells (FIG. 4b). PKC inhibitor (Rottlerin) and genetic deletion of RasGRP1/3 function as specificity controls and Tubulin as protein loading control. Detection of RasGRP1 phosphorylation in EGF-stimulated HCT15 and SW48 CRC cells from which RasGRP1 protein was immunoprecipitated (IP) (FIG. 4c). Blotting for total RasGRP1 levels reveals equal efficiency of the IP and Tubulin expression of whole cell lysates (WCL) demonstrates equal protein input for the IP. Detection of EGF-induced SOS1 mobility shifts and ERK phosphorylation in WCL of HCT15 and SW48 cells (FIGS. 4d and 4e). All panels are representative results of three or more independent experiments. Cartoon of EGFR-RasGRP1 and EGFR-SOS1 signalling (FIG. 4f).

FIGS. 6c-e represent averages with standard errors; ns=not significant, *p<0.05, ***p<0.0001.

FIG. 8j is representative result of three independent experiments. P-ERK in Apc$^{Min/+}$ mice was arbitrarily set at 1.0.

FIG. 9c provides a comparison between Ki67-positive cells/crypt for each genotype.

10c quantification of villi length for the different mouse genotypes. FIG. 10d shows the length of the intestinal track from the different mouse genotypes.

FIG. 13a shows the pull-down assays. Quantification of the assays for NRAS-GTP is shown in FIGS. 13b and 13c for different cell lines. Quantification of the assays for HRAS-GTP is shown in FIGS. 13d and 13e for different cell lines.

FIGS. 14a and 14b represent two independent experiments.

FIG. 16c shows cross sections of colonic tumors from $Apc^{Min/+}$ and $Apc^{Min/+}$:Rasgrp1$^{-/-}$ mice. FIG. 16d shows Ki67-staining of colonic tumors from $Apc^{Min/+}$ and $Apc^{Min/+}$:Rasgrp1$^{-/-}$ mice. FIG. 16e provides quantification of Ki67-positive cells. FIG. 16f shows phospho-ERK staining of colonic tumors in the mice. FIG. 16g shows that colonic tumors in $Apc^{Min/+}$:Rasgrp1$^{-/-}$ mice contain more BrdU positive cells compared to $Apc^{Min/+}$ mice. $Apc^{Min/+}$:Rasgrp1$^{-/-}$ mice have higher levels of pERK in normal crypt (FIG. 16h) and colonic tumors (FIG. 16i), compared to $Apc^{Min/+}$ mice. FIG. 16j shows cleaved caspase-3 staining in $Apc^{Min/+}$ and $Apc^{Min/+}$:Rasgrp1$^{-/-}$ tumors. FIG. 16k shows the quantification of data from FIG. 16j.

DETAILED DESCRIPTION OF THE INVENTION

I. Introduction

Figures 1A, 1B:
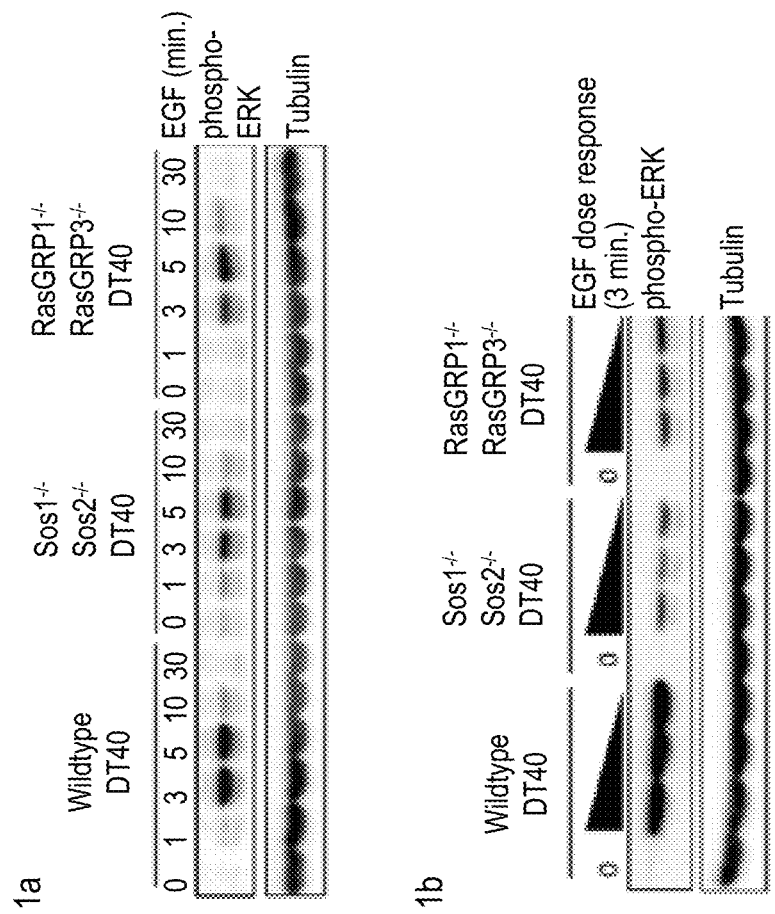
FIGS. 1a-1e show that RasGRP1 is expressed in CRC cell lines and CRC patient tumor samples. Time course of EGF-induced ERK phosphorylation in DT40 B cells that are wild type or genetically deleted for SOS1 and SOS2, or for RasGRP1 and RasGRP3 (FIG. 1a). EGF dose is 10 ng/ml. Tubulin serves as protein loading control. As in FIG. 1a, now analyzing the effects of 25, 5, and 1 ng/ml EGF in a 3-minute stimulation (FIG. 1b).

The present disclosure provides, in part, methods for detecting the level of the Ras activator RasGRP1 in tumor cells (e.g., circulating cells, fine needle aspirates, or tissue biopsies) from a patient with cancer (e.g., colorectal cancer, pancreatic cancer, lung cancer or breast cancer). The presence or level of RasGRP1 polynucleotide (mRNA) or polypeptide can be used for therapy selection, predicting drug response, and cancer prognosis. The methods are useful for determining whether a cancer patient is likely to have a good prognosis. The presence or level of RasGRP1 in a patient's sample can also be used as an indicator whether a patient will not respond to an anti-EGFR therapy, such as an anti-EGFR antibody or an EGFR inhibitor drug.

II. Definitions

The term "colorectal cancer" is used in the broadest sense and refers to (1) all stages and all forms of cancer arising from epithelial cells of the large intestine and/or rectum and/or (2) all stages and all forms of cancer affecting the lining of the large intestine and/or rectum. In the staging systems used for classification of colorectal cancer, the colon and rectum are treated as one organ.

The term "epidermal growth factor receptor" ("EGFR") refers to a gene that encodes a membrane polypeptide that binds, and is thereby activated by, epidermal growth factor (EGF). EGFR is also known in the literature as ERBB, ERBB1 and HER1. An exemplary EGFR is the human epidermal growth factor receptor (see Ullrich et al. (1984) Nature 309:418-425; Genbank accession number NP_005219.2; complete cds AY588246.1). Binding of an EGF ligand activates the EGFR (e.g. resulting in activation of intracellular mitogenic signaling, autophosphorylation of EGFR). One of skill in the art will appreciate that other ligands, in addition to EGF, can bind to and activate the EGFR. Examples of such ligands include, but are not limited to, amphiregulin, epiregulin, TGF-α, betacellulin, and heparin-binding EGF (HB-EGF). Intracellular domain of, a human, EGFR comprises a polypeptide sequence from amino acid adjacent to the transmembrane domain up to COOH-terminus of the EGFR. Intracellular domain comprises, inter alia, tyrosine kinase domain.

"Anti-EGFR therapy" or "anti-EGFR drug" refers to any therapeutic agent, molecule, or compound capable of directly or indirectly inhibiting activation of EGFR. An anti-EGFR therapy include agents that bind to an EGFR molecule and inhibit its activation. Anti-EGFR therapy includes antibodies that bind to an EGFR and inhibit activation of the EGFR; as well as small molecule tyrosine kinase inhibitors or "kinase inhibitors" that inhibit activation of an EGFR. Antibodies to EGFR include IgG; IgM; IgA; antibody fragments that retain EGFR binding capability, e.g., Fv, Fab, F(ab)$_2$, single-chain antibodies, and the like; chimeric antibodies; etc. Small molecule tyrosine kinase inhibitors of EGFR include EGFR-selective tyrosine kinase inhibitors. Small molecule tyrosine kinase inhibitors of EGFR can have a molecular weight in a range of from about 50 Da to about 10,000 Da.

The term "non anti-EGFR therapy" refers to any therapeutic agent, molecule, or compound that does not directly bind to EGFR (e.g., EGFR polynucleotide or EGFR polypeptide) or directly inhibit EGFR activation, and does directly bind to a different kinase or inhibit its activity. For instance, a non anti-EGFR therapy can be an anti-BRAF therapy, anti-AKT therapy, anti-MEK therapy, anti-cMET therapy, anti-VEGR therapy, other anti-receptor tyrosine kinase therapy, or other anti-kinase therapy.

The term "RasGRP1" refers to the RasGFP1 gene identified as NCBI GeneID No. 10125 and/or its expression products, including the RasGFP1 coding sequence or mRNA (Genbank Accession No. NM_001128602) and the RasGFP1 polypeptide (GenBank Accession No. NP_001122074).

The term "KRAS" refers to the KRAS gene identified as NCBI GenBank Accession No. NM_004985.3, and/or its expression products. "KRAS" is also identified in literature as KRAS1, KRAS2, RASK2, KI-RAS, K-RAS4A, K-RAS4B or p21.

As used herein, the term "amino acid variant" is used to refer to an amino acid change to a reference human protein sequence resulting from genetic variants or nucleotide variants to the reference human gene encoding the reference protein. The term "amino acid variant" is intended to encompass not only single amino acid substitutions, but also amino acid deletions, insertions, and other significant changes of amino acid sequence in the reference protein.

The term "EGFR inhibitor" refers to a compound that inhibits, decreases, lowers, or reduces at least one activity of an epidermal growth factor receptor (EGFR). Examples of EGFR inhibitors include, but are not limited to, [6,7-bis(2-methoxyethoxy)-4-quinazolin-4-yl]-(3-ethynylphenyl) amine (also known as OSI-774), erlotinib, CI-1033 (formerly known as PD183805), AG-1478, CGP-59326, PKI-166, EKB-569, lapatinib or lapatinib ditosylate; and gefitinib, AG490 (a tyrphostin), ARRY-334543, BIBW-2992, EKB-569, ZD6474, BMS-599626 (Bristol-Myers Squibb), cetuximab, and MDX-447.

The term "high level" as used herein with respect to the level of RasGRP1 polynucleotide or polypeptide level refers to any level that is above a threshold value that is established from the level of RasGRP1 polynucleotide or polypeptide in a sample from a reference (control) population. In some embodiments, the reference population is one or more CRC patients receiving an anti-EGFR therapy. In some instances, this reference population includes one or more CRC patients receiving an anti-EGFR therapy in combination with another molecular therapy, e.g., aVEGR inhibitor, BRAF inhibitor, MEK inhibitor, etc., chemotherapy, radiotherapy or surgery. In yet other embodiments, the reference population is one or more CRC patients that are not receiving therapy. In some embodiments, the reference population is one or more normal individual. In some cases, elevated polynucleotide (e.g., mRNA) levels of RasGRP1 can be 0.5, 1, 2, 3, 4, 5, 6, 7, 8, 9, 10 or more fold greater than the threshold level of RasGRP1 RNA detected in a sample from one or more CRC patients a CRC patient on an anti-EGFR therapy or from a plurality of CRC patients on an anti-EGFR therapy an anti-EGFR therapy. Elevated polypeptide levels of RasGRP1 can be 0.5, 1, 2, 3, 4, 5, 6, 7, 8, 9, 10 or more fold greater than the threshold level of RasGRP1 polypeptide detected in a sample from one or more CRC patients receiving an anti-EGFR therapy.

The term "low level" as used herein with respect to the level of RasGRP1 polynucleotide or polypeptide level refers to any level that is below a threshold value that is established from the level of RasGRP1 polynucleotide or polypeptide in a sample from a reference (control population). In some embodiments, the reference population is one or more CRC patients receiving an anti-EGFR therapy. In some instances, this reference population includes one or more CRC patients receiving an anti-EGFR therapy in combination with another molecular therapy, e.g., aVEGR inhibitor, BRAF inhibitor, MEK inhibitor, etc., chemotherapy, radiotherapy or surgery. In yet other embodiments, the reference population is one or more CRC patients that are not receiving therapy. In some embodiments, the reference population is one or more normal individual. In some cases, decreased polynucleotide (e.g., mRNA) levels of RasGRP1 can be 0.5, 1, 2, 3, 4, 5, 6, 7, 8, 9, 10 or more fold lower than the threshold level of RasGRP1 RNA detected in a sample from one or more CRC patients receiving an anti-EGFR therapy. Decreased polypeptide levels of RasGRP1 can be 0.5, 1, 2, 3, 4, 5, 6, 7, 8, 9, 10 or more fold lower than the threshold level of RasGRP1 polypeptide detected in a sample from one or more CRC patients receiving an anti-EGFR therapy.

The terms "responsive," "clinical response," "positive clinical response," and the like, as used in the context of a patient's response to an anticancer therapy, are used interchangeably and refer to a favorable patient response to a drug as opposed to unfavorable responses, i.e. adverse events. In a patient, beneficial response can be expressed in terms of a number of clinical parameters, including loss of detectable tumor (complete response, CR), decrease in tumor size and/or cancer cell number (partial response, PR), tumor growth arrest (stable disease, SD), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment. Continued increase in tumor size and/or cancer cell number and/or tumor metastasis is indicative of lack of beneficial response to treatment. In a population the clinical benefit of a drug, i.e., its efficacy can be evaluated on the basis of one or more endpoints. For example, analysis of overall response rate (ORR) classifies as responders those patients who experience CR or PR after treatment with drug. Analysis of disease control (DC) classifies as responders those patients who experience CR, PR or SD after treatment with drug.

A positive clinical response can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition of metastasis; (6) enhancement of anti-tumor immune response, possibly resulting in regression or rejection of the tumor; (7) relief, to some extent, of one or more symptoms associated with the tumor; (8) increase in the length of survival following treatment; and/or (9) decreased mortality at a given point of time following treatment. Positive clinical response may also be expressed in terms of various measures of clinical outcome. Positive clinical outcome can also be considered in the context of an individual's outcome relative to an outcome of a population of patients having a comparable clinical diagnosis, and can be assessed using various endpoints such as an increase in the duration of recurrence-free interval (RFI), an increase in the time of survival as compared to overall survival (OS) in a population, an increase in the time of disease-free survival (DFS), an increase in the duration of distant recurrence-free interval (DRFI), and the like. An increase in the likelihood of positive clinical response corresponds to a decrease in the likelihood of cancer recurrence.

The term "good prognosis" refers to the prediction of the likelihood of disease-specific survival, overall survival or disease free survival, including partial remission, complete remission, and suppression of cancer cell proliferation and/or metastasis. A good prognosis for a patient with a solid tumor cancer includes a positive response rate in terms of disease remission or tumor shrinkage, or any other form of evaluating reduced tumor burden or growth. A good prognosis can be measured as the length (time) of survival.

The term "poor prognosis" refers to the prediction of the likelihood of cancer-attributable death or progression, including recurrence, relapse, metastatic spread, and drug resistance.

The term "overall survival" refers to the time interval from either the time of diagnosis or the start of treatment that the patient is still alive.

The term "progression-free survival" refers to the time interval from treatment of the patient until the progression of cancer or death of the patient, whichever occurs first.

The term "responder" or "responsive" refers to a patient who has cancer, and who exhibits a beneficial clinical response following treatment with an anti-cancer therapy.

The term "non-responder" or "non-responsive" refers to a patient who has a cancer, and who does not exhibit a beneficial clinical response following treatment with an anti-cancer The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "inhibitor" in the context of a specific polynucleotide or polypeptide, refers to inhibitory molecules identified using in vitro and/or in vivo assays for binding or signaling of the specific polynucleotide or polypeptide, e.g., naturally-occurring ligands and synthetically-designed ligands, antibodies and antibody fragments, antagonists, agonists, small molecules including carbohydrate-containing molecules, siRNAs, RNA aptamers, homologs thereof, mimetics thereof, and the like. In some cases, the inhibitor directly or indirectly binds to the specific polypeptide, such as a neutralizing antibody or blocking antibody. Inhibitors, as used herein, are synonymous with inactivators and antagonists.

A. Detecting RasGRP1 Levels

The methods provided herein are based on the determination of the level of RasGRP1 in a biological sample. As used herein, the term "RasGRP1" includes a nucleotide sequence of a RasGRP1 gene containing one or more changes as compared to the wild-type RasGRP1 gene or an amino acid sequence of a RasGRP1 polypeptide containing one or more changes as compared to the wild-type RasGRP1 polypeptide sequence. Human RasGRP1 is set forth in NCBI GeneID No. 10125. The mRNA (coding) and polypeptide sequences of human RasGRP1 are set forth in, e.g., Genbank Accession Nos. NM_001128602 and NP_001122074, respectively. In addition, the complete sequence of human chromosome 15 assembly GRCh38, which includes RasGRP1, is set forth in, e.g., Genbank Accession No. NC_000015.10. Furthermore, the sequence of RasGRP1 from other species can be found in the GenBank database.

The levels of RasGRP1 polynucleotide (e.g., mRNA) can be detected using techniques known to those of ordinary skill in the art, such as polymerase chain reaction (PCR) and hybridization assays.

Probes may be used in hybridization techniques to detect polynucleotides. The technique generally involves contacting and incubating nucleic acids obtained from a sample from a patient with a probe under conditions favorable for the specific annealing of the probes to complementary sequences in the nucleic acids (e.g. under stringent conditions). After incubation, the non-annealed nucleic acids are removed, and the presence of nucleic acids that have hybridized to the probe if any are detected. Nucleotide probes for use in the detection of polynucleotide sequences in samples may be constructed using conventional methods known in the art. The probes may comprise DNA or DNA mimics corresponding to a portion of an organism's genome, or complementary RNA or RNA mimics. The nucleic acids can be modified at the base moiety, at the sugar moiety, or at the phosphate backbone. DNA can be obtained using standard methods such as PCR amplification of genomic DNA or cloned sequences. Computer programs known in the art can be used to design primers with the required specificity and optimal amplification properties. A nucleotide probe may be labeled with a detectable substance such as a radioactive label which provides for an adequate signal and has sufficient half-life. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleic acids to be detected and the amount of nucleic acids available for hybridization.

The detection of polynucleotides in a sample may involve the amplification of specific gene sequences using an amplification method such as PCR, followed by the analysis of the amplified molecules using techniques known to those skilled in the art. By way of example, oligonucleotide primers may be employed in a PCR based assay to amplify a portion of a polynucleotide and to amplify a portion of a polynucleotide derived from a sample, wherein the oligonucleotide primers are specific for (i.e. hybridize to) the polynucleotides. The amplified cDNA is then separated and detected using techniques well known in the art, such as gel electrophoresis.

Other exemplary methods known in the art for the quantification of polynucleotide (e.g., mRNA) expression in a sample include northern blotting and in situ hybridization (Parker & Barnes, Methods in Molecular Biology 106:247-283 (1999)); RNase protection assays (Hod, Biotechniques 13:852-854 (1992)); and PCR-based methods, such as reverse transcription PCT (RT-PCR) (Weis et al., Trends in Genetics 8:263-264 (1992)).

In some embodiments, the level of RasGRP1 polynucleotide is measured using a reverse transcriptase-polymerase chain reaction (RT-PCR) or a variant thereof. Useful fluorogenic probe based quantitative PCR methods are described in, e.g., Heid et al., Genome Res, 6:986-94, 1996. The principle of such probe-based quantitative PCR methods utilizes the 5'-3' exonuclease activity of Taq DNA polymerase for direct and specific detection of PCR products via release of fluorescence reporter dyes. In addition to sense and antisense primers, the PCR employs a doubly fluorescently labeled probe (e.g., TaqMan® probe) which hybridizes to a sequence of the PCR product. The probe is labeled 5' with a reporter dye (e.g., FAM) and 3' with a quencher dye (e.g., TAMRA). If the probe is intact, the spatial proximity of reporter to quencher suppresses the emission of reporter fluorescence. If the probe hybridizes to the PCR product during the PCR, said probe is cleaved by the 5'-3' exonuclease activity of Taq DNA polymerase and suppression of the reporter fluorescence is removed. The increase in reporter fluorescence as a consequence of the amplification of the target, is measured after each PCR cycle and utilized for quantification. Expression of the target gene (e.g., RasGRP1) is quantified absolutely or relative to expression of a control gene with constant expression in the tissues to be studied. In some embodiments of the method, a TaqMan® Gene Expression Assay (Life Technologies), such as Hs00996727, Hs00996728, Hs00996724, Hs00996725 and Hs00996729 is used.

Polypeptide expression of RasGRP1 can be detected in suitable cells and tissues, such as tumor sample or tumor cell material obtained by biopsy. Various assay methods are known to those of ordinary skill in the art. The method can include (a) contacting the sample from the subject with a binding agent (e.g., an antibody, an antibody fragment, or an aptamer); (b) detecting in the sample a level of polypeptide that binds to the binding agent; and (c) comparing the level of polypeptide with a predetermined standard or cut-off value. For example, the patient sample, which can be immobilized, can be contacted with an antibody, an antibody fragment, or an aptamer, that selectively binds to RasGFP1, and determining whether the antibody, fragment thereof or aptamer has bound to the protein. Protein expression can be measured using a variety of methods standard in the art, including, but not limited to: Western blot, immunoblot, enzyme-linked immunosorbant assay (ELISA), sandwich immunoassay, radioimmunoassay (RIA), bead-based immunoassay, immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

Commercially available antibodies that specifically bind to RasGRP1 are from, e.g., Life Technologies (Cat. No. PA5-25750), Abcam (Cat. No. ab13987), Novus Biologicals (Cat. No. NBP1-98413), Millipore (Cat. No. MABS146), and Santa Cruz Biotechnology (sc-28581), are useful for the methods provided herein. Antibodies that bind to phosphorylated RasGRP1 are available from Sigma-Aldrich (Cat. No. AB4200337).

B. Detecting Activating KRAS Variants

In some embodiments, the methods of the invention further comprise determining the presence or absence of an activating KRAS gene present in a tumor sample from the patient. As used herein, the term "KRAS mutant" or "KRAS variant" includes a nucleotide sequence of a KRAS gene containing one or more changes as compared to the wild-type KRAS gene or an amino acid sequence of a KRAS polypeptide containing one or more changes as compared to the wild-type KRAS polypeptide sequence. Human KRAS is set forth in NCBI GeneID No. 3845. The mRNA (coding) and polypeptide sequences of human KRAS are set forth in, e.g., Genbank Accession Nos. NM_033360.3, NM_004985.4, NP_203524.1, and NP_004976.2, respectively. In addition, the complete sequence of human chromosome 12 assembly GRCh38, which includes KRAS, is set forth in, e.g., Genbank Accession No. NC_000012.12. Furthermore, the sequence of KRAS from other species can be found in the GenBank database.

Activating KRAS variants can include mutations in exon 2 (codons 12 and 13) and exon 3 (codon 61) of the human KRAS gene. The variant can be, but is not limited to, a KRAS G12C, G12R, G12S, G12A, G12D, G12V, G13C, G13R, G13S, G13A, G13D, G13V, G34T, G34A, G34C, G35T, G35C, G35A, G37T, G37C, G37A, G48T, G38A, G38A, Q61K, Q61L, Q61R, Q61H, K117N, A146P, A146T or A146V variant.

Commercially available assays for detecting KRAS mutations in a biological sample can be used. Non-limiting examples of KRAS mutation detection kits include Cobas® KRAS mutation test (Roche Molecular Diagnostics), Droplet Digital™ PCR (Bio-Rad), TaqMan® Mutation Detection Assay (Thermo Fisher), and TheraScreen® KRAS RGQ (Roto-Gene Q) PCR Kit (Qiagen). Detection of an activating KRAS mutation can be carried out using any of a variety of methods Numerous methods are known in the art for detection of sequence variations (polymorphisms and mutations) in nucleic acid samples, and can be used for detecting an activating KRAS mutation. Such methods include methods based on polymerase chain reaction, or allele specific amplification in combination with DNA sequencing, or TaqMan®. In addition, methods can be designed to detect sequence variants (e.g., known variants) at a targeted position in the nucleic acid sequence. Sequence variants are detected using as probes or primers oligonucleotides that hybridize differentially to each variant. Many approaches have been developed to increase the selectivity of hybridization of sequence specific probes to targeted variants; the extent of hybridization is of the sequence specific probes is often detected based on detecting and/or quantifying the amount of product formed in a subsequent polymerase chain reaction.

C. Kits, Probes and Primers

The present invention contemplates the use of kits, probes and/or primers that can be used to stratify patients between responders and non-responders. Such kits can include reagents that detect the presence of KRAS and RasGRP1 (DNA or mRNA or protein). For example, the kit can include probes and/or primers that selectively hybridize to KRAS DNA or mRNA and can detect the one or more KRAS mutations disclosed herein. The kit can further include reagents such as probes, primers and/or antibodies to detect the presence and quantity of RasGRP1. A kit herein can furthermore include reagents useful for detecting the presence and/or quantity of any one or more of the following markers EGFR, SOS1 and SOS2.

D. Establishing a Threshold Value

In order to establish a threshold value for practicing the method of this invention, a reference population of subjects can be used. In some embodiments, a population of CRC patients receiving an anti-EGFR therapy or another molecular targeted therapy can be used. In some embodiments, the CRC patients in the reference group may receive an anti-EGFR therapy or another molecular targeted therapy, in combination with chemotherapy, radiation therapy and/or surgical resection of the tumor. In other embodiments, the reference population includes subjects who do not have CRC. In yet other embodiments, the reference population includes subjects who have CRC and are not receiving targeted therapy. These patients are within the appropriate parameters, if applicable, for the purpose of screening for and/or monitoring cancer using the methods of the present invention. Optionally, the patients are of same gender, similar age, or similar ethnic background.

The status of the selected patients is confirmed by well established, routinely employed methods including but not limited to general physical examination of the individuals and general review of their medical history.

Furthermore, the selected group of patients must be of a reasonable size, such that the average level/amount/concentration of human RasGRP1 polynucleotide (mRNA) or RasGRP1 protein in the sample obtained from the group can be reasonably regarded as representative of the normal or average level among this population of patients.

Once an average value for the RasGRP1 polynucleotide (mRNA) or RasGRP1 protein is established based on the individual values found in each subject of the selected group, this average or median or representative value or profile is considered a threshold value. A standard deviation is also determined during the same process. In some cases, separate threshold values may be established for separately defined groups having distinct characteristics such as age, gender, or ethnic background.

E. Selecting Drug Therapies or Predicting Response to Drug Therapies

According to the methods described herein, the presence or level of RasGRP1 in the patient's sample is compared to one or more reference or threshold values. In some embodiments, the level of RasGRP1 is deemed "high' if it is at least 1, 2, 3, 4, 5, 10, 15, 20 or more standard deviations greater than the reference value subjects. In other embodiments, the level of RasGRP1 is "low" if it is at least 1, 2, 3, 4, 5, 10, 15, 20 or more standard deviations lower than the reference or threshold value.

Those skilled in the art are familiar with various ways of deriving and using threshold values. For example, the reference value may represent the level, amount or concentration of a RasGRP1 in a sample from a plurality of CRC patient receiving an anti-EGFR therapy. In some instances, reference CRC patients also receive chemotherapy, radiation therapy and/or surgery for tumor removal. If a level, amount or concentration in a sample from the test subject is significantly higher (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than the threshold value, this would indicate, e.g., a likelihood of a good prognosis or a negative clinical response to an anti-EGFR therapy. If a level, amount or concentration in a sample from the test subject is significantly lower (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than the threshold value, this would indicate, e.g., a likelihood of a poor prognosis or a positive clinical response to an anti-EGFR therapy.

In some embodiments, if RasGRP1 level in the sample from the test patient is significantly higher than or above the threshold value, a drug therapy that is not an anti-EGFR therapy is selected for the patient. Rather, a drug therapy comprising a BRAF inhibitor, IGFR inhibitor, MEK inhibitor, PI3K inhibitor, VEGFR inhibitor, or other kinase inhibitor can be recommended to treat the patient with cancer. In some instances, it is determined that tumor cells of this test patient also carry an activating KRAS mutation. In other instances, it is determined that tumor cells of this test patient are wild-type for KRAS.

In other embodiments, if RasGRP1 level in the sample from the test patient is significantly lower than or below the threshold value, an anti-EGFR therapy is selected for the patient. The anti-EGFR therapy can include an EGFR blocking antibody or an EGFR inhibitor. In some instances, it is determined that tumor cells of this test patient also carry an activating KRAS mutation. In other instances, it is determined that tumor cells of this test patient are wild-type for KRAS.

If two or more biomarkers (e.g., RasGRP1 level and presence or absence of activating KRAS variant) are used, an index value may represent the level of the biomarkers. Other markers that can be evaluated include EGFR, SOS1 and SOS2. When two or more biomarkers are used in the method described herein, the level of each biomarker can be weighted and combined. Thus, a test value may be provided by (a) weighting the determined level of each biomarker with a predefined coefficient, and (b) combining the weighted level to provide a test value. The combining step can be either by straight addition or averaging (i.e., weighted equally) or by a different predefined coefficient.

The invention also provides the use of a computer system, such as that described above, which comprises: (1) a computer; (2) a stored bit pattern encoding the biomarker testing results obtained by the methods of the invention, which may be stored in the computer; (3) and, optionally, (4a) a program for selecting a drug therapy for a patient having cancer, (4b) a program for predicting the likelihood of a positive prognosis for a patient having cancer, or (4c) a program for predicting the likelihood of a negative response to an anti-EGFR therapy in a patient having cancer.

In some embodiments, a computer system is used in which a value of RasGRP1 levels in a sample from a patient undergoing testing is entered into the computer and compared to a threshold value. If RasGRP1 level in the sample from the patient undergoing testing is significantly higher than or above the threshold value received by the computer, a drug therapy employing a BRAF inhibitor, IGFR inhibitor, MEK inhibitor, PI3K inhibitor, VEGFR inhibitor, or other kinase inhibitor is identified as a drug therapy to treat the patient. In other embodiments, if a RasGRP1 level in the sample from the patient undergoing testing is significantly lower than or below the threshold value, an anti-EGFR drug therapy, such as an EGFR blocking antibody or EGFR inhibitor is identified as a drug therapy to treat the patient.

The following describes an illustrative computer-implemented method for selecting a drug therapy for a patient based on RasGRP1 levels or for determining the likelihood of a good prognosis or poor prognosis using RasGRP1 levels. Implementations of or processing in the computer-implemented method may be performed by software (e.g., instructions or code modules) when executed by a central processing unit (CPU or processor) of a logic machine, such as a computer system or information processing device, by hardware components of an electronic device or application-specific integrated circuits, or by combinations of software and hardware elements.

In the computer-implemented method, information is received describing the level of RasGRP1 in a sample obtained from a subject. For example, the level of RasGRP1 associated may be recorded. In one embodiment, input data includes a text file (e.g., a tab-delimited text file) of RasGRP1 values. In one embodiment, input data includes a text file (e.g., a tab-delimited text file) of RasGRP1 levels in the sample from the subject.

The information describing the RasGRP1 levels is compared to a threshold value recorded by the computer. A subject's estimated likelihood of a good prognosis if the value is higher than a threshold value, or of a poor prognosis if the RasGRP1 level is lower than the threshold value is determined, added to a summary plot, and output as a new report. In some embodiments, the information describing the RasGRP1 levels is compared to a threshold value recorded by the computer. In some embodiments, the identification of the subject as being a candidate for a non-anti-EGFR therapy if the level of RasGRP1 is higher than a threshold value is determined, added to a summary plot, and output as a new report. In some embodiments, the identification of the subject as being a candidate for an anti-EGFR therapy if the level of RasGRP1 is lower than the threshold value is determined, added to a summary plot, and output as a new report.

Hardware Description

The information obtained from the RasGR1 analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study evaluating RasGRP1 levels in a sample from a patient. Thus, in an exemplary embodiment, the RasGRP1 analysis results are provided to a computer where a central processor executes a computer program for determining the likelihood of a good prognosis or of a poor prognosis. In some embodiments, the central processor executes a code for selecting a drug therapy where a non-anti-EGFR therapy is selected if the level of RasGRP1 is higher than a threshold value. In some embodiments, the central processor executes a code for selecting a drug therapy where an anti-EGFR therapy is selected if the level of RasGRP1 is lower than a threshold value.

The invention thus includes a computer system to implement the method for determining the likelihood of a good prognosis or a poor prognosis; or to implement the method for selecting a drug therapy. Such a computer system can comprise code for interpreting the results of an analysis evaluating the level of RasGRP1 levels in a sample obtained from the subject. Thus in an exemplary embodiment, the expression analysis results are provided to a computer where a central processor executes a computer program for determining the likelihood of a good or poor prognosis in the subject and/or for selecting a drug therapy for the subject.

The invention also provides the use of a computer system, such as that described above, which comprises: (1) a computer; (2) a stored bit pattern encoding the RasGRP1 levels in a sample obtained from the patient, e.g., a tumor biopsy sample, which may be stored in the computer; and, optionally, (3) a program for determining the level compared to a threshold level.

The invention further provides methods of generating a report based on the RasGRP1 level in a sample obtained from the patient.

Figure 17:
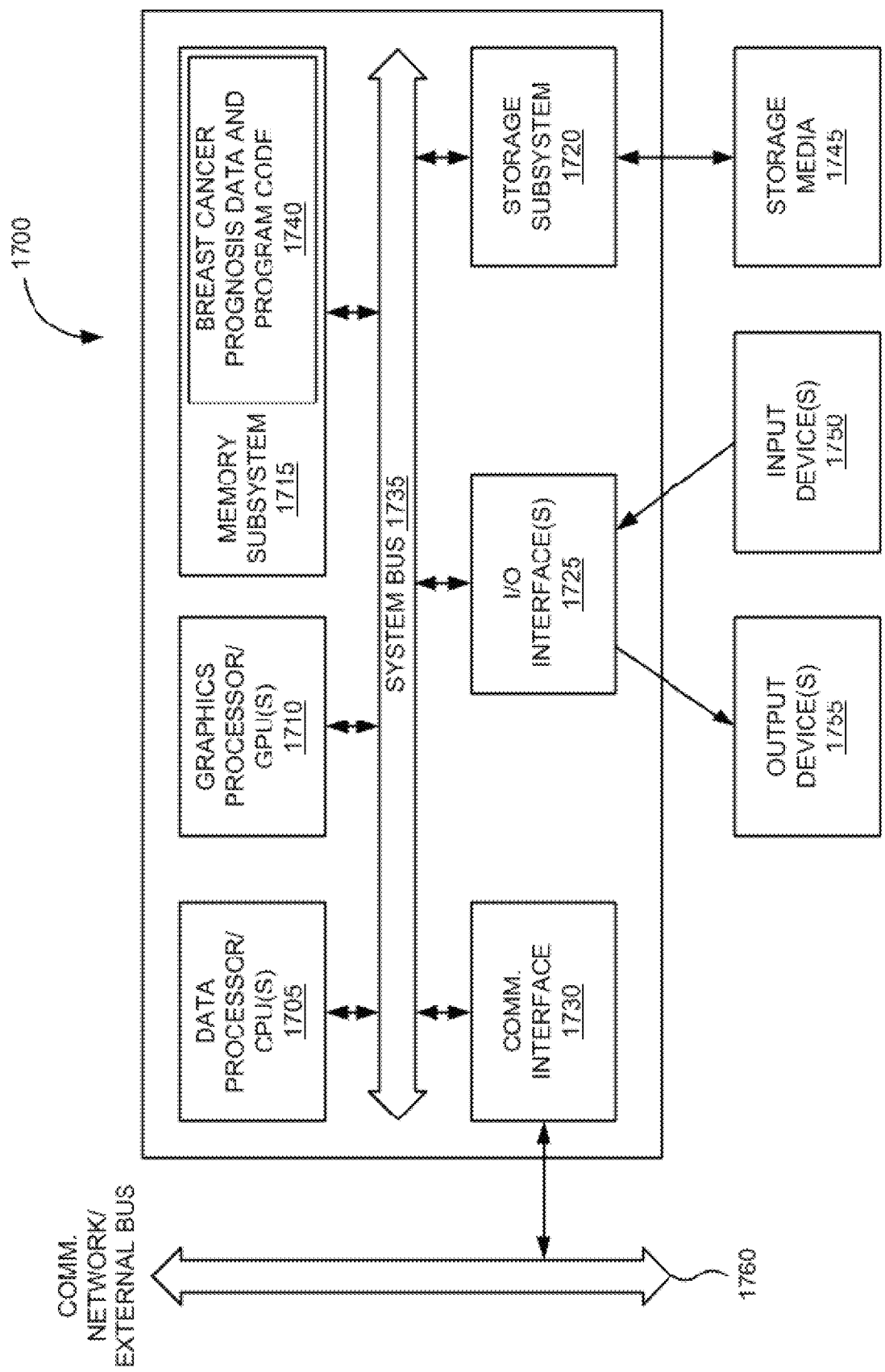
FIG. 17 is a block diagram of computer system 1700 that may incorporate an embodiment, be incorporated into an embodiment, or be used to practice any of the innovations, embodiments, and/or examples found within this disclosure.

FIG. 17 is a block diagram of a computer system 1700 that may incorporate an embodiment, be incorporated into an embodiment, or be used to practice any of the innovations, embodiments, and/or examples found within this disclosure. FIG. 17 is merely illustrative of a computing device, general-purpose computer system programmed according to one or more disclosed techniques, or specific information processing device for an embodiment incorporating an invention whose teachings may be presented herein and does not limit the scope of the invention as recited in the claims. One of ordinary skill in the art would recognize other variations, modifications, and alternatives.

Computer system 1700 can include hardware and/or software elements configured for performing logic operations and calculations, input/output operations, machine communications, or the like. Computer system 1700 may include familiar computer components, such as one or more one or more data processors or central processing units (CPUs) 1705, one or more graphics processors or graphical processing units (GPUs) 1210, memory subsystem 1715, storage subsystem 1720, one or more input/output (I/O) interfaces 1725, communications interface 1730, or the like. Computer system 1700 can include system bus 1735 interconnecting the above components and providing functionality, such connectivity and inter-device communication. Computer system 1700 may be embodied as a computing device, such as a personal computer (PC), a workstation, a mini-computer, a mainframe, a cluster or farm of computing devices, a laptop, a notebook, a netbook, a PDA, a smartphone, a consumer electronic device, a gaming console, or the like.

The one or more data processors or central processing units (CPUs) 1705 can include hardware and/or software elements configured for executing logic or program code or for providing application-specific functionality. Some examples of CPU(s) 1705 can include one or more microprocessors (e.g., single core and multi-core) or micro-controllers. CPUs 1705 may include 4-bit, 8-bit, 12-bit, 16-bit, 32-bit, 64-bit, or the like architectures with similar or divergent internal and external instruction and data designs. CPUs 1705 may further include a single core or multiple cores. Commercially available processors may include those provided by Intel of Santa Clara, Calif. (e.g., x86, x86_64, PENTIUM, CELERON, CORE, CORE 2, CORE ix, ITANIUM, XEON, etc.) or by Advanced Micro Devices of Sunnyvale, Calif. (e.g., x86, AMC_64, ATHLON, DURON, TURION, ATHLON XP/64, OPTERON, PHENOM, etc). Commercially available processors may further include those conforming to the Advanced RISC Machine (ARM) architecture (e.g., ARMv7-9), POWER and POWERPC architecture, CELL architecture, and or the like. CPU(s) 1705 may also include one or more field-gate programmable arrays (FPGAs), application-specific integrated circuits (ASICs), or other microcontrollers. The one or more data processors or central processing units (CPUs) 1705 may include any number of registers, logic units, arithmetic units, caches, memory interfaces, or the like. The one or more data processors or central processing units (CPUs) 1705 may further be integrated, irremovably or moveably, into one or more motherboards or daughter boards.

The one or more graphics processor or graphical processing units (GPUs) 1710 can include hardware and/or software elements configured for executing logic or program code associated with graphics or for providing graphics-specific functionality. GPUs 1710 may include any conventional graphics processing unit, such as those provided by conventional video cards. Some examples of GPUs are commercially available from NVIDIA, ATI, and other vendors. In various embodiments, GPUs 1710 may include one or more vector or parallel processing units. These GPUs may be user programmable, and include hardware elements for encoding/decoding specific types of data (e.g., video data) or for accelerating 2D or 3D drawing operations, texturing operations, shading operations, or the like. The one or more graphics processors or graphical processing units (GPUs) 1710 may include any number of registers, logic units, arithmetic units, caches, memory interfaces, or the like. The one or more data processors or central processing units (CPUs) 1705 may further be integrated, irremovably or moveably, into one or more motherboards or daughter boards that include dedicated video memories, frame buffers, or the like.

Memory subsystem 1715 can include hardware and/or software elements configured for storing information. Memory subsystem 1715 may store information using machine-readable articles, information storage devices, or computer-readable storage media. Some examples of these articles used by memory subsystem 1715 can include random access memories (RAM), read-only-memories (ROMS), volatile memories, non-volatile memories, and other semiconductor memories. In various embodiments, memory subsystem 1715 can include data and program code 1740.

Storage subsystem 1720 can include hardware and/or software elements configured for storing information. Storage subsystem 1720 may store information using machine-readable articles, information storage devices, or computer-readable storage media. Storage subsystem 1720 may store information using storage media 1745. Some examples of storage media 1745 used by the storage subsystem 1720 can include floppy disks, hard disks, optical storage media such as CD-ROMS, DVDs and bar codes, removable storage devices, networked storage devices, or the like. In some embodiments, all or part of the RasGRP1 data and program code 1740 may be stored using the storage subsystem 1720.

In various embodiments, computer system 1700 may include one or more hypervisors or operating systems, such as WINDOWS, WINDOWS NT, WINDOWS XP, VISTA, WINDOWS 7 or the like from Microsoft of Redmond, Wash., Mac OS or Mac OS X from Apple Inc. of Cupertino, Calif., SOLARIS from Sun Microsystems, LINUX, UNIX, and other UNIX-based or UNIX-like operating systems. Computer system 1700 may also include one or more applications configured to execute, perform, or otherwise implement techniques disclosed herein. These applications may be embodied as cancer prognosis data and the program code 1740. Additionally, computer programs, executable computer code, human-readable source code, shader code, rendering engines, or the like, and data, such as image files, models including geometrical descriptions of objects, ordered geometric descriptions of objects, procedural descriptions of models, scene descriptor files, or the like, may be stored in the memory subsystem 1715 and/or storage subsystem 1720.

The one or more input/output (I/O) interfaces 1725 can include hardware and/or software elements configured for performing I/O operations. One or more input devices 1750 and/or one or more output devices 1755 may be communicatively coupled to the one or more I/O interfaces 1725.

The one or more input devices 1750 can include hardware and/or software elements configured for receiving information from one or more sources for computer system 1700. Some examples of the one or more input devices 1750 may include a computer mouse, a trackball, a track pad, a joystick, a wireless remote, a drawing tablet, a voice command system, an eye tracking system, external storage systems, a monitor appropriately configured as a touch screen, a communications interface appropriately configured as a transceiver, or the like. In various embodiments, the one or more input devices 1750 may allow a user of the computer system 1700 to interact with one or more non-graphical or graphical user interfaces to enter a comment, select objects, icons, text, user interface widgets, or other user interface elements that appear on a monitor/display device via a command, a click of a button, or the like.

The one or more output devices 1755 can include hardware and/or software elements configured for outputting information to one or more destinations for computer system 1700. Some examples of the one or more output devices 1755 can include a printer, a fax, a feedback device for a mouse or joystick, external storage systems, a monitor or other display device, a communications interface appropriately configured as a transceiver, or the like. The one or more output devices 1755 may allow a user of the computer system 1700 to view objects, icons, text, user interface widgets, or other user interface elements.

A display device or monitor may be used with computer system 1700 and can include hardware and/or software elements configured for displaying information. Some examples include familiar display devices, such as a television monitor, a cathode ray tube (CRT), a liquid crystal display (LCD), or the like.

Communications interface 1730 can include hardware and/or software elements configured for performing communications operations, including sending and receiving data. Some examples of the communications interface 1730 may include a network communications interface, an external bus interface, an Ethernet card, a modem (telephone, satellite, cable, ISDN), (asynchronous) digital subscriber line (DSL) unit, FireWire interface, USB interface, or the like. For example, communications interface 1730 may be coupled to communications network/external bus 1780, such as a computer network, to a FireWire bus, a USB hub, or the like. In other embodiments, communications interface 1730 may be physically integrated as hardware on a motherboard or daughter board of computer system 1700, may be implemented as a software program, or the like, or may be implemented as a combination thereof.

In various embodiments, computer system 1700 may include software that enables communications over a network, such as a local area network or the Internet, using one or more communications protocols, such as the HTTP, TCP/IP, RTP/RTSP protocols, or the like. In some embodiments, other communications software and/or transfer protocols may also be used, for example IPX, UDP or the like, for communicating with hosts over the network or with a device directly connected to computer system 1700.

FIG. 17 is merely representative of a general-purpose computer system appropriately configured or specific data processing device capable of implementing or incorporating various embodiments of an invention presented within this disclosure. Many other hardware and/or software configurations may be apparent to the skilled artisan which are suitable for use in implementing an invention presented within this disclosure or with various embodiments of an invention presented within this disclosure. For example, a computer system or data processing device may include desktop, portable, rack-mounted, or tablet configurations. Additionally, a computer system or information processing device may include a series of networked computers or clusters/grids of parallel processing devices. In still other embodiments, a computer system or information processing device may perform techniques described above as implemented upon a chip or an auxiliary processing board.

Many hardware and/or software configurations of a computer system may be apparent to the skilled artisan, which are suitable for use in implementing a computer-based method of determining the likelihood of a good or poor prognosis RasGRP1 levels described herein. For example, a computer system or data processing device may include desktop, portable, rack-mounted, or tablet configurations. Additionally, a computer system or information processing device may include a series of networked computers or clusters/grids of parallel processing devices. In still other embodiments, a computer system or information processing device may use techniques described above as implemented upon a chip or an auxiliary processing board.

Various embodiments of an algorithm as described herein can be implemented in the form of logic in software, firmware, hardware, or a combination thereof. The logic may be stored in or on a machine-accessible memory, a machine-readable article, a tangible computer-readable medium, a computer-readable storage medium, or other computer/machine-readable media as a set of instructions adapted to direct a central processing unit (CPU or processor) of a logic machine to perform a set of steps that may be disclosed in various embodiments of an invention presented within this disclosure. The logic may form part of a software program or computer program product as code modules become operational with a processor of a computer system or an information-processing device when executed to perform a method or process in various embodiments of an invention presented within this disclosure. Based on this disclosure and the teachings provided herein, a person of ordinary skill in the art will appreciate other ways, variations, modifications, alternatives, and/or methods for implementing in software, firmware, hardware, or combinations thereof any of the disclosed operations or functionalities of various embodiments of one or more of the presented inventions.

F. Drug Therapies

The methods provided herein can be used to select or predict a response (negative response or positive response) to an anti-EGFR therapy in a patient with cancer. An anti-EGFR therapy includes any therapeutic agent that blocks or inhibits the expression or activity of the EGFR gene and/or its expression products and any signaling molecule acting in the EGFR signaling pathway. Non-limiting anti-EGFR therapies include an EGFR blocking antibody, such as, cetuximab (Erbitux®) and panitumumab (Vectibix™), or an EGFR inhibitor, such as erlotinib (Tarceva®), gefitinib (Iressa®), lapatinib (GW-572016; Tykerb®), and vandetanib (ZACTIMA™; ZD6474).

Non-limiting non anti-EGFR therapies include a BRAF inhibitor, such as vemurafenib and abrafenib; Akt inhibitor such as GSK2141795 and MK2206; MEK inhibitor, such as trametinib (Mekinist™), TAK-733, selumetinib, and MEK162; VEGF inhibitor, such as bevacizumab (Avastie), Aflibercept and BAY43-9006; and other kinase inhibitors, such as sunitinib (Sutene), canertinib (CI 1033), semaxinib (SU5416), vatalanib (PTK787/ZK222584), sorafenib (BAY 43-9006; Nexavar®), regorafenib, imatinib mesylate (Gleevec®), leflunomide (SU101), alisertib (MLN8237), pelitinib, CP-654577, CP-724714, HKI-272, PKI-166, AEE788, BMS-599626, HKI-357, BIBW 2992, ARRY-334543, JNJ-26483327, and JNJ-26483327; and combinations thereof. Non-limiting examples of c-Met inhibitors include monoclonal antibodies such as AMG102 and Met-MAb; small molecule inhibitors of c-Met such as ARQ197, JNJ-38877605, PF-04217903, SGX523, GSK 1363089/XL880, XL184, MGCD265, and MK-2461; and combinations thereof.

The molecular targeted therapies described herein, such as anti-EGFR therapies and non anti-EGFR therapies, can be administered to a patient with cancer in combination with other types of cancer therapy. Non-limiting examples of cancer therapies or cancer treatments include chemotherapy, radiation therapy, and surgical removal of tumors. In some embodiments, a patient with receiving an anti-EGFR therapy can also receive chemotherapy, radiation therapy, and/or surgical resectioning. In other embodiments, a patient with receiving a non anti-EGFR therapy can also receive chemotherapy, radiation therapy, and/or surgical resectioning.

III. Examples

The following examples are offered to illustrate, but not to limit the claimed invention. Those of skill in the art will readily recognize a variety of noncritical parameters that could be changed or modified to yield essentially similar results.

Example 1. The Ras Exchange Factor RasGRP1 Opposes Proliferative EGFR-SOS1 Ras Signals and Restricts Intestinal Epithelial Cell Growth The character of EGFR signals can influence cell fate but mechanistic insights into intestinal EGFR-Ras signalling are limiting. Here we show that two distinct Ras nucleotide exchange factors, RasGRP1 and SOS1, lie downstream of the EGFR but act in functional opposition. RasGRP1 is expressed in the intestinal crypt compartment where it restricts epithelial growth. RasGRP1 is also expressed in colorectal cancer (CRC) cell lines and patient samples and high RasGRP1 expression correlates with a better clinical outcome. Biochemically, we find that RasGRP1 creates a negative feedback loop that limits proliferative EGFR-SOS1-Ras signals in CRC cells. Genetic Rasgrp1 depletion from mice with either an activating mutation in KRas ($KRas^{G12D}$) or with aberrant Wnt signalling due to a mutation in Apc ($Apc^{Min/+}$) resulted in both cases in exacerbated Ras-ERK signalling and cell proliferation. The unexpected opposing cell biological effects of EGFR-RasGRP1 and EGFR-SOS1 signals in the same cell shed new light on the intricacy of EGFR-Ras signalling in the normal epithelium and in carcinoma.

Introduction

Ras is a molecular switch, activated through GTP-loading by Ras guanine nucleotide exchange factors (RasGEFs) in response to receptor signals[1]. The amplitude and duration of epidermal growth factor receptor (EGFR) signalling to Ras and its downstream target MAPK (MAP kinase) affects cell fate; EGF stimulation of rat adrenal pheochromocytoma (PC-12) cells leads to transient Ras activation and proliferation. By contrast, NGF or EGF stimulation of PC12 cells overexpressing the EGFR results in sustained Ras-MAPK activation, exit from mitosis, and differentiation[2]. Lymphocytes stimulated through the T-cell receptor (TCR) also display distinct patterns of Ras-MAPK activation[3,4] and deficiency of either Rasgrp1 or Sos1 RasGEFs impact T cell development at distinct stages[5-8]. We have shown that the type of RasGEF utilized dictates the pattern of Ras activation; RasGRP1 (Ras guanine nucleotide releasing protein-1) transmits analog Ras signals while SOS1 (Son of Sevenless-1) transmits digital Ras signals[4]. Digital Ras activation critically relies on allosteric activation of SOS, which is accomplished by Ras-GTP binding to an allosteric pocket in SOS[9] and creates a positive feedback loop in various cell types[4,10,11].

Ras plays an important role in cancer and thirty percent of metastatic cancers carry somatic KRAS mutations (termed $KRAS^{MUT}$ here), such as $KRAS^{G12D}$. These mutations impair RasGAP-mediated Ras inactivation, culminating in high levels of constitutively active KRAS-GTP and strong proliferative signals[1,12,13]. Colorectal cancer (CRC) is the third most common cancer in the United States[14] and CRC tumors carry $KRAS^{MUT}$ in approximately 40% of patients[15]. Cancer therapy via molecular inhibition of specific targets is a highly sought-after goal but the complexity of cancer signalling pathways is a major challenge[16,17] There is widespread EGFR expression in CRC[15] but clinical trials with anti-EGFR blocking antibodies or inhibitors of the EGFR kinase (e.g. Cetuximab, Gefitinib, or Erlotinib) have been disappointing for CRC, particularly when tumors carry $KRAS^{MUT}$[18,19]. By contrast, such therapies have been successful in non-small-cell lung cancer (NSCLC) patients with EGFR mutations[19]. The most intuitive explanation for failure of anti-EGFR therapy in $KRAS^{MUT}$ CRC is that the constitutive activity of $KRAS^{MUT}$ bypasses regulation mediated by the EGFR. However, recent studies indicate that EGFR signals can modulate tumor growth in the context of $KRAS^{MUT}$. In mice, EGFR signalling is essential for $KRAS^{MUT}$-driven pancreatic ductal carcinoma (PDAC)[20, 21] and in the clinic Erlotinib is beneficial for a limited number of PDAC patients[22]. Thus, $KRAS^{MUT}$ appear not to operate entirely autonomously but seem influenced by EGFR signalling but mechanistic insights in CRC are largely lacking.

Egfr deficiency in mice results in crypt defects in the normal intestine[23] and EGFR-Ras signalling in intestinal progenitor cells are believed to balance proliferation and differentiation[24], although mechanistic insights in the cell biology are very limited. We recently established that RasGRP1 is structurally distinct from SOS1 and lacks an allosteric activation mechanism triggered by Ras-GTP[9, 25]. We postulated that RasGRP1 and SOS1 RasGEFs may play distinct roles in EGFR signalling. Through database mining, we first revealed that RasGRP1 is expressed in CRC cell lines and in CRC patient samples. We confirmed RasGRP1 expression in patient specimens recovered from surgeries. We established that RasGRP1 is also expressed in the normal intestinal epithelium, responds to EGF signal input, but restricts proliferation in the normal epithelium. Genetic ablation of Rasgrp1 alleles exacerbates $KRas^{G12D}$-induced proliferative dysplasia of the intestinal epithelium, resembling human hyperplastic, serrated polyps[26]. We show that upon EGF stimulation, RasGRP1 and SOS1 act in functional opposition to one another in the context of $KRAS^{MUT}$. Rasgrp1 plays an unexpected suppressive role by constituting a negative feedback loop to the EGFR. Reduction of RasGRP1 expression increases EGFR-SOS-Ras signalling and enhances the in vitro and in vivo growth of $KRAS^{MUT}$ CRC cells. We established that higher RasGRP1 expression not only correlates with better clinical outcome of patients with $KRAS^{MUT}$ tumors but also when tumors are wildtype for KRAS. In agreement with a more general suppressive role of RasGRP1, loss of this RasGEF also exacerbates the phenotype of the $Apc^{Min/+}$ mouse model of colorectal cancer. Our results reveal significant new insights in the EGFR-Ras pathway and how nuances in EGFR-Ras signals impact cell biology.

Results

RasGRP1 Expression in CRC

A DT40 B cell model engineered to express the EGFR in addition to the endogenously expressed B cell receptor (BCR) has been useful to dissect different signalling pathways. Initially, it was proposed that SOS1 couples to the EGFR in these cells but not to the BCR, whereas the inverse was suggested for RasGRP1[27]. These conclusions were subsequently adjusted when it became clear that SOS1 does play a role downstream of the BCR when the strength of stimulation is at lower, more physiological levels[4, 11] (for review see[28]). Here we explored this DT40 system and utilized more modest levels of EGF stimulation. In contrast to the initial report[27], we found that ERK activation is reduced in EGF-stimulated DT40 cells that lack RasGRP1 and RasGRP3 (FIGS. 1a and 1b). SOS1 is ubiquitously expressed while RasGRP1 has specific expression patterns in cells of the immune system, skin, and brain[5]. Rasgrp1 deficient mice have a T cell development defect[8], suggesting an immune cell-centric role for Rasgrp1. However, Rasgrp1 was originally identified through a fibroblast transformation assay[29], arguing that Rasgrp1 can affect the function of multiple cell lineages. Our DT40 data implied that RasGRP1 might play an unappreciated role downstream of EGFR signalling and in epithelial cell lineages that respond to EGF.

Figure 1D:
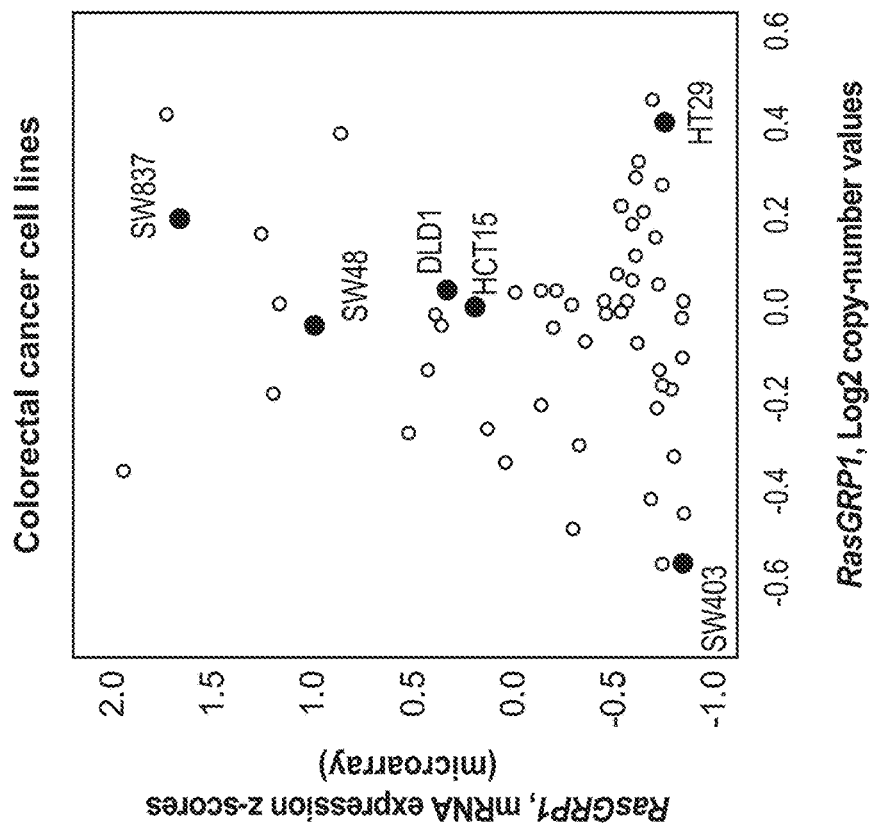
Figure 1C:
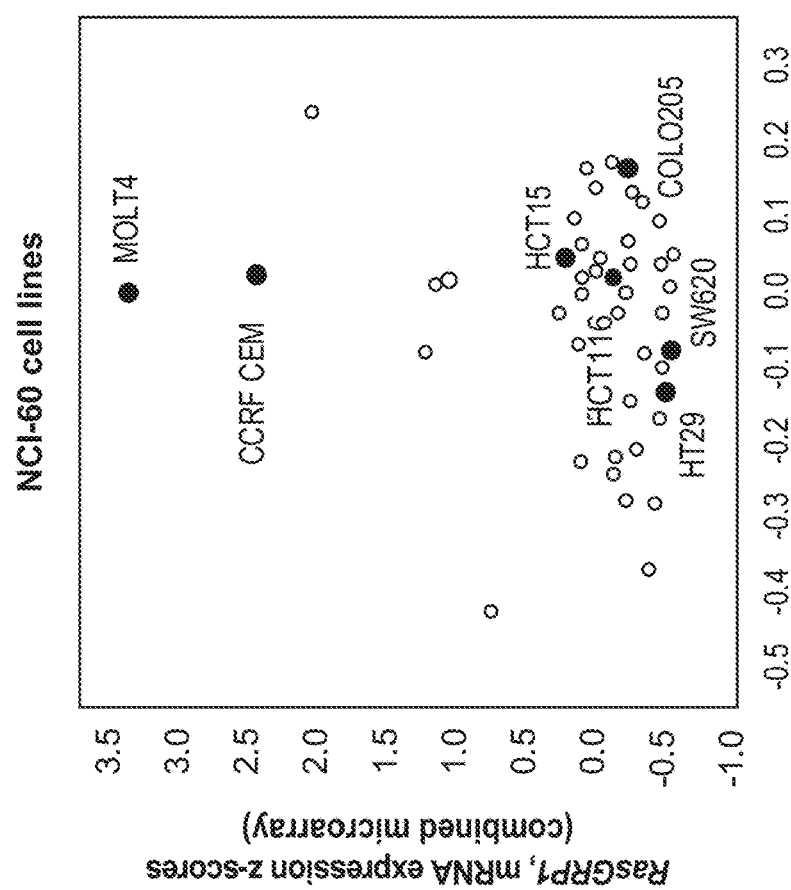
Figure 1E:
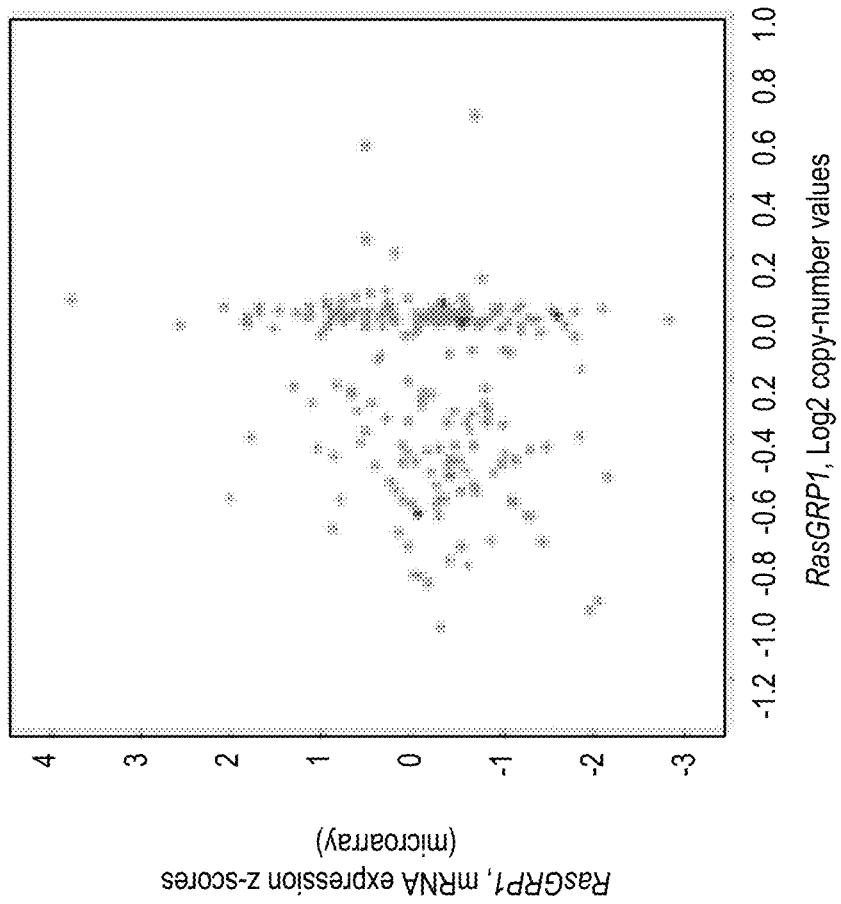
Figures 1F, 1G, 1H:
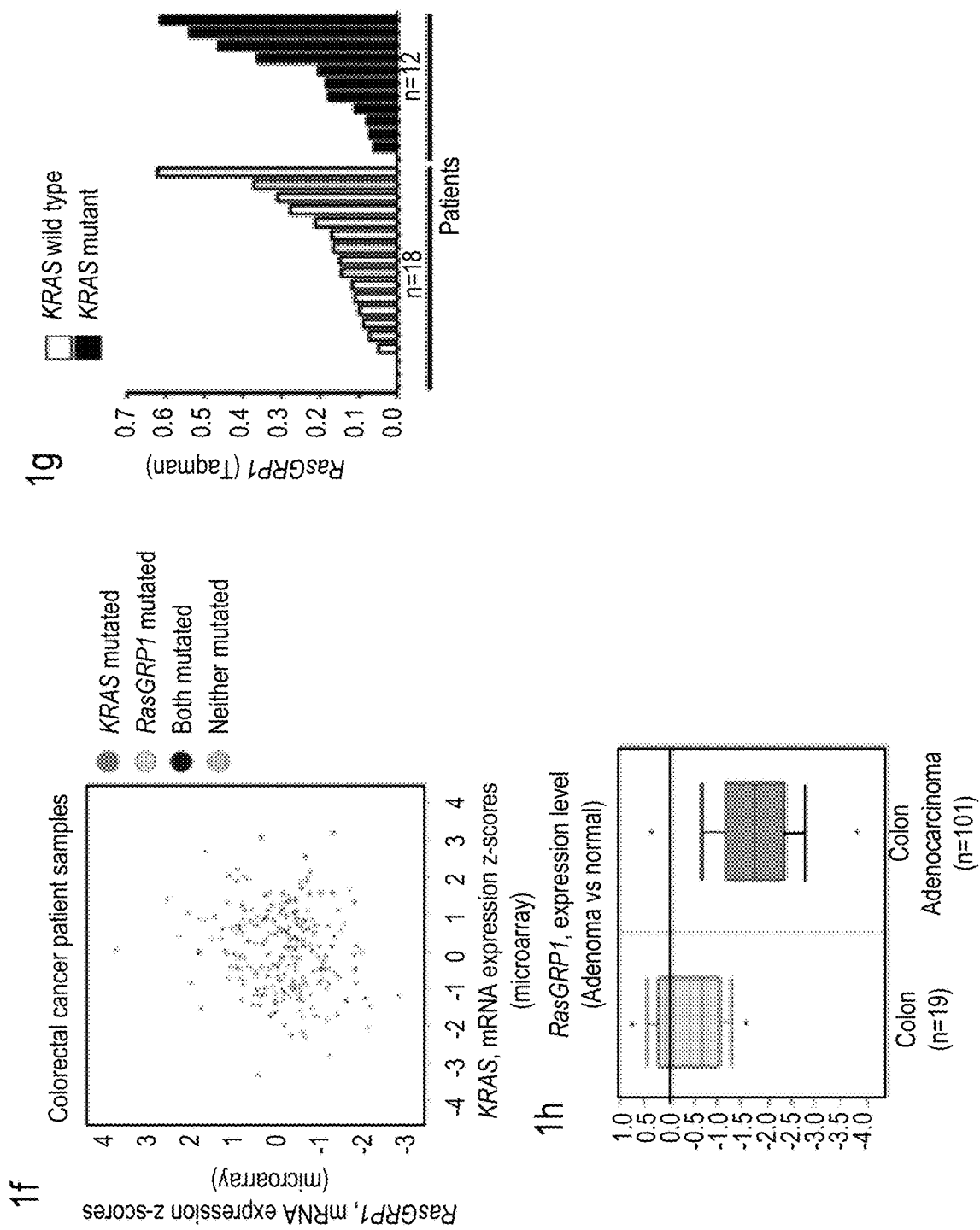

We next used cBio portal[30] to mine The Cancer Genome Atlas (TCGA) for RasGRP1 and plotted RasGRP1 expression levels in 60 cancer cell lines (NCI-60 panel[31]). High expression of this RasGEF occurs in T cell leukaemia lines MOLT4 and CEM, as we previously reported[32], but RasGRP1 expression can also be detected in various CRC cell lines, albeit at lower levels (FIG. 1c). RasGRP1 mRNA levels covered a dynamic range, both in 56 established CRC cell lines (FIG. 1d) and in 276 CRC patient samples (FIG. 1e). The RasGRP1 expressed typically consists of the wild type sequence, and variants or mutations in RasGRP1 are rare in CRC samples (5 out of 276, FIG. 1e). A very similar range of RasGRP1 expression levels can be observed in the 276 tumors when these are stratified and color-coded for CRC with either wild type KRAS or with $KRAS^{MUT}$ (FIG. 1f), an observation that we confirmed by Taqman-based RasGRP1 expression in liver metastases of colorectal cancer patients recovered from surgeries (FIG. 1g). We next used the Oncomine database (at the oncomine.org website) and uncovered that the RasGRP1 expression levels in colonic adenocarcinomas are at a statistically significantly lower level when compared to RasGRP1 in the normal colonic epithelium (FIG. 1h),[33-36] suggesting that RasGRP1 may play a protective role in CRC.

Rasgrp1 Regulates Homeostasis of Normal Intestinal Epithelial Cells

The single-layered intestinal epithelium is a conveyer belt of cells that turns over every 4-5 days; Wnt signals in the bottom of the crypt regulate self-renewal of stem cells and the production of daughter cells that move up to undergo a proliferative phase in response to EGFR signals, followed by terminal differentiation, apoptosis, and shedding into the lumen[33, 34]. In *Drosophila*, EGFR signalling is critical for intestinal maintenance[35, 36]. In the mouse, deficiency in egfr results in disorganized crypts[23] and fine-tuning of EGFR signalling is critical to regulate proliferation in the intestinal stem cell niche[37]. In the human intestine, EGFR-Ras signalling occurs in progenitor cells in the transit-amplifying (T/A) zone in the intestinal crypts, where it is thought to control proliferation and differentiation[24].

Figures 2A, 2B, 2C:
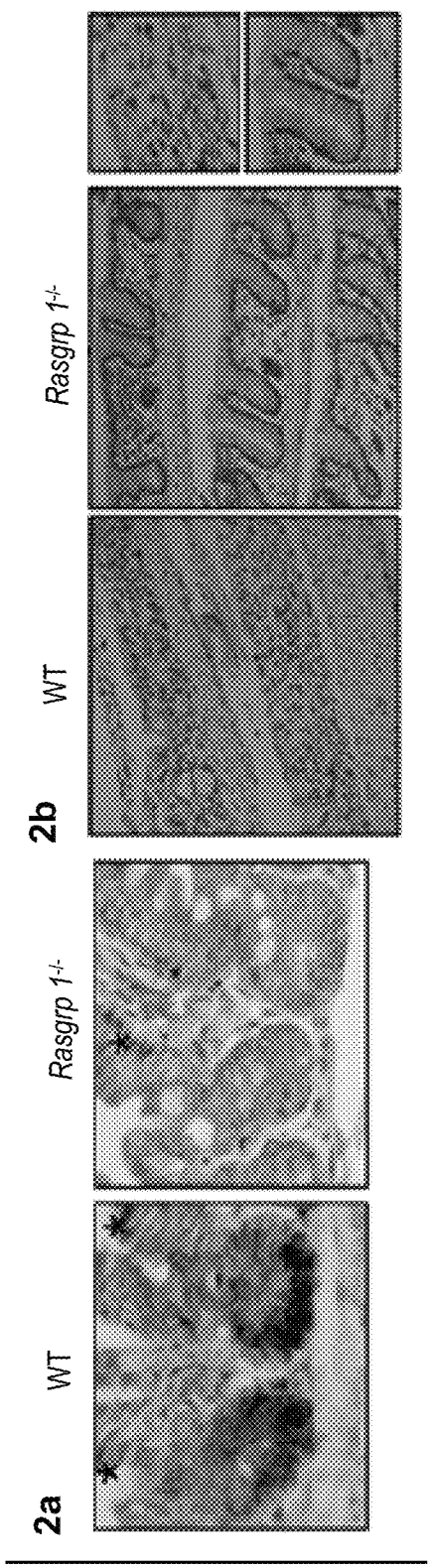
FIGS. 2a-2l illustrate that Rasgrp1 plays a role in intestinal epithelial cell proliferation and goblet cell generation. Immunohistochemistry for Rasgrp1 protein in the small intestines of wildtype or Rasgrp1$^{-/-}$ mice. The asterisks denote nonspecific staining observed in both mouse models (FIG. 2a). Rasgrp1 deficient mice demonstrate resistance to DSS-induced colitis (FIG. 2b). Representative images of a cohort of n=5 for WT and n=6 for Rasgrp1$^{-/-}$; 5 days of DSS treatment. Colonic fields were scored for mucosal damage, ranging from 0-12, following published parameters[79]. Average WT score=10, Rasgrp1$^{-/-}$ score=5. Scores are presented in FIG. 1c. Bar graphs of mucosal damage scores following 5 days of DSS treatment. n=5 for WT and n=6 for Rasgrp1$^{-/-}$ (FIG. 2c). Colonic fields were scored for mucosal damage, ranging from 0-12, following published parameters. p=0.0115 (unpaired t test). Short- (2 hr., FIG. 2d) and long-term (48 hr., FIG. 2e) in vivo BrdU labeling assay revealing proliferating cells in the colon of wildtype or Rasgrp1$^{-/-}$ mice. Scale bars, 100 μm. Quantification and statistical analysis of BrdU-positive cells counted in the colon (FIG. 2f). Three mice per genotype and fifty crypts per mouse were counted and averages±s.e.m are depicted. ***p<0.0001 (t-test). As in FIG. 2e. long-term (48 hr.) in vivo BrdU labeling in the small intestine (FIG. 2g). Scale bars, 100 μm. Positioning of BrdU-positive cells in the small intestine (FIG. 2h). Three mice per genotype and twenty crypt-villus axes were counted. Data were represented as percentage of cells per position±s.e.m. Representative images of small intestines of WT- and Rasgrp1$^{-/-}$-mice stained for cleaved caspase-3 (red) and DAPI (blue) (FIG. 2i). Scale bars, 100 μm. Quantification of cleaved caspase-3-positive cells in the small intestine from mice with the indicated genotype (FIG. 2j). Fifty villi per genotype (n=3) that were transversally sectioned were counted and averages±s.e.m are depicted. *p<0.05 (t-test). Alcian blue staining (FIG. 2k) to visualize goblet cell presence in the small intestine (duodenum).
Figures 2D, 2E, 2F:
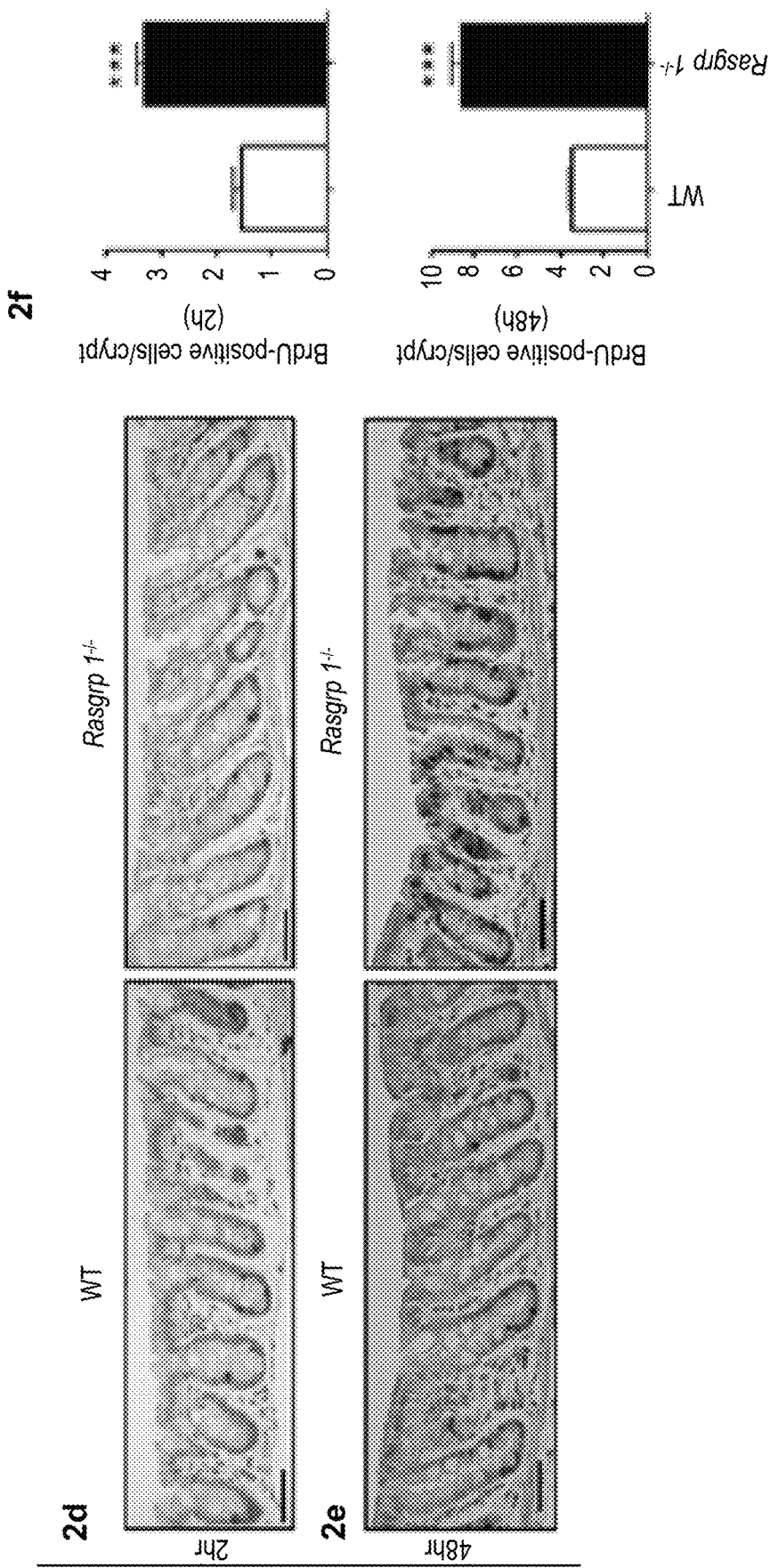
Figures 2G, 2H, 2I, 2J, 2K, 2L:
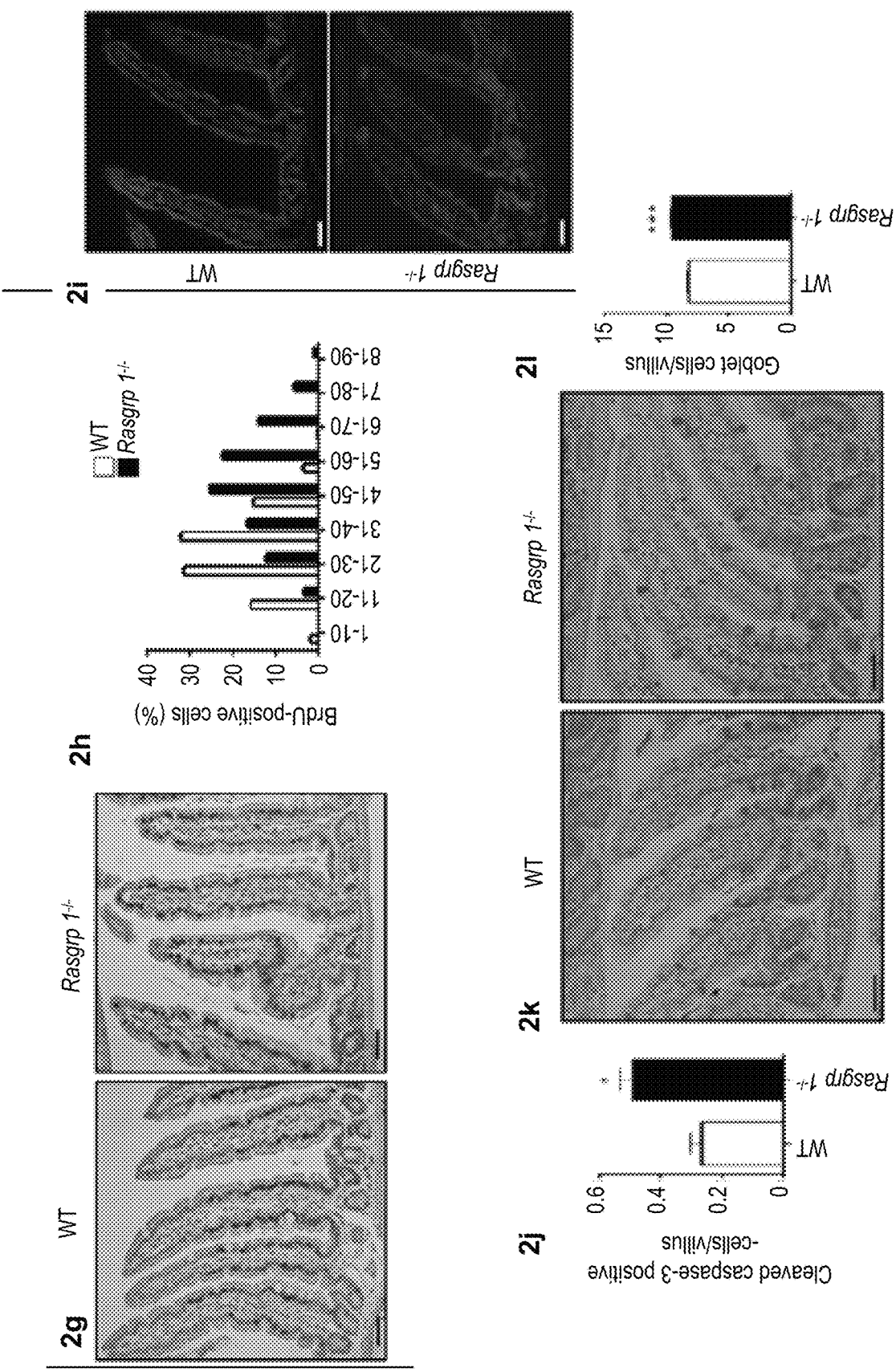

Immunohistochemistry revealed Rasgrp1-positive cells in the crypts of the small intestine of wild type mice and no Rasgrp1-staining in the comparable regions of Rasgrp1-deficient mice (FIG. 2a). $Rasgrp1^{-/-}$ mice do not display wasting disease or other gross intestinal abnormalities. To test if a role for Rasgrp1 in intestinal epithelium may be revealed under circumstances of injury and repair, we exposed $Rasgrp1^{-/-}$ mice to a well-established model of colitis[38]. Remarkably, $Rasgrp1^{-/-}$ mice showed partial protection from DSS (dextran sulfate sodium)-induced colitis and retained a relatively normal architecture of the colonic epithelium (FIGS. 2b and c). The lack of T lymphocytes in $Rasgrp1^{-/-}$ mice unlikely provides the protection since DSS induces profound colitis in other mouse models devoid of T lymphocytes[38]. We postulated that the partial protection could be caused by a difference intrinsic to the epithelial cells in $Rasgrp1^{-/-}$ mice and characterized the proliferative capacity next. In vivo BrdU-labeling at 2 hours (FIG. 2d) and 48 hours (FIG. 2e) revealed that colonic intestinal epithelial cells without Rasgrp1 proliferate more extensively compared to wildtype cells (FIG. 2f). In the Rasgrp1 deficient small intestine, $BrdU^+$ cells were found at the top of the villus, 2 days after BrdU administration, whereas the furthest-progressed wildtype $BrdU^+$ cells positioned midway along the crypt-villus axis (FIGS. 2g and 2h). We also observed increased numbers of cells that stained positive for cleaved caspase-3 in Rasgrp1$^{-/-}$ mice compared to WT mice (FIGS. 2i and 2j). Thus, Rasgrp1 deficiency alters normal intestinal homeostasis and leads to increased proliferation of intestinal cells accompanied by increased apoptosis at the tip of the villi. In addition, loss of Rasgrp1 resulted in small but consistent increases in numbers of goblet cells in the small intestine, revealed by Alcian blue staining (FIGS. 2k and 2l). Of note, the increased numbers of goblet cells that typically produce mucus may provide an additional explanation for the reduced DSS colitis in Rasgrp1$^{-/-}$ mice.

Deletion of Rasgrp1 Exacerbates Intestinal Dysplasia in KRas$^{G12D}$ Mice

Given the findings in FIGS. 1 and 2, we next explored the role of RasGRP1 in the intestinal epithelium in the context of KRAS$^{MUT}$, a somatic mutation found in ~40% of CRC patients[15]. Expression of KRas$^{G12D}$ in the intestinal epithelium of mice produces aberrant cell proliferation and hyperplasia accompanied by relatively intact terminal differentiation[39-41]. To test the role of Rasgrp1 when the intestinal epithelium expresses KRas$^{G12D}$, we reduced the Rasgrp1 expression in Villin-Cre:KRas$^{LSL-G12D}$ mice[40] (termed KRas$^{G12D}$ here) by crossing them to Rasgrp1$^{-/-}$ mice[8]. We used Villin-Cre mice as control (termed wildtype—WT— here). Heterozygosity for Rasgrp1 result in half the Rasgrp1 protein dosage[42], whereas Rasgrp1 deficient mice express no Rasgrp1 protein[8] (FIG. 2a).

Figures 3A, 3Q:
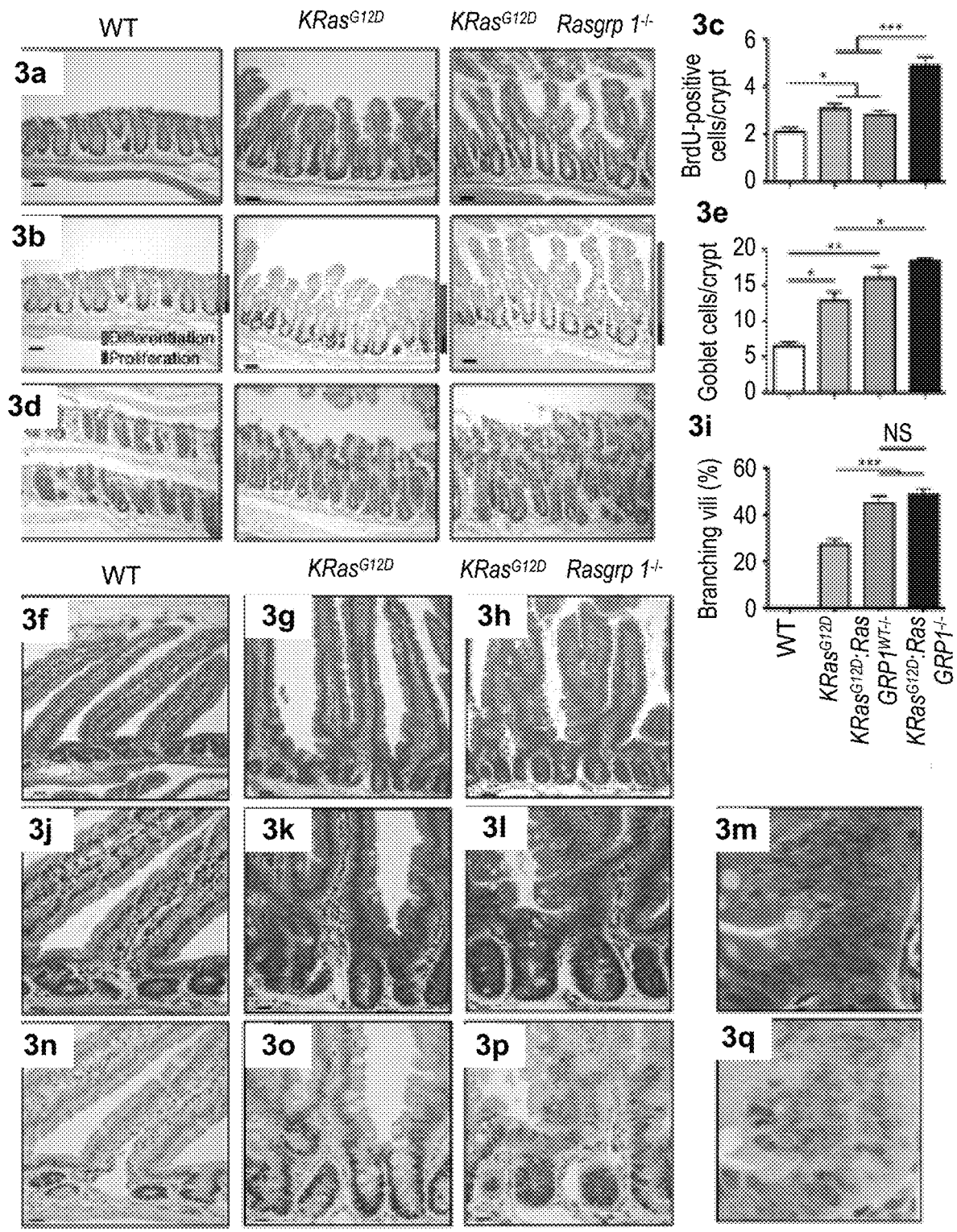
Figures 9A, 9B, 9C:
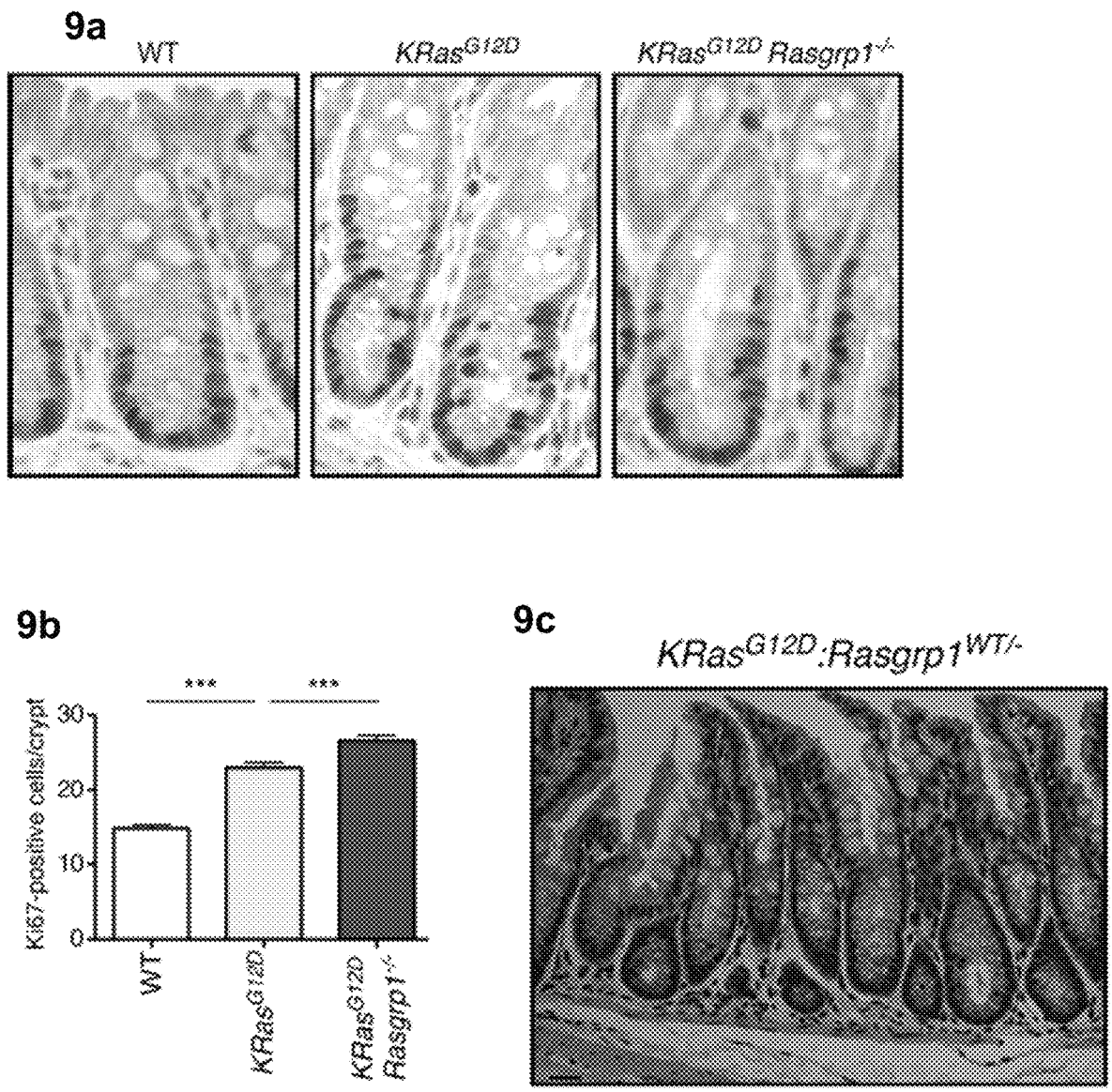
FIGS. 9a-9c show representative sections of colon with H&E (FIG. 9a) or Ki67 stainings (FIG. 9c), revealing the serrated dysplasia of the colonic epithelium in KRas$^{G12D}$ mice that is further exacerbated with loss of Rasgrp1.

In the normal colon, proliferation is confined to cells in the bottom of the crypt. KRas$^{G12D}$ mice displayed colonic crypt hyperplasia compared to wild type littermates with increased numbers of Ki67-positive cells further up in the differentiated zone and loss of Rasgrp1 in the context of KRas$^{G12D}$ resulted in further increases of Ki67-positive cells (FIGS. 3a, 3b, and Supplementary FIGS. 1a and 1b). Both KRas$^{G12D}$ and KRas$^{G12D}$ mice heterozygous for Rasgrp1 demonstrated increased proliferation of the colonic epithelium compared to wildtype control mice, measured via in vivo BrdU-labeling. Deletion of the second allele of Rasgrp1 resulted in a further augmentation of the KRas$_{G12D}$-induced proliferation (FIG. 3c). Serrated dysplasia is a notable feature of the KRas$^{G12D}$ mouse colon and is also seen in KRAS$^{MUT}$ human hyperplastic polyps[39-41] (FIGS. 3a, 3b, middle panels). Serrated polyps are now recognized as an important subcategory of hyperplastic polyps that provide a route to CRC that is to be distinguished from the progression of conventional adenomas to CRC[26]. At 6 months of age, we found that loss of either one or both Rasgrp1 alleles resulted in exacerbated serrated dysplasia, typified by further lengthening and increased serration of villi-like projections into the colonic lumen. These features were also accompanied by an increased abundance of goblet cells (FIGS. 3d, 3e, and 9c). The increased goblet cell presence and heavily serrated nature in these KRas$^{G12D}$Rasgrp1$^{WT/-}$ and KRas$^{G12D}$:Rasgrp1$^{-/-}$ mice share remarkable resemblance with human hyperplastic or serrated polyps of the goblet cell subtype[26].

Figure 10A:
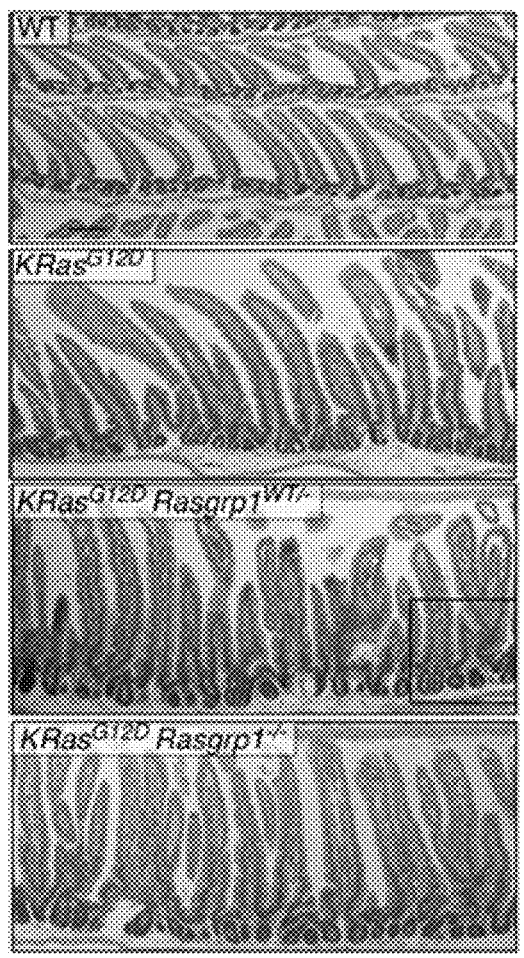
FIGS. 10a-10d show representative sections of colon with H&E (FIG. 10a) or Ki67 stainings (FIG. 10b), revealing different villi length for the different mouse genotypes. FIG.
Figure 10B:
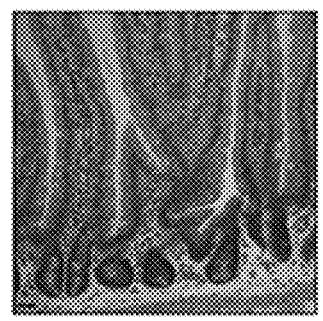
Figure 10C:
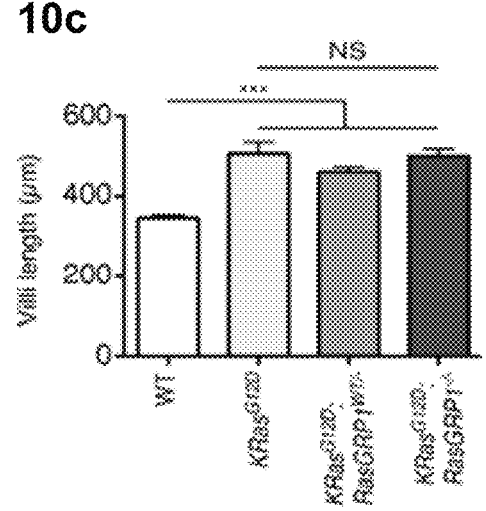
Figure 10D:
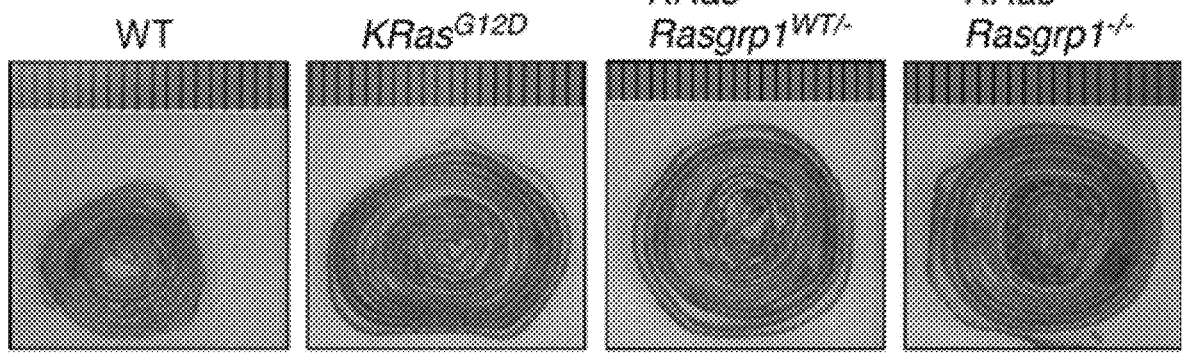
Figure 11A:
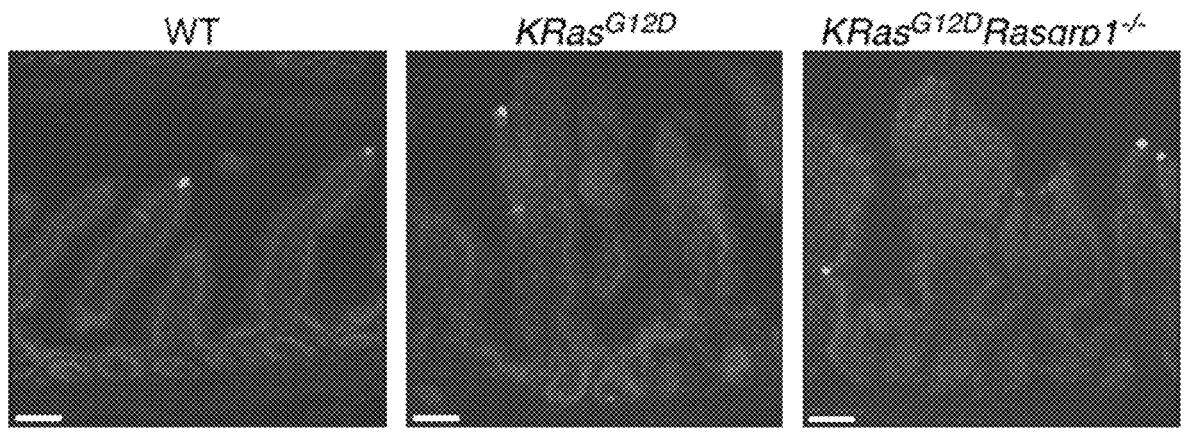
FIGS. 11a-11b show representative sections of colon with cleaved caspase-3 stainings (FIG. 11a) and quantification (FIG. 11b).
Figure 11B:
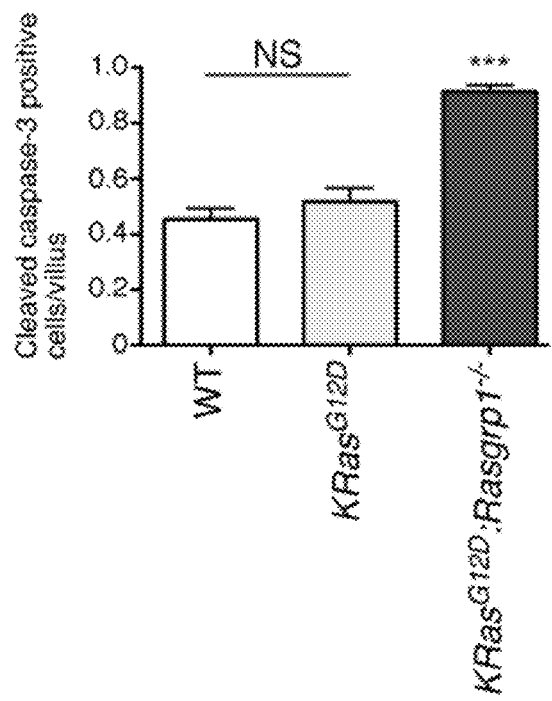
Figure 12A:
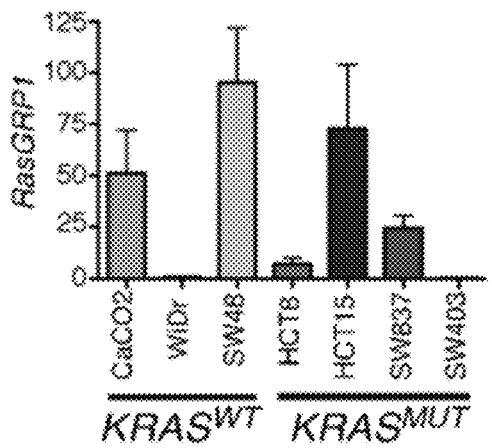
FIGS. 12a-12e provides expression data in seven CRC lines that represent each of the significant genotypes in Table 1. The expression of RasGRP1 (FIGS. 12a and 12b), Ras-GRP2 (FIG. 12c), RasGRP3 (FIG. 12d), and RasGRP4 (FIG. 12e) were measured in the cell lines.
Figure 12B:
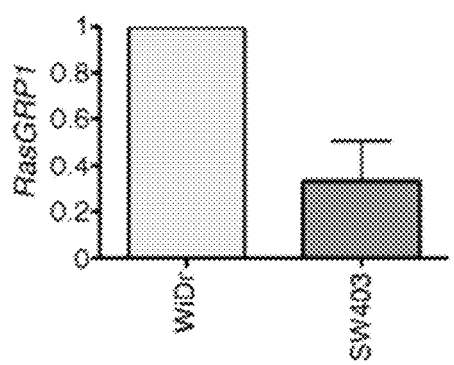
Figure 12C:
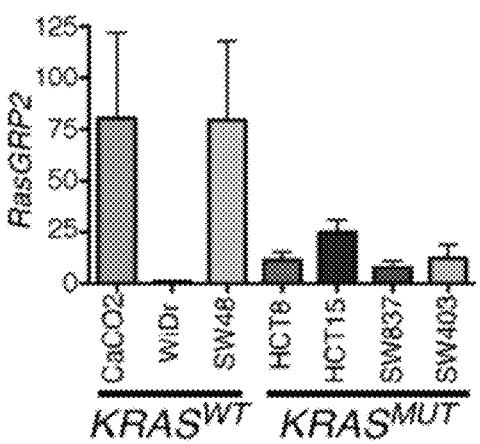
Figure 12D:
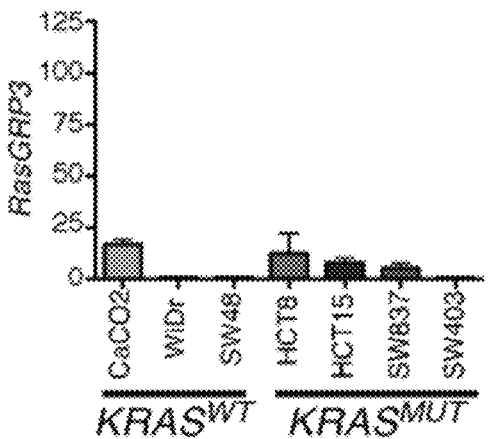
Figure 12E:
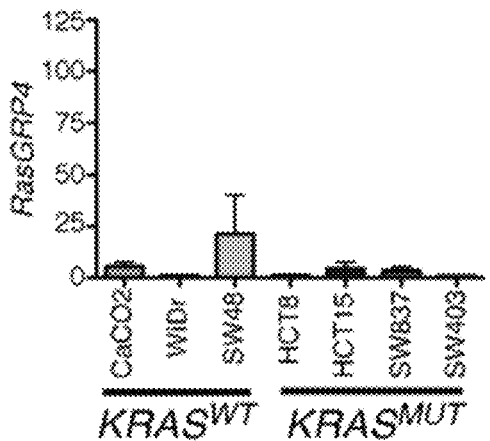
Figure 13A:
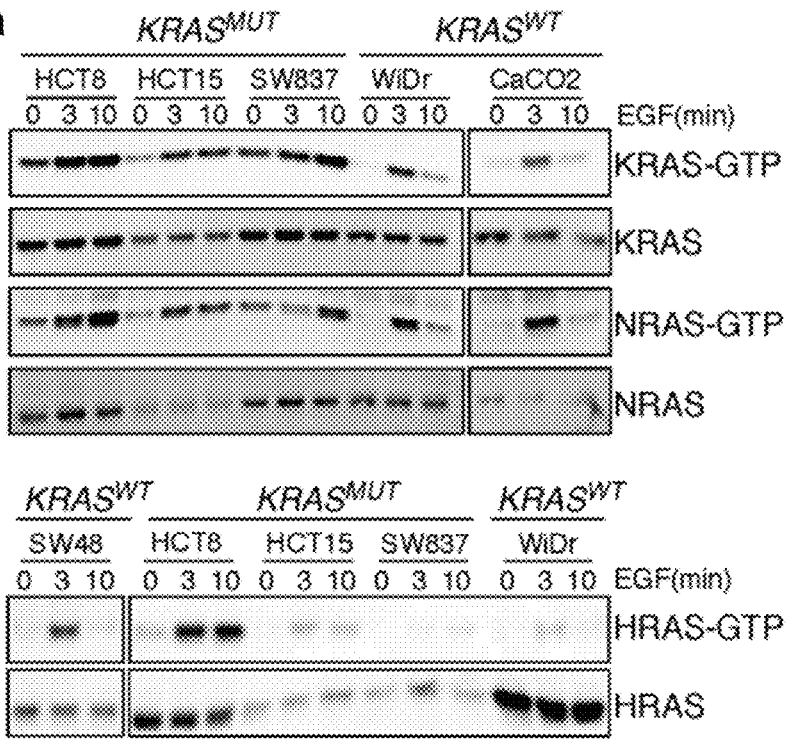
FIGS. 13a-13e show N-RAS and H-RAS activation upon EGF induction in different colorectal cancer (CRC) cell lines by western blotting of pull down assays.
Figure 13B:
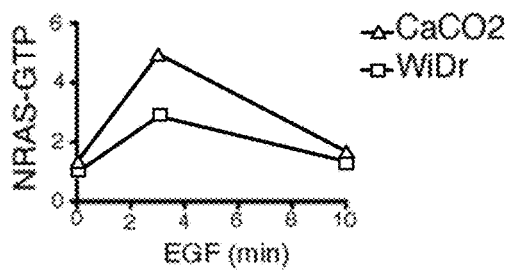
Figure 13C:
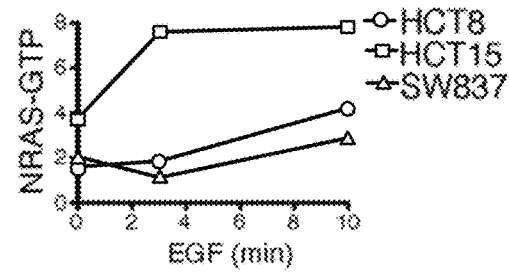
Figure 13D:
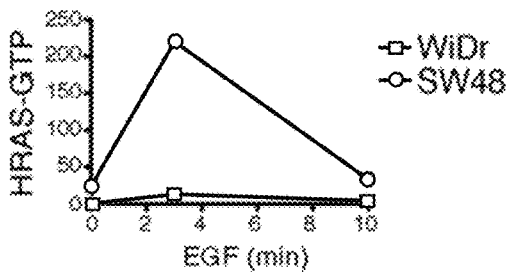
Figure 13E:
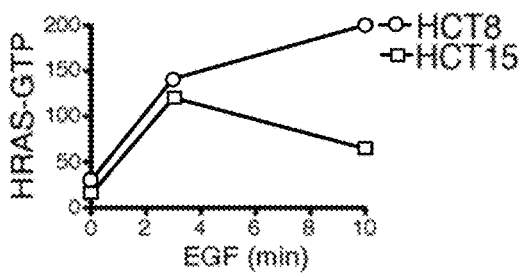
Figure 14A:
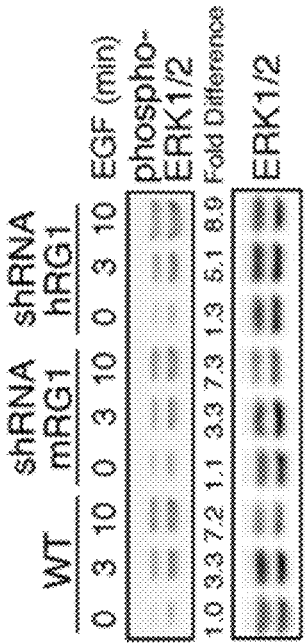
FIGS. 14a-14b show sustained ERK phosphorylation in RasGRP1 knockdown cells.
Figure 14B:
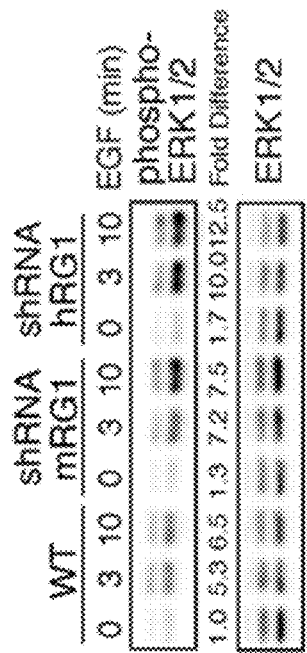

In the normal small intestine, proliferation mainly takes place in the crypt and T/A zone, which is only one epithelial cell layer thick[33] and is the site of EGFR signalling[24]. Depletion of Rasgrp1 resulted in three distinct cell biological abnormalities in the context of KRas$^{G12D}$. First, compared to WT controls, villi of KRas$^{G12D}$ small intestine were longer and had a branched appearance in 20% of the cases, as has been suggested previously[41]. Deletion of one or two Rasgrp1 alleles resulted in a profound branching of the villi (FIG. 3f-3i and 10a-10b). As reported[41,] we also observed increases in crypt fissions in KRas$^{G12D}$ small intestine, but did not observe overt changes upon loss of Rasgrp1 (data not shown). Second, expression of KRas$^{G12D}$ resulted in thickening and increase cellularity of the T/A zone, accompanied by an expansion of Ki67-positive cells higher up on the crypt-villus axis (FIGS. 3j, k, n, o). Deletion of Rasgrp1 exacerbated this feature of the KRas$^{G12D}$ phenotype substantially; we observed 15 to 20 cell-wide T/A zones of pseudo-stratified cells that stained positive for Ki67 and displayed heterochromatin features (FIGS. 3l, m, p, q). These characteristics are indicative of active cell division and are used to type dysplastic tissues from patients[26]. Third, despite these increases in proliferation, complete deletion of Rasgrp1 did not trigger a further lengthening of the already elongated KRas$^{G12D}$ villi nor did it lead to an overall increase in length of the intestinal track (FIGS. 10c-10d). Instead, we observed increased levels of cleaved caspase-3 when Rasgrp1 is deleted in the context of KRas$^{G12D}$ (FIGS. 11a-11b). As previously reported[41], we did not see differences in apoptosis between KRas$^{G12D}$ and WT small intestines.

In summary, deletion of Rasgrp1 increased proliferation in the context of KRas$^{G12D}$ and exacerbated the dysplasia, but also resulted in elevated levels of cell apoptosis (FIGS. 3 and 9a-9c, 10a-10d, and 11a-11b).

EGFR-RasGRP1 and EGFR-SOS1 Signals in Epithelial Cells

The genetic studies above reveal that Rasgrp1 restricts the dysplastic effects of KRas$^{G12D}$ in the intestinal epithelium. To investigate the underlying mechanism, we first established the presence of the RasGRP1 protein in 16 of 18 human CRC cell lines and found that the EGFR is also commonly expressed in these CRC lines (FIG. 4a). Eleven of eighteen CRC cell lines carried the stereotypic KRAS$^{MUT}$ found in patients[15].

In stimulated lymphocytes, the GEF activity of RasGRP1 is enhanced via PKC-dependent phosphorylation of threonine 184[5]. We used the earlier-mentioned DT40 cell system to demonstrate that phospho-T$_{184}$-RasGRP1 levels were induced upon B cell receptor-but also EGFR-stimulation in a RasGRP- and PKC-dependent manner (FIG. 4b). We subsequently immunoprecipitated RasGRP1 from KRAS$^{WT}$ SW48 and KRAS$^{MUT}$ HCT15 CRC cells, two lines of similar stage (Dukes' type C colorectal adenocarcinoma, ATCC information) that behave predictable in tissue culture and xenograft assays. We found that EGF transiently elevated the phosphorylation of RasGRP1 in both cell types (FIG. 4c). SOS1, pre-complexed with Grb2, is recruited to phosphorylated tyrosine 1068 in the EGFR[43] and is subsequently subject to feedback mechanisms that include EGF-induced phosphorylation[44, 45]. Consequently, and as anticipated, EGFR stimulation induced a mobility shift of SOS1 in HCT15 and SW48 cells (FIG. 4d). To investigate the RAF-MEK-ERK effectors pathway downstream of RasGTP, we examined ERK phosphorylation and noted that both cell lines display EGF-induced activation of ERK kinases (FIG. 4e). RasGRP1 and SOS1 are likely to both play a role in CRC cells with either a KRAS$^{MUT}$ or a KRAS$^{WT}$ allele, since both RasGEFs are phosphorylated in both in HCT15 and SW48 cells response to EGF signal input (FIG. 4f).

KRAr$^{MUT}$ CRC cell lines demonstrate EGFR-induced hyperactivation of RAS.

To investigate the mechanistic underpinnings of Ras-GRP1, SOS1, and KRAS$^{MUT}$ in the cellular response to signalling through the EGFR, we selected seven CRC lines that represent each significant genotype (Table 1). We first established that expression of RasGRP1 in these cells is specific and selective; thus these cell lines express essentially no RasGRP3 or RasGRP4. RasGRP2, while expressed e.g. in CaCO2 and SW48 (FIGS. 12a-12e), is an exchange factor for the small GTPase Rap[5, 46].

TABLE 1

RasGRP1 expression profile and KRAS mutational status in selected colorectal cancer cell lines.

| Colorectal cancer cell lines | RasGRP1 | KRAS Allele 1 | Allele 2 | Other mutations in RAS pathway |
|---|---|---|---|---|
| CaCO2 | + | WT | WT | None |
| WiDr | + | WT | WT | BRAF$^{V600E}$ |
| SW48 | + | WT | WT | EGFR$^{G719S}$ |
| HCT8 | + | G12V | WT | None |
| HCT15 | + | G13D | WT | None |
| SW837 | + | G12C | WT | None |
| SW403 | − | G12V | WT | None |

(+) presence of RASGRP1,
(−) absence of RasGRP1.

Figure 5A:
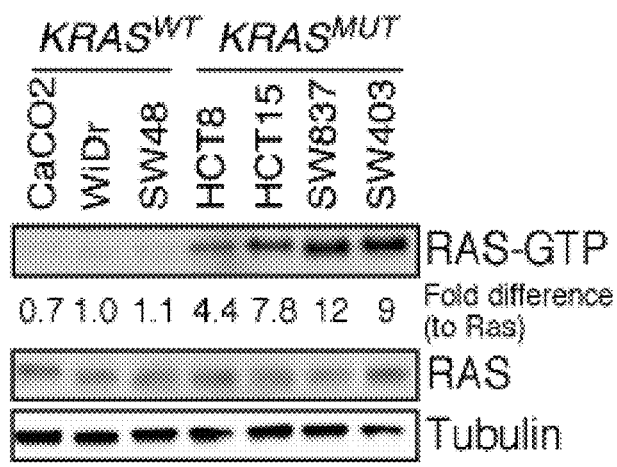
FIGS. 5a-5d illustrate that hyperactivation of RAS in EGF-stimulated KRASMUT CRC cells. Total baseline RAS-GTP levels in serum-starved CRC cells reveals elevated levels in CRC cell lines with KRAS$^{MUT}$ (FIG. 5a). Levels are normalized to RAS and arbitrarily set at 1.0 in WiDr cells. KRAS-GTP profile of time courses with EGF-stimulated (5 ng/ml) KRAS wild type cells (KRAS$^{WT}$) (FIG. 5b) and KRAS mutant cells (KRAS$^{MUT}$) (FIG. 5c). Results in FIGS. 5a-c are representative of three or more independent experiments. Cartoon of Grb2/SOS1 recruitment to tyrosine-phosphorylated EGFR and allosteric activation of SOS1 through a positive feedback loop by Ras-GTP (FIG. 5d).
Figure 5B:
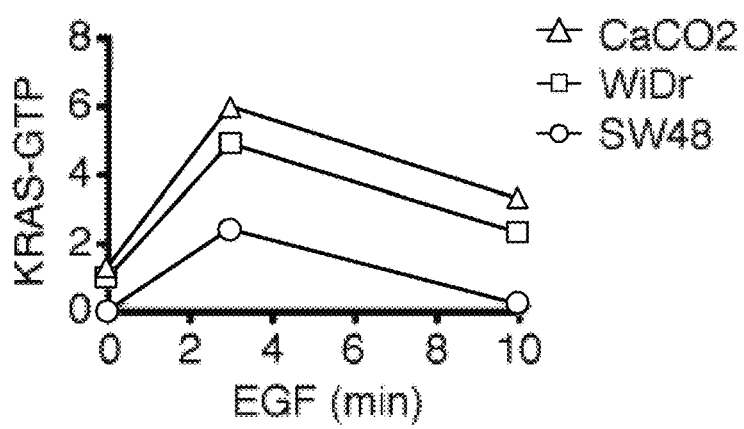
Figure 5C:
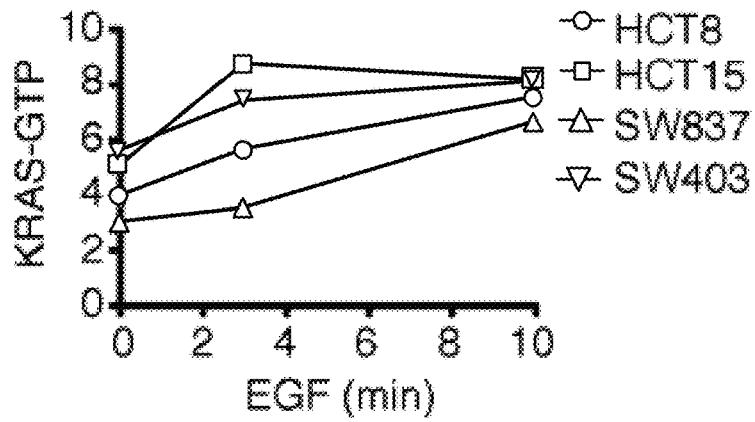

As expected from the impaired RasGAP-mediated inactivation of KRAS$^{MUT}$ [1, 12, 13], the four colorectal cancer lines carrying KRAS$^{MUT}$ alleles expressed elevated constitutive RAS-GTP levels compared to CaCO2, WiDr, and SW48 cells with KRAS$^{WT}$ (FIG. 5a). The otherwise low baseline KRAS-GTP levels were efficiently, but only transiently, induced by EGF stimulation of KRAS$^{WT}$ cell lines (FIG. 5b). Significantly, the elevated constitutive KRAS-GTP levels in KRAS$^{MUT}$ colorectal cancer cells were further increased by stimulation with EGF (FIG. 5c). This latter observation, combined with our data in FIG. 4, suggests that the EGFR acts through RasGEFs to provide further exchange factor input to hyperactivate KRAS in KRAS$^{MUT}$ cells. Moreover, EGF also induced sustained activation of N- and H-RAS in KRAS$^{MUT}$ cells, whereas EGF only transiently augmented the levels of N- and H-RAS-GTP in KRAS$^{WT}$ cells (FIGS. 13a-13e).

Figure 5D:
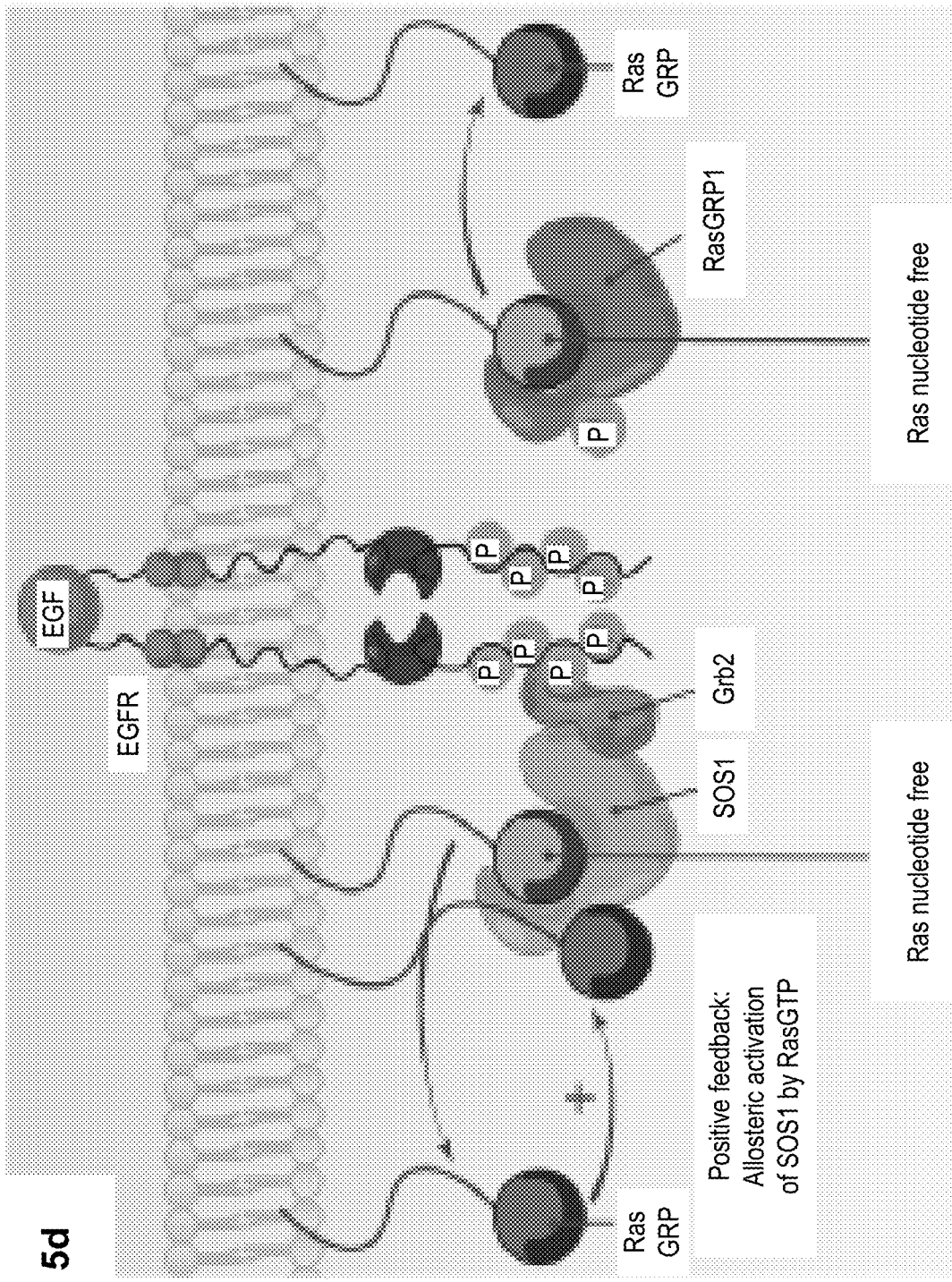

Binding of Ras-GTP to an allosteric pocket in SOS greatly enhances the RasGEF activity of SOS[9] and in cells this creates a positive feedback loop of Ras-GTP/SOS/Ras-GTP[4, 10, 11] (FIG. 5d). Recent work revealed allosteric priming of SOS1 in cancer cells; in unstimulated PDAC cell lines, KRAS$^{MUT}$ primes SOS and results in elevated constitutive levels of HRAS-GTP[47]. Here, our RAS-GTP pull down experiments demonstrated that EGF stimulation induces sustained N- and H-RAS activation as well as K-RAS hyperactivation in KRAS$^{MUT}$ CRC cells. This is in marked contrast with the transient activation of N-, H- and K-RAS in KRAS$^{WT}$ cells. Therefore, allosteric SOS1 activation by KRAS$^{MUT}$ may also play a role in cancer cells under condition of EGF stimulation (FIG. 5d). Together, these observations led us to next explore how SOS1 and RasGRP1 shape the character of EGFR-Ras signals and impact cell biology in the context of KRAS$^{MUT}$.

SOS1 Promotes EGF-Induced KRAS Activation and Growth of KRAS$^{MUT}$ CRC Cells

Figures 6A, 6B, 6C, 6D, 6E:
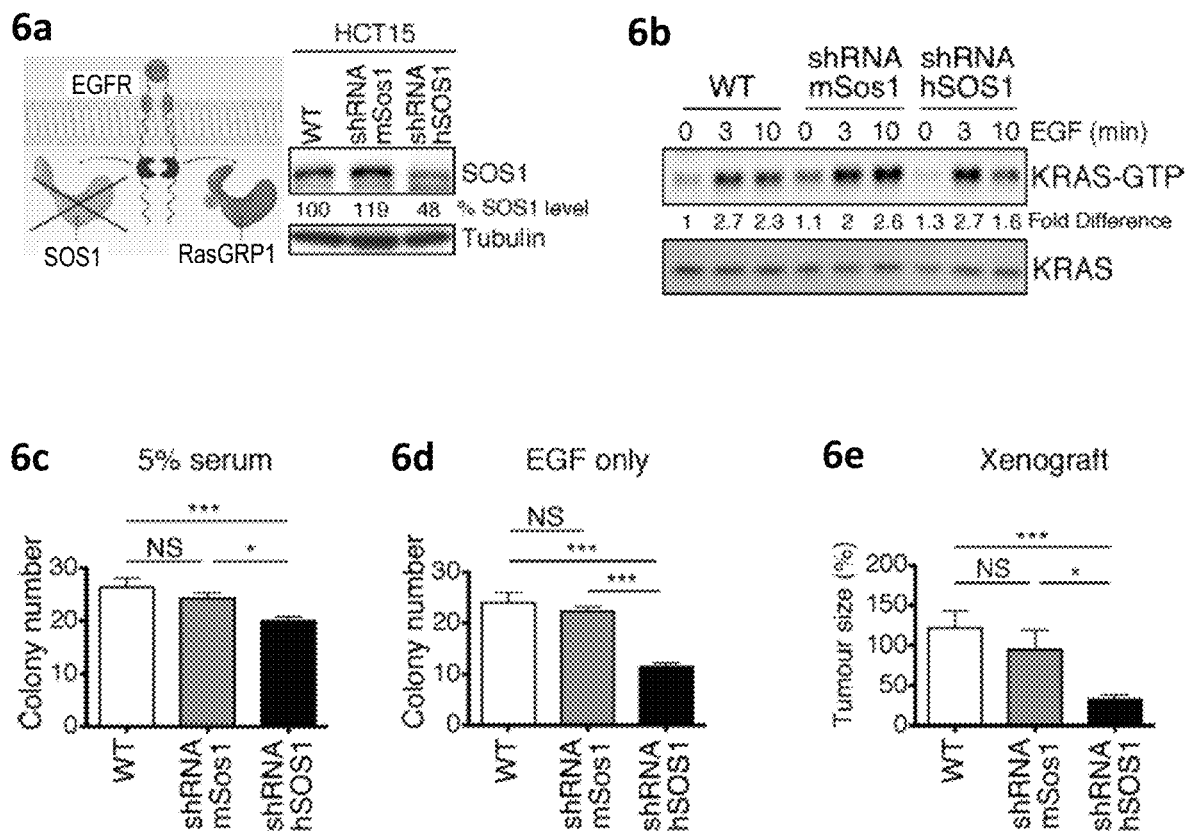
FIGS. 6a-6e illustrate that EGFR-SOS1 signals promote EGFR-Ras signalling and tumorigenesis of KRAS$^{MUT}$ CRC cells. Detection of SOS1 expression in HCT15 cells with knockdown for human SOS1 (shRNAhSOS1) (FIG. 6a). shRNA for murine Sos1 (shRNAmSOS1) is used as specificity control. Detection of KRAS-GTP in the indicated EGF-stimulated (5 ng/ml) HCT15 cell populations (FIG. 6b). KRAS-GTP levels are quantitated and corrected for by total KRAS levels. Unstimulated WT HCT15 cells are arbitrarily set at 1.0. Representative results of four independent experiments. Soft-agar colony formation assays of the indicated HCT15 cell populations that were grown in growth medium with 5% serum (FIG. 6c) or in serum-free medium supplemented with 10 ng/ml EGF (FIG. 6d). Relative tumor size of the indicated HCT15 cells xenografted into nude mice and measured 40 days after injection (5 mice/group) (FIG. 5e).

To investigate the role of SOS1 downstream of the EGFR in the context of a KRAS$^{MUT}$ allele, we reduced human SOS1 expression in HCT15 CRC cells, which respond to EGF but are insensitive to the EGFR inhibitor Erlotinib (FIG. 6a and Table 2). Reduction of SOS1 expression resulted in less sustained KRAS activation following EGF stimulation, compared to parental HCT15 cells or to HCT15 cells treated with a control shRNA (against murine Sos1) (FIG. 6b). The impaired KRAS activation in cells with a 52% reduction in SOS1 was accompanied by diminished in vitro colony formation, particularly noticeable when EGF was used as the exclusive growth factor (FIGS. 6c and 6d). The effect of reduced SOS1 expression on in vivo tumorigenesis was similarly apparent; the average tumor size of subcutaneously xenografted cells decreased four-fold (FIG. 6e). These results demonstrate that EGFR-SOS1-Ras signals contribute to tumorigenesis when CRC cells carry a KRAS$^{MUT}$ allele.

TABLE 2

Sensitivity of colorectal cancer cell lines to the Erlotinib EGFR inhibitor.

| Colorectal cancer cell lines | Erlotinib EC$_{50}$ (μM) |
|---|---|
| COLO205 | 0.03 |
| SNU-C2A | 0.19 |
| COLO-678 | 0.19 |
| CCK-81 | 0.38 |
| HCC-56 | 0.46 |
| NCI-H747 | 0.52 |
| C2BBe1 | 0.56 |
| SW403 | 0.81 |
| LS123 | 0.81 |
| SKCO1 | 2.24 |
| COLO320 | 2.29 |
| RKO | 5.93 |
| SW48 | 7.36 |
| HCT15 | 8.16 |
| JURKAT | 8.33 |

Figures 7A, 7B, 7C, 7D:
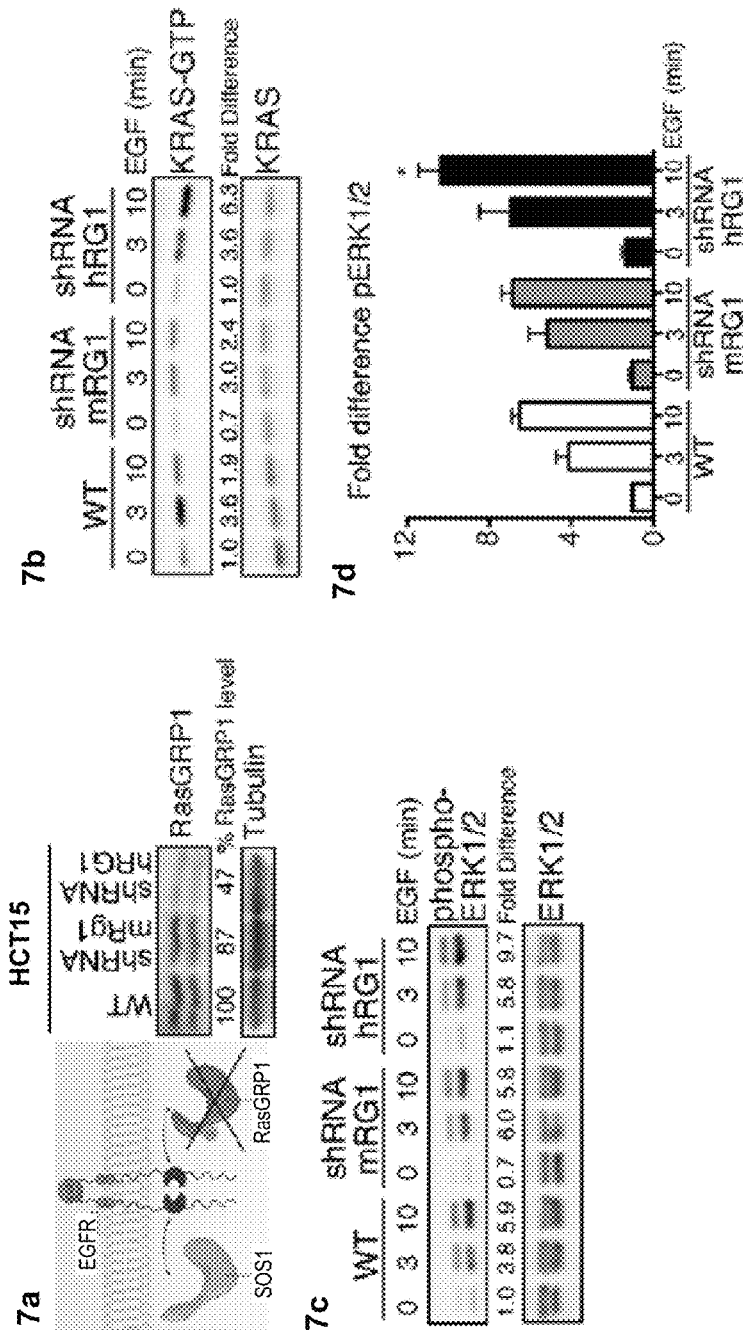
FIGS. 7a-7i show that RasGRP1 feedback restricts EGFR-SOS1-Ras signals. Detection of RasGRP1 expression in KRAS' HCT15 cells analogous to FIG. 6a (FIG. 7a). Knockdown for murine Rasgrp1 (shRNAmRg1) functions as control. KRAS-GTP levels in the indicated EGF-stimulated (5 ng/ml) HCT15 cell populations (FIG. 7b). Note the increase KRAS-GTP levels at the 10-minute time point when RasGRP1 expression levels are reduced. Analysis of ERK phosphorylation and total ERK protein levels in the same cell lysates presented in FIG. 7b (FIG. 7c). Unstimulated WT HCT15 cells are arbitrarily set at 1.0. Quantification of ERK phosphorylation from FIG. 7c and two independent experiments (FIGS. 14a and 14b) (FIG. 7d). Averages in fold difference±s.e.m are depicted. *p<0.05 comparing the 10-minue time point of shRNAhRG1 to that for WT and shRNAmRG1. Analysis of EGFR phosphorylation in WCL of EGF-stimulated (25 ng/ml) cells (FIG. 7e). Analysis of EGF-induced complexes of Grb2/SOS1 with P-Y$_{1068}$-EGFR (FIG. 7f). SOS1 was immunoprecipitated (SOS1 IP) from the indicated HCT15 cells and IP's were blotted with specific antibodies against the indicated proteins. Note the increased levels of P-Y$_{1068}$-EGFR that IP with SOS1 in an EGF-stimulatory dependent manner when RasGRP1 levels are reduced. Analysis of P-Y$_{1068}$-EGFR in the indicated EGF-stimulated HCT15 populations as in FIG. 7e (FIG. 7g). Cells were treated with R59949 DGK inhibitor to enhance DAG-RasGRP1 signalling or with DMSO as control. R59949 exposure results in decreased levels of P-Y$_{1068}$-EGFR. All panels in FIG. 7 are representative examples of three or more independent experiments. Immunohistochemical analysis of ERK phosphorylation levels in brown staining in the colonic epithelium of the indicated mouse genotypes (FIG. 7h). Images of distal colonic epithelium are representative results of two mice per genotype. Analysis of ERK phosphorylation and total ERK protein level of mouse intestinal epithelial cells (IEC) isolated from colon of control WT-, KRas$^{G12D}$-, KRas$^{G12D}$Rasgrp1$^{WT/-}$-mice (6 month-old) (FIG. 7i). Blots show three independent experiments. P-ERK in IEC from WT mice is arbitrarily set at 1.0 for each experiment.

RasGRP1 Restricts EGF-SOS1 Induced KRAS-ERK Signalling Through Negative Feedback RasGRP1 is structurally distinct from SOS1 and possesses 1000-fold lower intrinsic RasGEF activity than SOS1[25]. Moreover, RasGRP1 is not activated allosterically by RAS-GTP[25] but is recruited to the membrane by diacylglycerol[5]. We postulated that reduction of RasGRP1 expression via shRNA could affect HCT15 cells differently than depletion of SOS1 (FIG. 7a). In contrast to the effects of SOS1, 53% reduction of RasGRP1 from HCT15 cells resulted in increased EGFR-driven hyperactivation of KRAS (FIG. 7b), which translated in sustained ERK phosphorylation downstream of RasGTP (FIGS. 7c, 7d, 14a and 14b).

Figures 7E, 7F, 7G:
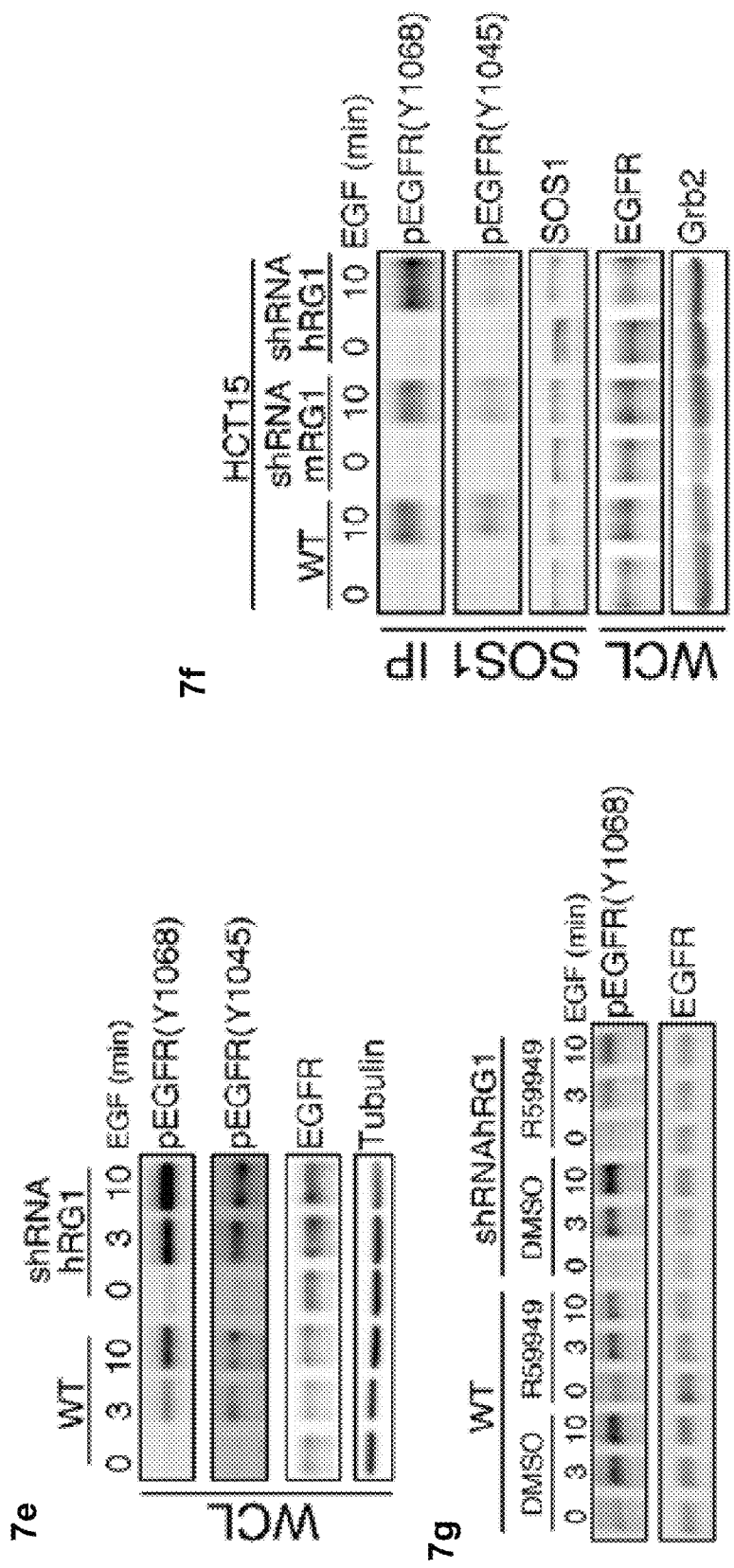

We subsequently investigated if RasGRP1 may impact SOS1. We examined levels of P-Y$_{1068}$-EGFR (phosphotyrosine 1068 in the EGFR) a major auto-phosphorylation site[48] to which Grb2-SOS1 is recruited[43] when cells are stimulated with EGF (FIG. 5d). Reduction of RasGRP1 expression significantly and selectively increased P-Y$_{1068}$-EGFR levels (FIG. 7e) and increased P-Y$_{1068}$-EGFR levels complexed to SOS1-Grb2 (FIG. 7f). Conversely, enhancing diacylglycerol-RasGRP1 signalling in EGF-stimulated HCT15 cells via exposure to an inhibitor of the diacyglycerol-converting enzyme DGK (diacylglycerol kinase)[49] resulted in reduced P-Y$_{1068}$-EGFR levels (FIG. 7g). Thus, diacylglycerol-RasGRP1 signalling constitutes a negative feedback loop to limit P-Y$_{1068}$-EGFR-Grb2/SOS-RAS-ERK signals.

Figure 7H:
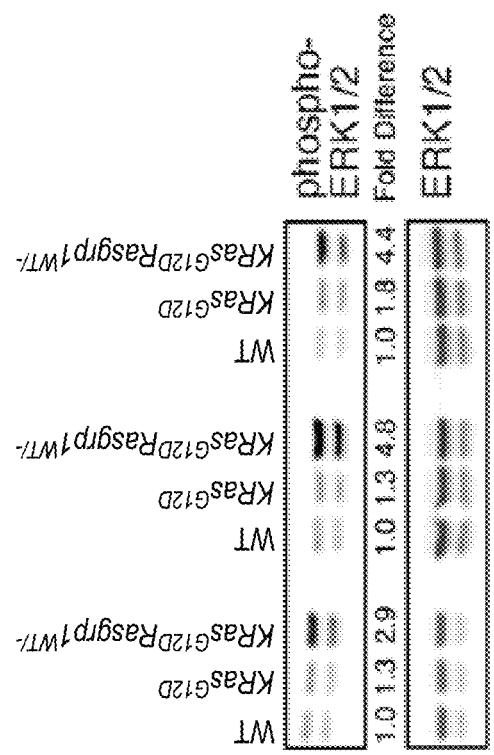
Figure 7I:
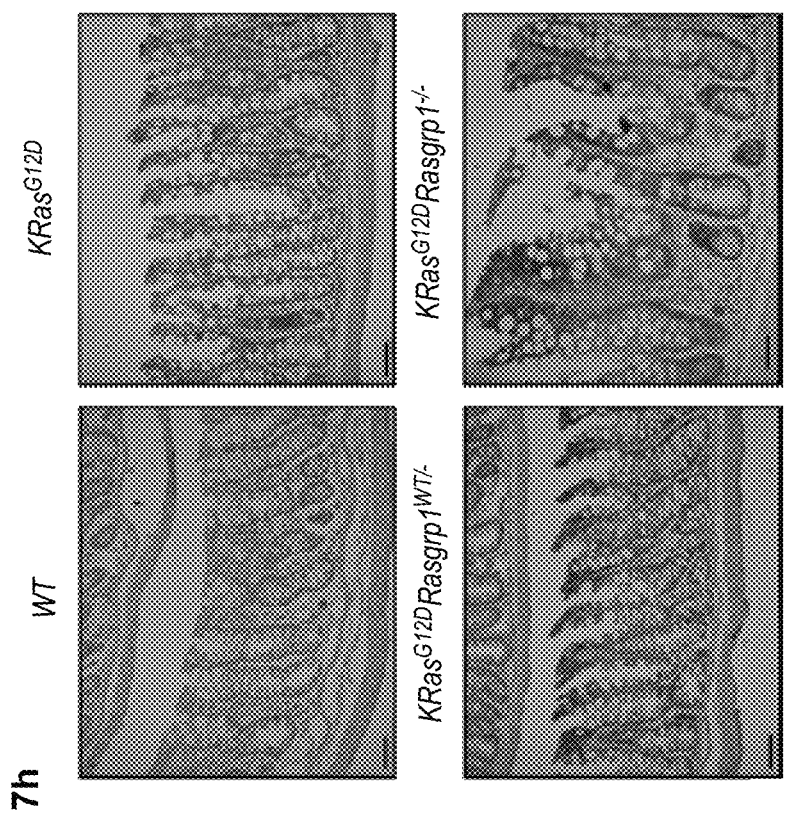

Having established the existence of this RasGRP1-dependent negative feedback loop, we next went back to the colonic epithelium of our mouse models with the different genetic perturbations. Analogous to our findings in the human CRC HCT15 cell line, we observed that deletion of one or two alleles of Rasgrp1 in the context of KRasG12D substantially increased the relative staining for phosphorylated ERK kinases in sections of colonic epithelium (FIG. 7h). Furthermore, direct, side-by-side comparisons of isolated epithelial cells confirmed the increased ERK phosphorylation in KRasG12D colonic epithelial cells when Rasgrp1 levels are reduced (FIG. 7i).

RasGRP1 Expression Levels Limit Growth of KRA$^{MUT}$ CRC Cells.

Figures 8A, 8B, 8C:
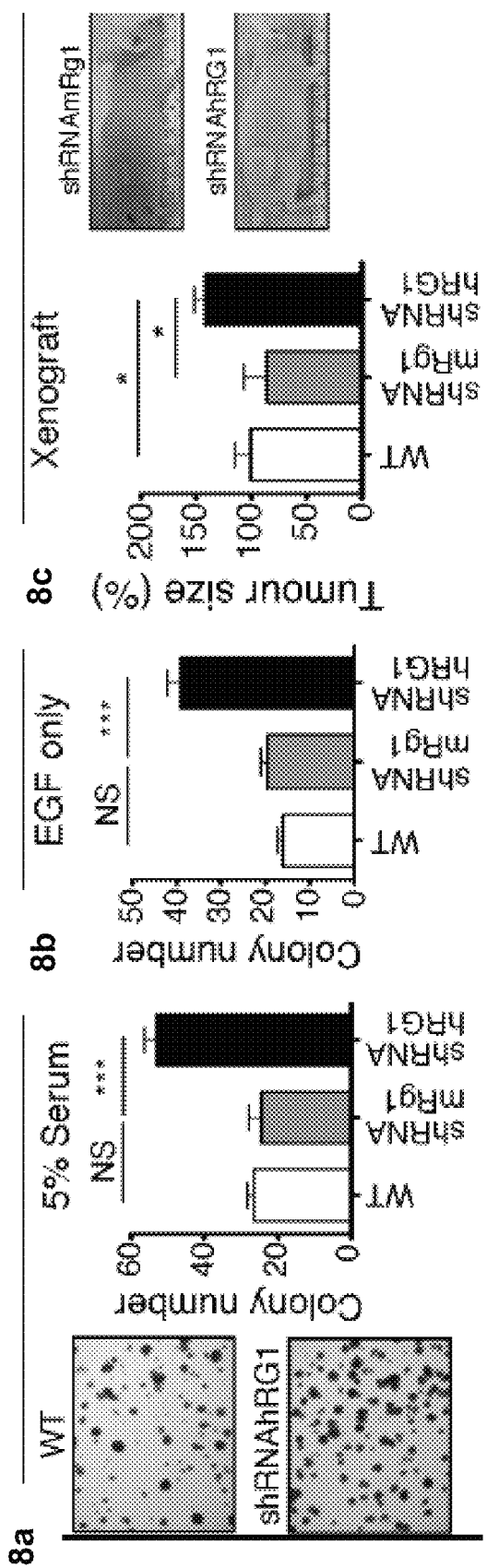
FIGS. 8a-8j show that RasGRP1 limits CRC cell proliferation and in vivo tumor growth. Soft-agar colony formation assays analogous to the ones presented in FIGS. 6c and d but now analyzing RasGRP1 function (FIGS. 8a and 8b). Reduction of RasGRP1 expression by 53% results in increased growth under both indicated growth conditions. Averages with standard errors are depicted; NS=not significant, *** p<0.0001 (One-way ANOVA). Relative tumor size of the indicated HCT15 cells xenografted into nude mice and measured 40 days after injection (5 mice/group) (FIG. 8c). HCT15 cells with reduced RasGRP1 levels result in statistically significant larger tumors compared to the WT and the mouse Rasgrp1 shRNA controls. * p<0.05. Growth rates of the indicated xenografted HCT15 cells (FIG. 8d). Specifics of HCT15 cells with shRNAhSOS1 are inserted in blue for comparison. Kaplan-Meier survival curve from 172 humans patient samples showing correlation between RasGRP1 expression level and clinical patients survival in GSE17536 (FIG. 8e). High RasGRP1 expression level (red line) (n=155) correlates with better prognosis than low RasGRP1 expression level (blue line) (n=17) (p=0.0243). Kaplan-Meier survival curve showing decreased survival of Apc$^{Min/+}$ mice deleted for Rasgrp1 (n=20) compared to Apc$^{Min/+}$ mice (n=12) (FIG. 8f). * p<0.0006, Log-rank (Mantel-Cox) Test. Representative image of a Apc$^{Min/+}$: Rasgrp1$^{-/-}$ colon with tumors in the distal portion (FIG. 8g). Quantification of colonic tumor incidence in Apc$^{Min/+}$ and Apc$^{Min/+}$:Rasgrp1$^{-/-}$ mice (n=16 and 19, respectively) (FIG. 8h). p<0.01 (unpaired t-test). Bar graph analysis of colonic tumor sizes for Apc$^{Min/+}$ and Apc$^{Min/+}$:Rasgrp1$^{-/-}$ mice (FIG. 8i). Analysis of ERK phosphorylation and total ERK protein levels of normal colon and colonic tumors of individual Apc$^{Min/+}$ and Apc$^{Min/+}$:Rasgrp1$^{-/-}$ mice (3-6 month-old) (FIG. 8j).
Figures 8D, 8E, 8F, 8G:
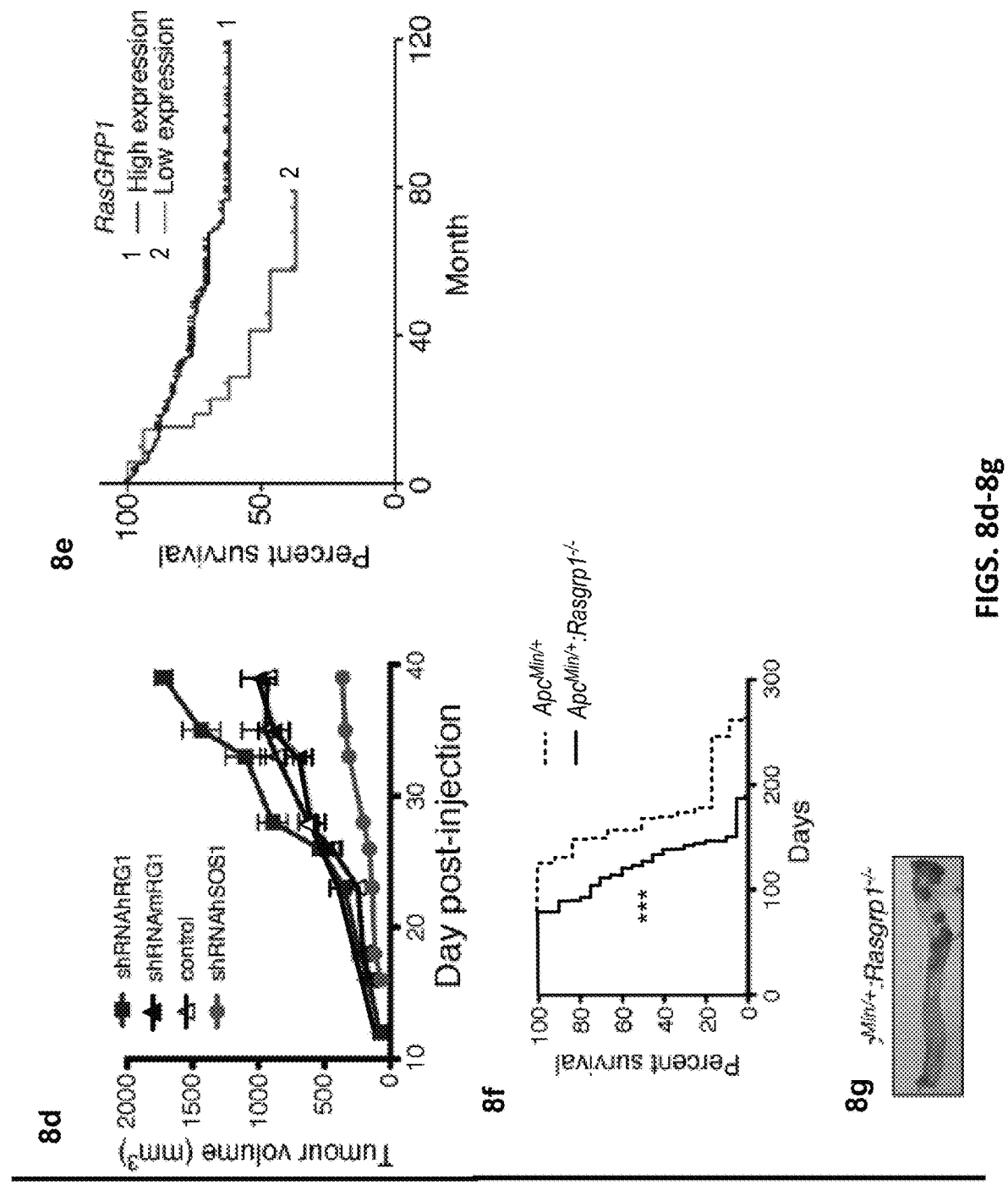

To further test the cell biological impact of decreasing Rasgrp1's negative feedback on EGFR-SOS1-RAS signalling, we examined colony formation and xenografted tumors. Reduction of RasGRP1 expression led to increased colony formation of HCT15 CRC cells in vitro, induced by either serum or by EGF (FIGS. 8a and 8b). The reduced expression levels of RasGRP1 elicited increased size and enhanced growth rate of xenograft tumors, compared to the parental HCT15 cells or HCT15 cells with a mouse Rasgrp1 shRNA construct as specificity controls; the exact opposite result obtained with HCT15 cells carrying SOS1 shRNA (FIGS. 8c and 8d). Thus, in contrast to the capacity of SOS1 to enable EGFR-RAS signalling and CRC cell growth, diacylglycerol-RasGRP1 signalling constitutes a negative feedback loop that limits EGFR-SOS-RAS signalling and has a growth suppressive role.

Figure 15A:
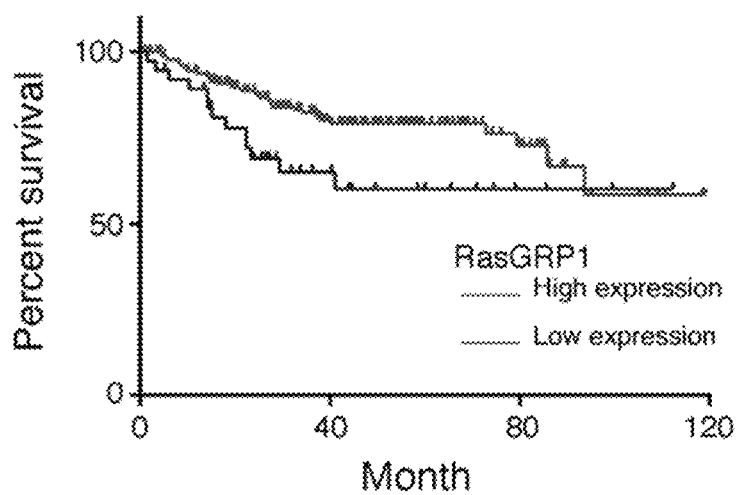
FIGS. 15a-15b show Kaplan-Meier survival curves from human patient samples showing correlation between Ras-GRP1 expression level and clinical patients survival in GSE12945 (FIG. 15a) and GSE14333 (FIG. 15a).
Figure 15B:
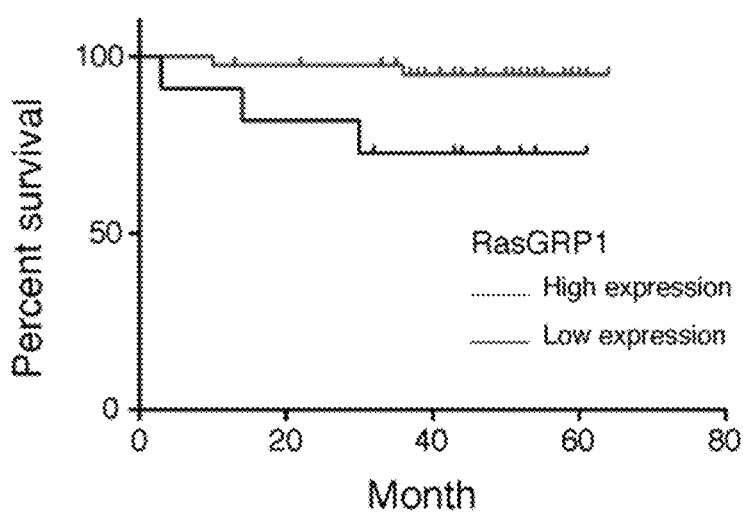

To investigate if levels of RasGRP1 in CRC impact patients clinically, we explored three published gene expression studies linked to clinical outcome of CRC patients (GSE17536[50]; GSE12945[51]; GSE14333[52]). We applied an established cut-off finder[53] to divide CRC patients from these studies in two groups based on RasGRP1 expression. We observed that high expression of RasGRP1 correlates with a better clinical outcome in all three studies (FIGS. 8e, 15a and 15b). CRC from patients in these studies do not all contain KRAS$^{MUT}$ and low RasGRP1 levels may therefore also lead to worse clinical outcome of CRC cause by other (non-KRAS$^{MUT}$) genetic lesions. To test this possibility, we next explored the Apc$^{Min/+}$ mouse model (APC=Adenomatous Polyposis Coli) with aberrant Wnt signalling[54] that is widely used to model human CRC[55-57].

RasGRP1 Suppresses Proliferative ERK Signalling in the Context of Aberrant Wnt Signalling.

Figures 8H, 8I, 8J:
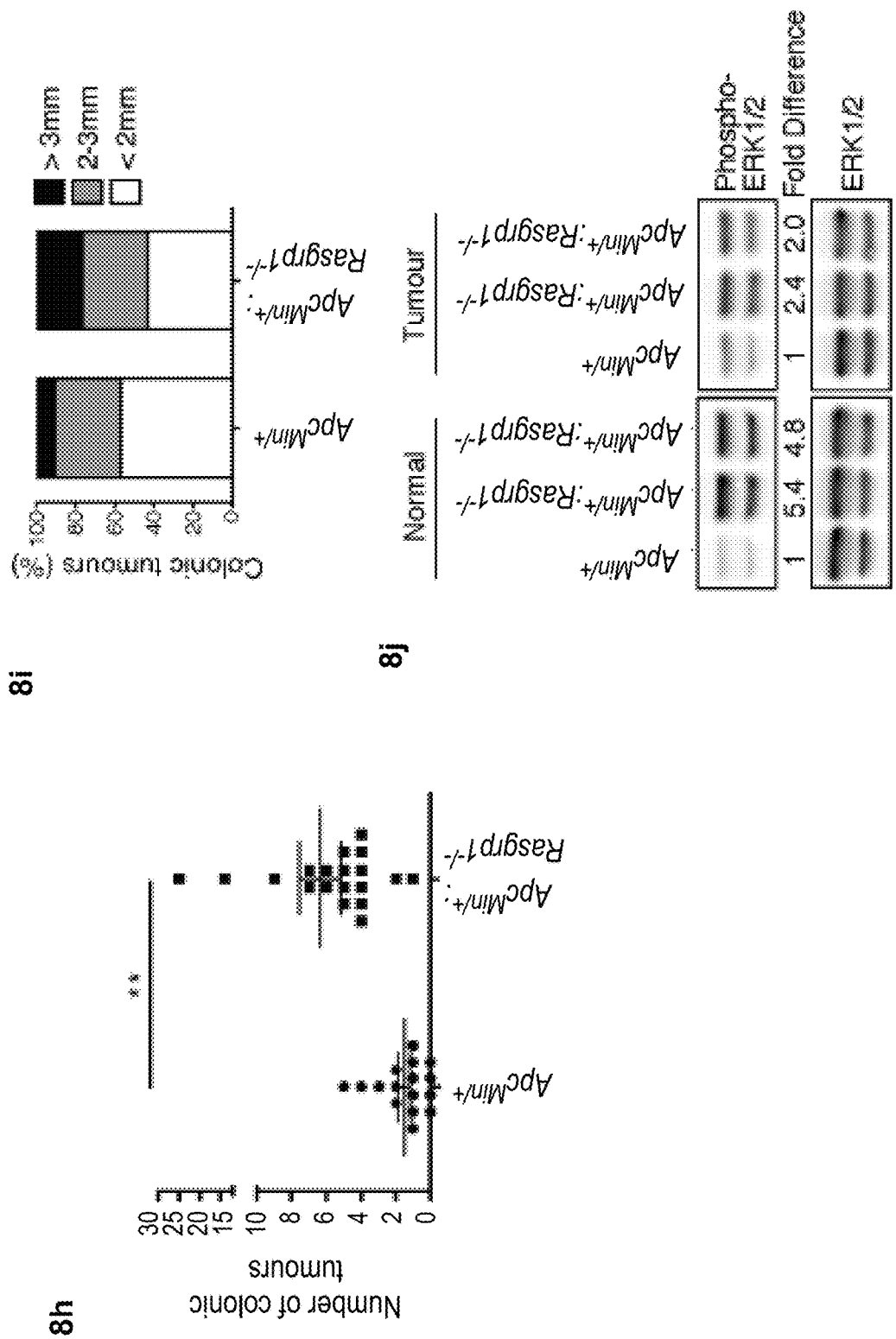
Figures 16A, 16B, 16C:
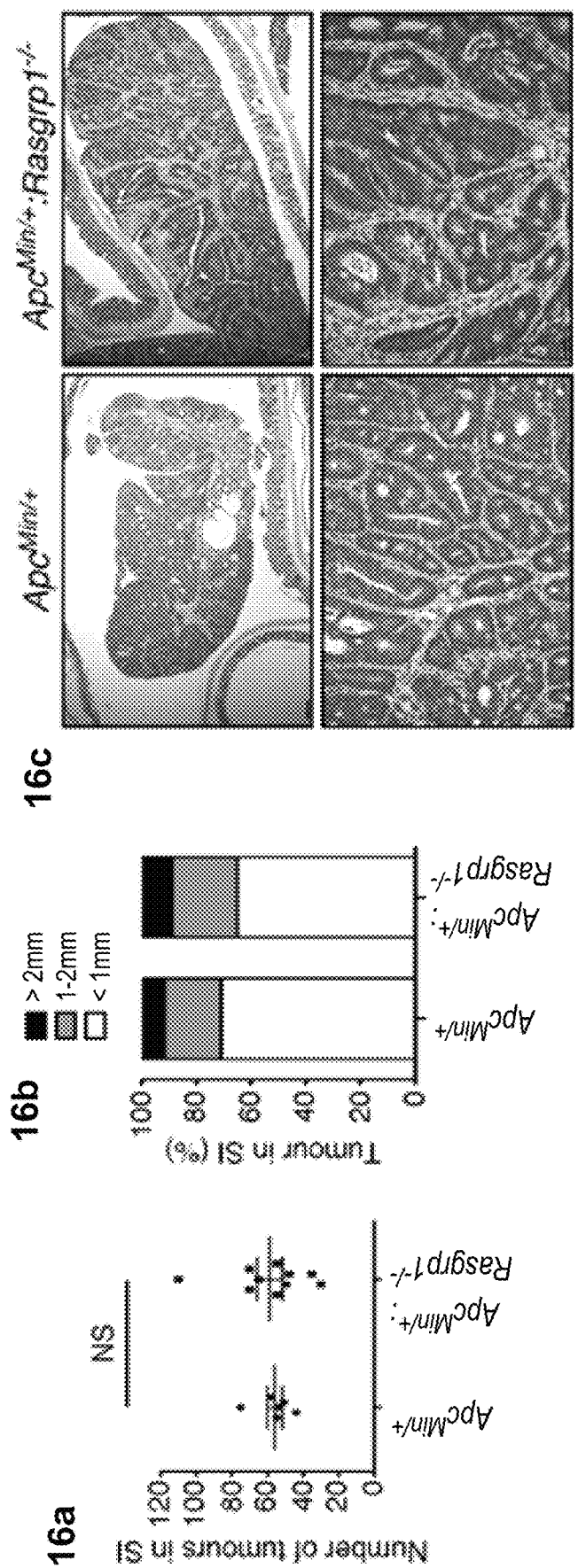
FIGS. 16a-16k show that RasGRP1 suppresses proliferative ERK signaling in the context of aberrant Wnt signaling. $Apc^{Min/+}$ mice develop large numbers of tumors in the small intestine (FIG. 16a) and additional loss of Rasgrp1 did not lead to significant changes in tumor numbers or size in the small intestine (FIGS. 16a and 16b).
Figures 16D, 16E, 16F, 16G, 16H, 16I:
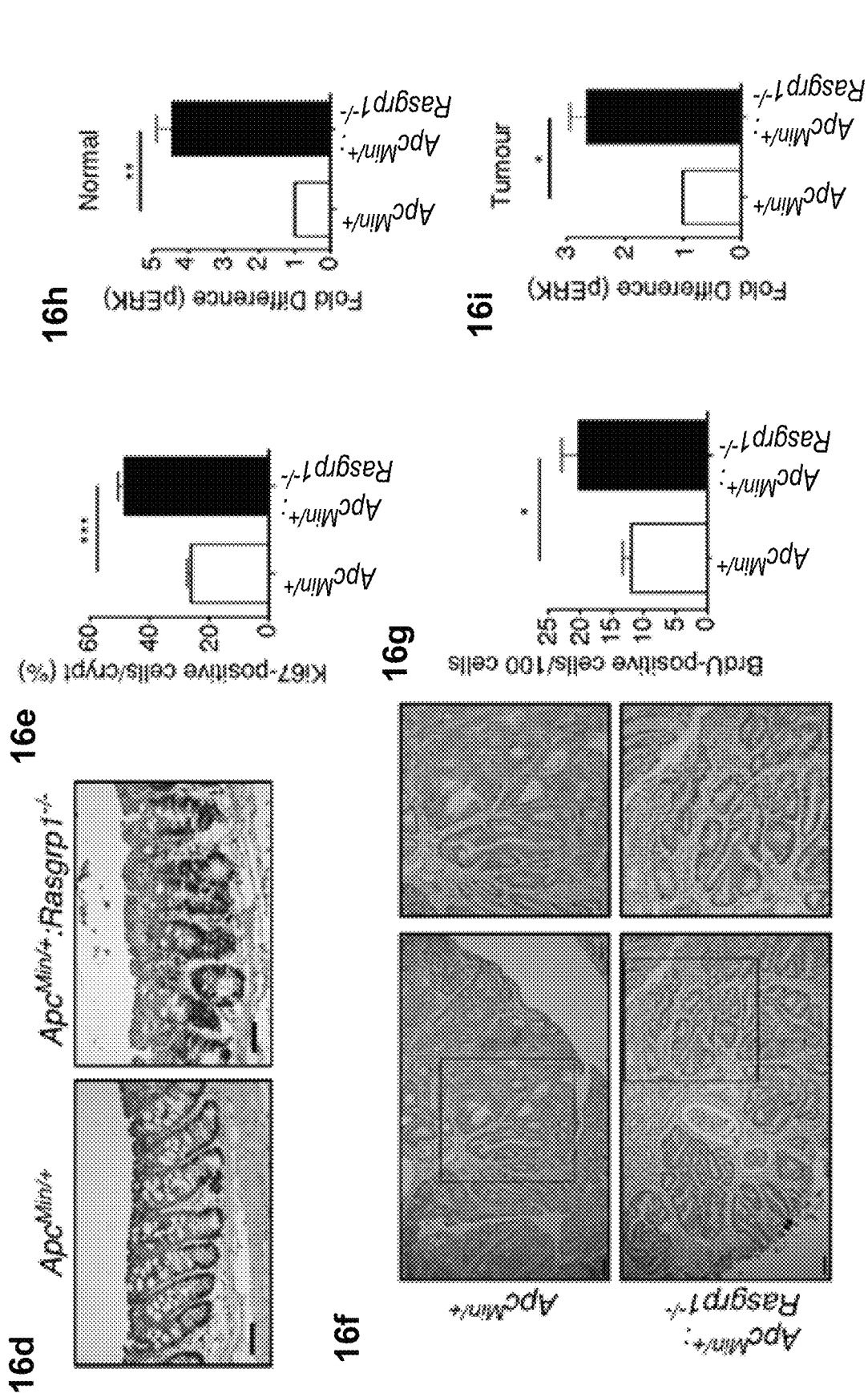
Figures 16J, 16K:
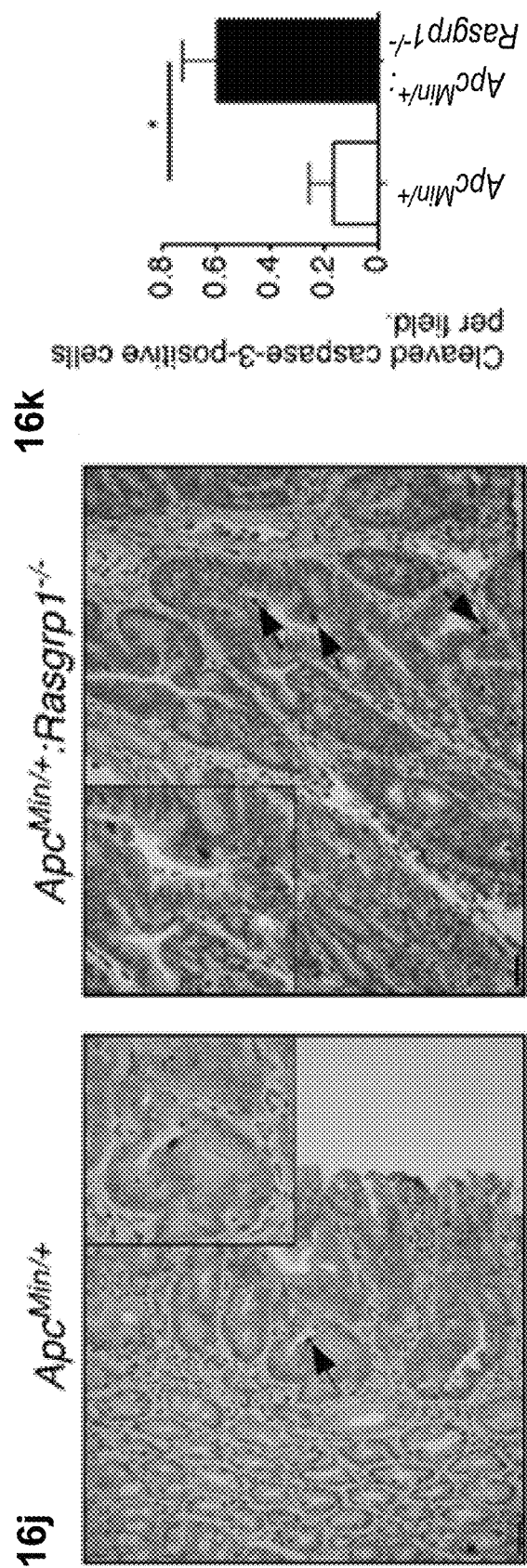

We crossed ApcMin/+ mice to our Rasgrp1 deficient mouse and observed that the mean survival period of 164 days for ApcMin/+ mice reduced to 126 days when ApcMin/+ mice were also deficient for Rasgrp1 (FIG. 8f). As reported[55-57], we found that ApcMin/+ mice develop large numbers of tumors in the small intestine and additional loss of Rasgrp1 did not lead to significant changes in tumor numbers or size in the small intestine (FIGS. 16a and 16b). By contrast, deletion of Rasgrp1 led to a significant increase in the number of colonic tumors that rarely develop in ApcMin/+ mice (FIGS. 8g and 8h). The more frequent colonic tumors in ApcMin/+:Rasgrp1−/− mice demonstrated a similar overall architecture compared to the colonic tumors from ApcMin/+ mice (FIG. 16c) but displayed increased individual tumor size (FIG. 8i). In agreement with these findings, normal crypts and tumors of ApcMin/+:Rasgrp1−/− mice revealed increases in proliferative markers compared to ApcMin/+ mice (FIGS. 16d and 16e). Moreover, loss of Rasgrp1 resulted in significant increases in phopho-ERK signals in both the normal tissue (crypts) and in tumors in the context of ApcMin/+ (FIGS. 8i and 16f). Cleaved caspase-3-positive, apoptotic cells were rare in ApcMin/+ tumors and remained sparse, tough slightly increased, in the tumors from ApcMin/+:Rasgrp1−/− mice (FIGS. 16g and 16h). Thus, RasGRP1 plays a suppressive role in CRC in the context of both KRASMUT and ApcMin/+ by limiting proliferative ERK signals.

Discussion

RasGRP1 as a Suppressor of CRC

Here we revealed that RasGRP1 and SOS1, two structurally distinct RasGEFs[9, 25], both lie downstream of the EGFR. We show that RasGRP1 and SOS1 play opposing roles in the same CRC cell downstream of the EGFR. Biochemically, reduction of RasGRP1 levels relieves the negative feedback to EGFR-SOS1, sustains EGFR-RAS-ERK signalling, and promotes cell proliferation. We find that RasGRP1 plays a negative regulatory role in CRC and that depletion of one or two Rasgrp1 alleles exacerbates ERK signalling and serrated dysplasia and hyperproliferation of the KRas$^{G12D}$ intestinal epithelium. Similarly, Rasgrp1 suppressed ERK signalling and proliferation in the Apc$^{Min/+}$ model of aberrant Wnt signalling. Considering these results and taking a clinical point of view, it is of interest to note that RasGRP1 reveals a range of expression in tumors of CRC patients and that high expression of RasGRP1 correlates with better clinical outcome.

KRAS$^{G12D}$ alone does not lead to full CRC in mice[39-41]. Consistent with the conclusion that perturbed Ras function by itself is insufficient to produce CRC, we did not observe high-grade dysplasia or adenocarcinomas in KRAS$^{G12D}$: Rasgrp1$^{WT/-}$ and KRAS$^{G12D}$:Rasgrp1$^{-/-}$ mice that were up to 9 months of age (not shown). Epithelial cells in these two models return to the normal simple columnar pattern further up the villus, despite the severely altered T/A zone, and loss of Rasgrp1 results in increased levels of cell apoptosis. In order for full CRC to develop in mice, KRAS$^{G12D}$ requires additional events such as loss of the APC (Adenomatous Polyposis Coli) tumor suppressor[40]. Vice versa, perturbation of APC requires EGFR signaling for tumor maintenance[58, 59]. In agreement with the concept that these two pathways intersect in CRC, we observe that loss of Rasgrp1 in addition to the Apc$^{Min/+}$ allele leads to increases in colonic tumor numbers and sizes and reduced mean survival of Apc$^{Min/+}$:Rasgrp1$^{-/-}$ mice.

EGFR Signalling in T/a Cells and the Balance Between Proliferation and Differentiation Our studies reveal that Rasgrp1 also impacts homeostasis of the normal intestinal epithelium. Deletion of Rasgrp1 results in increased proliferation of epithelial cells, increases levels of apoptosis at the tip of the villi, and a modest increase in the numbers of goblet cells. T/A progenitors derive from stem cells in the underlying crypt and produce the epithelial lining in the intestine. It is poorly understood how progenitor cells balance proliferation and terminal differentiation and whether distinct EGFR-Ras signals play a role herein. Deletion of Lrig1, a negative regulator of EGFR signalling, leads to loss of normal intestinal stem cell homeostasis[37]. RasGRP1 and SOS1 have unique roles at distinct stages of T cell development[5-8, 28]. RasGRP1, but not SOS1, has been implicated in several cancer types[32, 60, 61], whereas a recent role for SOS1 in embryonic stem lineage commitment was described[62]. The possibility that RasGRP1 and SOS1 may play opposing roles in the same T/A cell downstream of the same EGFR is a novel and intriguing concept that requires future research.

RasGRP RasGEFs Downstream of Growth Factor Receptors

RasGRP3 appears to connect to cMET(HGF)-signal input[63]. Our results here show that RasGRP1 responds to EGFR signal input. Thus, RasGRP RasGEFs can couple to receptor tyrosine kinases but the mechanistic details and the biological consequences are not yet fully understood. RasGRP3 has been implicated to promote growth of melanoma- and prostate-cancer cells[63, 64] whereas our findings here demonstrate that RasGRP1 opposes the growth of CRC. The suppressive function of RasGRP1 in CRC also contrasts its growth-promoting role in T cell leukaemia[32] and in skin cancer[61]. Thus, not all RasGRP1-generated Ras signals are the same. Similarly, different Ras signals in genetic mouse models have been known to evoke opposing cell biological responses[65-67] and different intensity of EGFR stimuli can impact PC12 cell fate[2]. We propose that RasGRP1 may function as a context-dependent tumor suppressor protein or a protein with oncogenic functions.

Negative Feedback Mechanisms in Cancer Cells with Aberrant Ras Signalling

Here we revealed non-intuitive feedback between two RasGEFs; i.e., EGFR-RasGRP1 signals that dampen EGFR-SOS signals. We characterized this feedback in $KRAS^{MUT}$ cells where SOS1 is allosterically activated by the elevated levels of KRAS-GTP[4, 10, 11]. It is of interest to note that somatic $KRAS^{MUT}$ emerge as mediators of acquired resistance to anti-EGFR therapy[68, 69]. Possibly anti-EGFR therapy inhibits the negative feedback coming from EGFR-RasGRP1 signals. Previous studies have shown that Grb2 can impair access of phosphatases to the FGFR[70, 71]. It is possible that RasGRP1 indirectly promotes phosphatase access to the EGFR, reducing Grb2-SOS1-P-$Y_{1068}$-EGFR complexes. Alternatively, EGFR-RasGRP1 may influence the function of phosphatases directly. The phosphatase Cdc25A binds to and dephosphorylates the EGFR[72]. Interestingly, Vemurafenib (PLX4032) treatment of CRC cells with somatic BRAF(V600E) was recently shown to relieve a negative feedback loop to the EGFR by decreasing the activity of the phosphatase Cdc25C, resulting in increased P-$Y_{1068}$-EGFR levels[73]. Regardless of the exact biochemical nature, the realization that EGFR-RasGRP1 and EGFR-SOS1 signals can elicit opposing cell biological behaviour is a novel concept of relevance to normal intestinal epithelial homeostasis and to CRC.

Methods

Bioinformatics and TCGA Datamining

NCI-60 Cell Lines[31], Cancer Cell Line Encyclopedia[74] and Colorectal Adenocarcinoma[75] databases were evaluated for RasGRP1 mRNA expression and copy levels. We used the online bioinformatics tools, "cBio Cancer Genomics Portal"[30] to interrogate above cancer genomic database (www.cbioportal.org). We analysed RasGRP1 mRNAs expression z-scores correlated with copy number level in NCI-60 Cell Lines, Cancer Cell Line Encyclopedia and TCGA Colorectal Adenocarcinoma, and we computed KRAS mutation association z-score with RasGRP1 mRNA expression[30].

To investigate whether RasGRP1 expression has clinical significance in colon cancer, we compared RasGRP1 gene expression in human colon cancer and normal tissues using the Oncomine database (www.oncomine.org). Statistical analysis of the differences in RasGRP1 expression between these tissues used Oncomine standard algorithms: for each microarray, data were log 2-transformed, median-centered, and standard deviation normalized[76]. The Cancer Genome Atlas (TCGA) dataset obtained from Oncomine are embedded in the TCGA database (at the website address: tcga-data.nci.nih.gov/tcga/)

To validate the correlation for RasGRP1 expression and patient outcome, three public colon cancer datasets (GSE17536[50]; GSE12945[51]; GSE14333[52]) were downloaded from the NCBI GEO database (National Center for Biotechnology Information, Gene Expression Omnibus). Data were normalized using the Robust Multichip Average (RMA) and annotated in GEO[77]. A cut-off finder using the R statistical engine was performed to defining two groups of patients with different survival curves using RasGRP1 gene expression (low or high)[53]. We analysed data at follow-up time of ten years because the number of samples with longer follow-up was too small. The Kaplan-Meier estimator was used to evaluate patients' prognostic. The log-rank (Mantel-Cox) test was carrying out to compare survival curves and to measure Hazard ratios. Analyses were performed and graphs were generated using GraphPad Prism version 6.04.

Cell Lines and Reagents

Cell lines were cultured in ATCC-recommended media at 37° C. in 5% $CO_2$. Stable cell lines infected with lentivirus containing small hairpin RNA (shRNA) against SOS1 or RasGRP1 were selected with puromycin 10 µg/ml (Mediatech, inc, Cellgro) and subsequently sorted for GFP levels. Cells were maintained under selection. Colorectal cancer cell line mutational status was obtained from the Wellcome Trust Sanger Institute Cancer Genome Project Web site (www.sanger.ac.uk/genetics/CGP/) and verified by UCSF sequencing core facility (Supplementary Table 1). BrdU, DAPI, and Alcian blue were purchased from Sigma-Aldrich, Diacylglycerol kinase inhibitor II (R59949) was purchased from Enzo Life Science (Alexis) and dissolved in DMSO, human Epithelial Growth Factor (hEGF) recombinant protein was purchased from Life Technologies and dissolved in PBS, PKC inhibitor Rottlerin was purchased from Calbiochem and dissolved in DMSO.

Antibodies

Antibodies were obtained from the following sources and used at indicated concentration: SOS1 (1:1000 for western blot; 1:100 for immunoprecipitation) from BD Bioscience; α-tubulin (1:2000) from Sigma Aldrich; anti-Ras (1:1000) from Millipore; Grb2, KRas, NRas and HRas (1:200) from Santa Cruz biotechnology; Epithelium Growth Factor Receptor (EGFR), phospho-EGFR (Y-1068), phospho-EGFR (Y-1045), phospho-ERK1/2, ERK1/2 (1:1000) and cleaved caspase-3 (Asp175) (1:200) from Cell Signaling Technology; Ki-67 (1:500) from Abcam; anti-BrdU from the developmental Study Hybridoma bank (G3G4, 1:300), murine RasGRP1 (m199) (immunoprecipitation 1:50) from Jim Stone (University of Alberta, Edmonton, AB, Canada); human RasGRP1 (JR-E160) (1:1000) generated by our laboratory together with Epitomic, phospho-RasGRP1 T184 was generated by immunization with the peptide SRKL-pT-QRIKSNTC by our laboratory and Eurogentech/AnaSpec (Fremont, Calif.).

Mice

All mice were handled according to the Institutional Animal Care and Use Committee regulations, described in the Roose laboratory University of California, San Francisco (UCSF) mouse protocol AN084051 "Ras Signal Transduction in Lymphocytes and Cancer". $KRAS^{LSL-G12D/+}$ mice ($KRAS^{G12D}$, here) previously described were kindly provided by Tyler Jacks (MIT). We crossed these mice to VillinCre transgenic mice provided by Averil Ma (UCSF) to activate the mutant KRAS allele in the intestinal tract. This mouse was used as a control and noted WT. Progenies were then crossed a Rasgrp1 knock-out ($Rasgrp1^{-/-}$) provided by Jim Stone (University of Alberta, Edmonton, AB, Canada) to generate a mouse mice expressing $KRAS^{G12D}$ in the context of 1 and 2 Rasgrp1 alleles deleted $KRAS^{G12D}$:$Rasgrp1^{WT/-}$ and $KRAS^{G12D}$:$Rasgrp1^{-/-}$ respectively. $Apc^{Min/+}$ mice were crossed to $Rasgrp1^{-/-}$ mice to obtained complete deletion of Rasgrp1 ($Apc^{Min/+}$:$Rasgrp1^{-/-}$). Primers used for genotyping of Rasgrp1: Primer 1, GCAGCT-GTCAATAAGATCATCCAGGC (SEQ ID NO: 1); primer 2, ATATTGCTGAAGAGCTTGGCGGCGAATGGG (SEQ ID NO: 2); primer 3, CTATCCTCACTT- GAGTCTCTCTTTCC (SEQ ID NO: 3). All other primers were recommended by Jackson laboratory (Bar Harbor, Me.).

shRNA Constructs and Experiments

Knockdown of human RasGRP1 and human SOS1 has been described previously in Roose et al. (MCB, 2007). Briefly, oligonucleotides containing Hap I and Xho I sites were annealed and ligated into Hap 1- and Xho I-digested pSicoR-puro-t2a-eGFP to create mRasgrp1-1503-pSicoR-puro-t2a-eGFP and hRasGRP1-1503-pSicoR-puro-t2a-eGFP. The oligonucleotide sequences are as follows. For mRasgrp1-1503: sense oligonucleotide, 5'-TGATCGCTG-CAAGC-TTTCCATTCAAGAGATGGAAAGCTTGCA-GCGATCTTTTTTC-3' (SEQ ID NO: 4); antisense oligo-nucleotide, 5'-TCGAGAAAAAAGATCGCTGCAAGCTT-TCCATCTCTTGAATGGAAAGCTTGCAGCGATCA-3' (SEQ ID NO: 5). For hRasGRP1-1503: sense oligonucle-otide, 5'-TGATT-GCTGCG-AGT-TTTCCATTCA-AGA-GATGGAAAACTCGCAGCAATCTTTTTTC-3' (SEQ ID NO: 6); antisense oligo-nucleotide, 5'-TCGA-GAAAAAAGATTGCTGCGAGTTTTCCATCTC-TT-GAATGGAAAACTCGCAGCAATCA-3' (SEQ ID NO: 7). Targeting of the 1503 region was based on previous work (Roose et al.[11]). The hRasGRP1-1503 targets human Ras-GRP1, has three mismatches with the same sequence in mRasgrp1-1503, and served as a specificity control. Briefly, CRC cell lines were seeded in 24-well plate. Cells were infected with lentivirus (SMOI) and polybrene through standard spin infections (2200 rpm for 1 hour) and selected by culture in the presence of puromycin (10 µg/ml) 48h after infection. Similarly, annealed oligonucleotides were ligated into pSicoR-puro-t2a-eGFP to create mSos1-1313-pSicoR-puro-t2a-eGFP and hSOS1-1313-pSicoR-puro-t2a-eGFP, based on published targeting sequences (Roose et al. (MCB, 2007)). hSOS1-1313 targets human SOS1, has two mis-matches with the same sequence in mSos1-1313, and served as a specificity control. For mSos1-1313: sense oligonucle-otide, 5'-TGACAGTGTTGCAA-TGAGTTTTCAAGA-GAAACTCATTGCAACACTGTCTTTTTC-3' (SEQ ID NO: 8); antisense oligonucleotide, 5'-TCGA-GAAAAAAGACAGTGTTGCAAT-GAGTTTCTCTT-GAAAACTCATTGCAACACTGTCA-3' (SEQ ID NO: 9). For hSOS1-1313: sense oligonucleotide, 5'-TGACAGTGT-TGT-AATGAA-TTTTCAAGA-GAAATTCATTA-CAACACTGTCTTTTTTC-3' (SEQ ID NO: 10); antisense oligonucleotide, 5'-TCGAGAAAAAGACAGTGTTG-TAATGAATTTCTCTTGA-AAATTCATTACAACACT-GTCA-3' (SEQ ID NO: 11).

RNA Extraction and Real Time PCR

Total RNA was isolated from human tissue and cell lines using RNeasy kit (Qiagen) following the manufacturer's protocol. RNA was reverse-transcribed with random primers (Invitrogen) and Moloney murine leukaemia virus reverse transcriptase. Real-time PCR was performed in triplicate using Eppendorf RealPlex2. Gene expression was normal-ized to that of GAPDH and quantified with the comparative CT method according to the manufacturer's instructions. The following combinations of primers and probes were used to analyse the expression of human RasGRP1: forward, AAGCTCCACCAACTACAGAACT (SEQ ID NO: 12); reverse, AGGGAGATGAGGTCCTTGAGAT (SEQ ID NO: 13); probe, FAM-CCACATGAAATCAATAAGGTTCTCG-GTGAG-TAMRA (SEQ ID NO: 14) and human GAPDH forward, GAAGGTGAAGGTCGGAGT (SEQ ID NO: 15); reverse, GAAGATGGTGATGGGATTTC (SEQ ID NO: 16); probe, FAM-AGGCTGAGAACGGGAAGCTTGT-TAMRA (SEQ ID NO: 17). RasGRP2, 3 and 4 probes and primers were obtained at Applied Bio System.

Western Blot

Cells were plated in 6 or 10 cm dishes and starved for 2 h at 37 C in PBS. After resting, cells were EGF-stimulated for different time 3, 10 or 30 min. Cells were lysed with ice-cold 2% NP40 supplemented with protease and phos-phatase inhibitors [10 mM sodium fluoride, 2 mM sodium orthovanadate, 0.5 mM EDTA, 2 mM phenyl-methylsulfo-nyl fluoride, 1 mM sodium molybdate, aprotonin (10 mg/ml), leupeptin (10 mg/ml), pepstatin (1 mg/ml)]. After 30 min on ice, lysates were centrifuged and supernatant were mix with 2× sample buffer. Protein lysates were separated on acrylamide gel 10%, transferred on PVDF membrane and incubated with primary antibodies of interest. Inhibitors such as Rottlerin (20 µM) and DGK were pre-incubated for 30 min before stimulation. Western blots were visualized with enhanced chemo-luminescence and imaging on a Fuji LAS 4000 image station (GE Healthcare). The protein bands in Western blots were quantified with Multi Gauge software, and densitometry (pixel intensity) was determined within the linear range of the exposure. Amounts of the proteins of interest were typically presented as a ratio of the indicated loading control. Values were then normalized to an indicated sample and noted as a fold difference. Results represent at least three independent experiments.

Ras Pull Down Assay

Activation of Ras was analysed by a Ras-GTP pull-down assay essentially according to the manufacturer's instruc-tions (Upstate). Briefly, cells were rested with PBS with Ca/Mg in 6-well plates at 37° C. for 2 hours and stimulated with 5 ng/ml hEGF for 3 and 10 min. Cells were then lyse with ice-cold 1×MLB for pull downs (Millipore) and scraped. 20% of the lysate was used for whole cell lysate and 80% was used for pull down. MLB lysates were tumbled in the cold room with RAF-1 RBD agarose for 50 min, washed 3 times in ice-cold 1% NP40 buffer after which the agarose was resuspended in sample buffer, boiled. Lysates were loaded on precast bis-tris gel 4-12% (Invitrogen) and trans-fer on PVDF membrane for blocking. Membranes were incubated with primary antibody and specific signals have been quantified has described in Western blot paragraph. Results represent at least three independent experiments.

Immunoprecipitation

Cells were grown in 10 cm dishes and starved for 2 h at 37 C in PBS. After resting, cells were EGF (5 ng/ml or 25 ng/ml) stimulated for 3, 10 or 30 min and lysed in 1% NP40 has already described above. Supernatant has been spited in 2 parts. 20% used for whole cell lysates and 80% was incubated with anti-human SOS1 and tumbled for 2 h at 4 C. The G-sepharose beads (GE Healthcare) were added and tumbled for 50 min at 4° C. After several washes using 1% NP40, sample buffer was added before being boiled and loaded on acrylamide gels 8% and 10%. Results represent at least three independent experiments.

Isolation of Intestinal Epithelial Cells

Methods were adapted from Sato and colleague[78]. In short, large intestines were dissected, rinsed with PBS, opened and cut in 1-2 cm fragments before incubation in a conical tube with PBS. Debris was removed by PBS washes and fragments were transferred to clean tubes containing pre-warmed PBS with 2.5 mM EDTA. 15-minute incuba-tions at 37° C. water bath and removal of supernatant containing epithelial cells at crypt structures were repeated 2-3 times and cells were collected by centrifugation at 1200 rpm and cells were lysed in NP40 lysis buffer to extract proteins.

Extraction of Colonic Epithelium and Tumors

Colon of mice were dissected and washed with PBS. Tumors were isolated and flash-frozen. Healthy tissues adjacent to tumors were collected to serve as controls. Tissues were incubated in 200 ul of 1×RIPA buffer on ice and homogenized using electric dounce. Lysates were process as described elsewhere. Protein quantification was evaluated using BCA assay (Thermo Scientific).

Soft Agar Colony Formation Assay

Colorectal cell lines were seeded ($1 \cdot 10^5$) in duplicate into 60-mm cell culture dishes in 1 ml of 0.3% agar (Noble agar, SIGMA) in RPMI containing 5% FBS, 1% penicillin/streptomycin, 1% glutamine, and 2.37 g/L $Na_2CO_3$, on top of a layer of 1 ml of 1% agar. For complete culture condition, normal culture media has been added and changed every other day. Cultures were maintained for 15 days. For EGF condition, hEGF (10 ng/ml) has been added to minimal culture media. Colonies were fixed with 70% ethanol and stained with 0.005% crystal violet. Colonies were visualized, and at least 5 randomly chosen fields were photographed with a digital camera Nikon DXM1200 coupled to a light microscope. Results are combination of three-independent experiments.

Xenograft Mouse Studies

HCT15 Cell line with or without shRNA ($2 \times 10^5$) were injected subcutaneously into flank of 6- to 8-weeks-old male Nude-Foxn1nu mice (n=5 at least per group) (Harlan lab). Tumor volume was determined by external calliper measurement every other day as soon as it reached a palpable size. Calculation has been done as follows: tumor volume=½ (length×width$^2$). Mice were monitored daily for body weight and general condition. According to institutional guidelines, mice were sacrificed when their tumor volume reached 2,000 mm$^3$ or became excessively ulcerated. Experiments were repeated twice with 5 mice in each group.

Dextran Sodium Sulfate-Induced Colitis

DSS (3%, MP Biomedicals) was added to the drinking water of co-housed, 10-12 week old C57B16 and Rasgrp1$^{-/-}$ mice for 5 days. Mice were assessed daily for diarrhea, bloody stool and body weight. At day 5, mice were euthanized and small and large intestine were processed as described in "immunohistochemistry" section. DSS damage scores were determined by the sum of three parameters as previously described[79]: surface epithelial loss, crypt destruction, and inflammatory cell infiltration into the mucosa. A score of "0" represents no change, "1" localized and mild change, "2" localized and moderate change, "3" extensive and moderate change, "4" extensive and severe change.

Immunohistochemistry

Tissues were dissected, fixed in 4% PFA and paraffin-embedded. Then 5-μm-thick sections were de-waxed in Histo-Clear (National Diagnostics) and rehydrated in graded alcohol baths. Antigen retrieval was performed in pressure cooker for 20 min in 10 mM sodium citrate buffer, pH 6.0. Endogenous peroxidase activity was inhibited with 1.5% $H_2O_2$ in methanol for 20 min and washed in PBS. Nonspecific binding sites were blocked in blocking buffer (PBS, pH 7.4, 3% Serum, 1% BSA, and 0.1% Tween) for 60 min at RT. Sections were then incubated with primary antibodies diluted in blocking buffer overnight at 4° C. Slides were then washed twice with 0.1% PBS-Tween before incubation in Universal Immuno-peroxydase polymer anti-mouse/rabbit Histofine® for mouse tissues (Nichirei Biosciences, Japan) used as a secondary reagent. Stainings were visualized with DAB (3, 3'-diaminobenzidine, Sigma-Aldrich) and a hematoxylin counterstain (Sigma-Aldrich) was performed before dehydratation. After dehydration, sections were mounted in Cytoseal 60 (Thermo Scientific). To study the structure of tissue, Haematoxylin & Eosin (H&E) was performed. For quantification, images were acquired using a Nikon Optiphot microscope equipped with an AxioCam HR a fixed exposure (objective 20× and 40×). For BrdU experiments, mice were injected intraperitoneally (2 mg/200 μl) for 2 hours or 48 hours. To detect goblet cells, slides were treated with Alcian blue (pH2.5) for 30 min. and counterstained using Nuclear Red (Sigma-Aldrich) followed by standard mounting techniques.

Immunofluorescence

Tissues were dissected, fixed in 4% PFA, incubated overnight at 4 C in Sucrose 30% and embedded in OCT (Tissue-Tek, Dublin, Ireland)/Sucrose 30% (2 vol/1 vol). 10 μm-thick sections (Cryostat Leica) were dried and wash in PBS. After 0.1% PBS-Tween (Sigma-Aldrich) wash, section were incubated in blocking buffer (1% BSA, 3% normal goat serum and 0.2% Triton X-100-PBS) for 1 h at RT. Sections were then incubated with primary antibodies diluted in blocking buffer overnight at 4° C. Slides were washed twice with 0.1% PBS-Tween and PBS before incubation in secondary antibody conjugated with Alexa 546 (Molecular Probes, Life technologies) and DAPI in PBS-Triton X-100 0.5% (Sigma-Aldrich) for 45 min at RT. Slides were washed twice with PBS before mounting with mounting medium (Dako). Images were taken by using a microlensed, spinning disk confocal scan-head coupled to a motorized, inverted fluorescence microscope (Zeiss Axiovert 200M; Carl Zeiss Inc.). Images were collected using an ICCD camera (XR-Mega-10EX S-30, Stanford Photonics, Palo Alto, Calif.).

Positioning of In Vivo BrdU Labelled Cells

Mice were injected with BrdU as described before and euthanized 48 hours post-injection. Swiss roll gut preparations were produced, stained and fixed as described above. BrdU-positive cells from twenty crypt-villus axes in duodenum were analysed per mouse. Cells were counted from bottom (position 1) of open crypts (transversally sectioned) to the top of villi. Percentage of cells per position was representative of two mice per genotype. Counting method was adapted from Sansom and colleagues[54].

Quantification and Statistical Analysis

In short-term BrdU experiments at 2 hours after injection, fifty crypts were counted per mouse (n=3). For cleaved caspase-3 experiments (IF), 50 open villi per genotype were counted (n=3). Results were combined for each genotype. For branching villi, a total fifty villi per mouse (n=4) were counted in different area of the duodenum. Results are average of number of branched villi for ten villi counted. For goblet cells in intestine, fifty open villi (transversally sectioned) in duodenum per mouse were counted; two mice per genotype. For goblet cells and Ki67-positive cells in colon, fifty crypts in distal colon were counted with 3 mice per genotype. For cleaved caspase-3 and BrdU in tumors, numbers of positive cells were evaluated per field (100 μm×100 μm) with 3 to 6 fields taken per tumor (n=3 mice per genotype). Results were combined for each genotype. For the Kaplan-Meier survival curve of the Apc$^{Min/+}$ mice, a Log-rank (Mantel-Cox) test was applied. For villi lengths, pictures were taken and length of villi in duodenum was determined using Image J software. Pixel values were transformed in metric values using microscope scale. Fifty villi were counted and values are representative of three mice per genotype.

All data were represented as mean±SEM. For xenograft experiments, damage score after DSS treatment, and immunostainings, unpaired t test were used for two-group comparisons. For comparisons of phospho-ERK immunoblot quantification, a paired t test was applied. All specific statistical analyses are mentioned in the respective paragraphs. All other experiments a one-way ANOVA followed by a Bonferroni post hoc test was used for comparisons of three or more groups. For all tests, a P value of <0.05 was considered statistically significant. Analyses and graphs were done using Prism 5 software.

REFERENCES

1. Vigil, D., Cherfils, J., Rossman, K. L. & Der, C. J. Ras superfamily GEFs and GAPs: validated and tractable targets for cancer therapy? Nat Rev Cancer 10, 842-857 (2010).
2. Marshall, C. J. Specificity of receptor tyrosine kinase signaling: transient versus sustained extracellular signal-regulated kinase activation. Cell 80, 179-185 (1995).
3. Prasad, A. et al. Origin of the sharp boundary that discriminates positive and negative selection of thymocytes. Proc Natl Acad Sci USA 106, 528-533 (2009).
4. Das, J. et al. Digital signaling and hysteresis characterize ras activation in lymphoid cells. Cell 136, 337-351 (2009).
5. Ksionda, O., Limnander, A., Roose, J. Rasgrp Ras Guanine Nucleotide Exchange Factors in Cancer. Frontiers in Biology 8, 508-532 (2013).
6. Kortum, R. L. et al. Targeted Sos1 deletion reveals its critical role in early T-cell development. Proc Natl Acad Sci USA 108, 12407-12412 (2011).
7. Kortum, R. L., Rouquette-Jazdanian, A. K. & Samelson, L. E. Ras and extracellular signal-regulated kinase signaling in thymocytes and T cells. Trends Immunol (2013).
8. Dower, N. A. et al. RasGRP is essential for mouse thymocyte differentiation and TCR signaling. Nat Immunol 1, 317-321 (2000).
9. Margarit, S. M. et al. Structural evidence for feedback activation by Ras.GTP of the Ras-specific nucleotide exchange factor SOS. Cell 112, 685-695 (2003).
10. Boykevisch, S. et al. Regulation of ras signaling dynamics by Sos-mediated positive feedback. Current biology: CB 16, 2173-2179 (2006).
11. Roose, J. P., Mollenauer, M., Ho, M., Kurosaki, T. & Weiss, A. Unusual interplay of two types of Ras activators, RasGRP and SOS, establishes sensitive and robust Ras activation in lymphocytes. Mol Cell Biol 27, 2732-2745 (2007).
12. Bos, J. L., Rehmann, H. & Wittinghofer, A. GEFs and GAPs: critical elements in the control of small G proteins. Cell 129, 865-877 (2007).
13. Malumbres, M. & Barbacid, M. RAS oncogenes: the first 30 years. Nat Rev Cancer 3, 459-465 (2003).
14. Jemal, A. et al. Cancer statistics, 2009. CA Cancer J Clin 59, 225-249 (2009).
15. Di Fiore, F., Sesboue, R., Michel, P., Sabourin, J. C. & Frebourg, T. Molecular determinants of anti-EGFR sensitivity and resistance in metastatic colorectal cancer. Br J Cancer 103, 1765-1772 (2010).
16. Chandarlapaty, S. Negative feedback and adaptive resistance to the targeted therapy of cancer. Cancer Discov 2, 311-319 (2012).
17. Pratilas, C. A. & Solit, D. B. Targeting the mitogen-activated protein kinase pathway: physiological feedback and drug response. Clin Cancer Res 16, 3329-3334 (2010).
18. Normanno, N. et al. Implications for KRAS status and EGFR-targeted therapies in metastatic CRC. Nat Rev Clin Oncol 6, 519-527 (2009).
19. Wheeler, D. L., Dunn, E. F. & Harari, P. M. Understanding resistance to EGFR inhibitors-impact on future treatment strategies. Nat Rev Clin Oncol 7, 493-507 (2010).
20. Ardito, C. M. et al. EGF receptor is required for KRAS-induced pancreatic tumorigenesis. Cancer cell 22, 304-317 (2012).
21. Navas, C. et al. EGF receptor signaling is essential for k-ras oncogene-driven pancreatic ductal adenocarcinoma. Cancer cell 22, 318-330.
22. Moore, M. J. et al. Erlotinib plus gemcitabine compared with gemcitabine alone in patients with advanced pancreatic cancer: a phase III trial of the National Cancer Institute of Canada Clinical Trials Group. J Clin Oncol 25, 1960-1966 (2007).
23. Threadgill, D. W. et al. Targeted disruption of mouse EGF receptor: effect of genetic background on mutant phenotype. Science 269, 230-234 (1995).
24. Aliaga, J. C., Deschenes, C., Beaulieu, J. F., Calvo, E. L. & Rivard, N. Requirement of the MAP kinase cascade for cell cycle progression and differentiation of human intestinal cells. The American journal of physiology 277, G631-641 (1999).
25. Iwig, J. S. et al. Structural analysis of autoinhibition in the Ras-specific exchange factor RasGRP1. eLife 2, e00813 (2013).
26. Noffsinger, A. E. Serrated polyps and colorectal cancer: new pathway to malignancy. Annual review of pathology 4, 343-364 (2009).
27. Oh-hora, M., Johmura, S., Hashimoto, A., Hikida, M. & Kurosaki, T. Requirement for Ras guanine nucleotide releasing protein 3 in coupling phospholipase C-gamma2 to Ras in B cell receptor signaling. J Exp Med 198, 1841-1851 (2003).
28. Jun, J. E., Rubio, I. & Roose, J. P. Regulation of Ras Exchange Factors and Cellular Localization of Ras Activation by Lipid Messengers in T Cells. Frontiers in immunology 4, 239 (2013).
29. Ebinu, J. O. et al. RasGRP, a Ras guanyl nucleotide-releasing protein with calcium- and diacylglycerol-binding motifs. Science 280, 1082-1086 (1998).
30. Cerami, E. et al. The cBio cancer genomics portal: an open platform for exploring multidimensional cancer genomics data. Cancer Discov 2, 401-404 (2012).
31. Reinhold, W. C. et al. CellMiner: a web-based suite of genomic and pharmacologic tools to explore transcript and drug patterns in the NCI-60 cell line set. Cancer Res 72, 3499-3511 (2012).
32. Hartzell, C. et al. Dysregulated RasGRP1 Responds to Cytokine Receptor Input in T Cell Leukemogenesis. Science signaling 6, ra21 (2013).
33. van der Flier, L. G. & Clevers, H. Stem cells, self-renewal, and differentiation in the intestinal epithelium. Annual review of physiology 71, 241-260 (2009).
34. Krausova, M. & Korinek, V. Wnt signaling in adult intestinal stem cells and cancer. Cell Signal 26, 570-579 (2014).
35. Biteau, B. & Jasper, H. EGF signaling regulates the proliferation of intestinal stem cells in *Drosophila*. Development 138, 1045-1055 (2011).
36. Jiang, H., Grenley, M. O., Bravo, M. J., Blumhagen, R. Z. & Edgar, B. A. EGFR/Ras/MAPK signaling mediates adult midgut epithelial homeostasis and regeneration in *Drosophila*. Cell stem cell 8, 84-95 (2011).

37. Wong, V. W. et al. Lrig1 controls intestinal stem-cell homeostasis by negative regulation of ErbB signalling. Nat Cell Biol 14, 401-408 (2012).
38. Dieleman, L. A. et al. Dextran sulfate sodium-induced colitis occurs in severe combined immunodeficient mice. Gastroenterology 107, 1643-1652 (1994).
39. Feng, Y. et al. Mutant KRAS promotes hyperplasia and alters differentiation in the colon epithelium but does not expand the presumptive stem cell pool. Gastroenterology 141, 1003-1013 e1001-1010 (2011).
40. Haigis, K. M. et al. Differential effects of oncogenic K-Ras and N-Ras on proliferation, differentiation and tumor progression in the colon. Nature genetics 40, 600-608 (2008).
41. Bennecke, M. et al. Ink4a/Arf and oncogene-induced senescence prevent tumor progression during alternative colorectal tumorigenesis. Cancer Cell 18, 135-146 (2010).
42. Daley, S. R. et al. Rasgrp1 mutation increases naive T-cell CD44 expression and drives mTOR-dependent accumulation of Helios+ T cells and autoantibodies. eLife 2, e01020 (2013).
43. Buday, L. & Downward, J. Epidermal growth factor regulates p21ras through the formation of a complex of receptor, Grb2 adapter protein, and Sos nucleotide exchange factor. Cell 73, 611-620 (1993).
44. Porfiri, E. & McCormick, F. Regulation of epidermal growth factor receptor signaling by phosphorylation of the ras exchange factor hSOS1. The Journal of biological chemistry 271, 5871-5877 (1996).
45. Baltensperger, K. et al. Binding of the Ras activator son of sevenless to insulin receptor substrate-1 signaling complexes. Science 260, 1950-1952 (1993).
46. Kawasaki, H. et al. A Rap guanine nucleotide exchange factor enriched highly in the basal ganglia. Proceedings of the National Academy of Sciences of the United States of America 95, 13278-13283 (1998).
47. Jeng, H. H., Taylor, L. J. & Bar-Sagi, D. Sos-mediated cross-activation of wild-type Ras by oncogenic Ras is essential for tumorigenesis. Nat Commun 3, 1168 (2012).
48. Downward, J., Parker, P. & Waterfield, M. D. Autophosphorylation sites on the epidermal growth factor receptor. Nature 311, 483-485 (1984).
49. Topham, M. K. & Prescott, S. M. Diacylglycerol kinase zeta regulates Ras activation by a novel mechanism. J Cell Biol 152, 1135-1143 (2001).
50. Smith, J. J. et al. Experimentally derived metastasis gene expression profile predicts recurrence and death in patients with colon cancer. Gastroenterology 138, 958-968 (2010).
51. Staub, E. et al. An expression module of WIPF1-coexpressed genes identifies patients with favorable prognosis in three tumor types. Journal of molecular medicine 87, 633-644 (2009).
52. Jorissen, R. N. et al. Metastasis-Associated Gene Expression Changes Predict Poor Outcomes in Patients with Dukes Stage B and C Colorectal Cancer. Clin Cancer Res 15, 7642-7651 (2009).
53. Budczies, J. et al. Cutoff Finder: a comprehensive and straightforward Web application enabling rapid biomarker cutoff optimization. PloS one 7, e51862 (2012).
54. Sansom, O. J. et al. Loss of Apc in vivo immediately perturbs Wnt signaling, differentiation, and migration. Genes Dev 18, 1385-1390 (2004).
55. Moser, A. R., Pitot, H. C. & Dove, W. F. A dominant mutation that predisposes to multiple intestinal neoplasia in the mouse. Science 247, 322-324 (1990).
56. Su, L. K. et al. Multiple intestinal neoplasia caused by a mutation in the murine homolog of the APC gene. Science 256, 668-670 (1992).
57. Taketo, M. M. & Edelmann, W. Mouse models of colon cancer. Gastroenterology 136, 780-798 (2009).
58. Lee, D. et al. Tumor-specific apoptosis caused by deletion of the ERBB3 pseudo-kinase in mouse intestinal epithelium. J Clin Invest 119, 2702-2713 (2009).
59. Roberts, R. B. et al. Importance of epidermal growth factor receptor signaling in establishment of adenomas and maintenance of carcinomas during intestinal tumorigenesis. Proc Natl Acad Sci USA 99, 1521-1526 (2002).
60. Luke, C. T., Oki-Idouchi, C. E., Cline, J. M. & Lorenzo, P. S. RasGRP1 overexpression in the epidermis of transgenic mice contributes to tumor progression during multistage skin carcinogenesis. Cancer research 67, 10190-10197 (2007).
61. Oki-Idouchi, C. E. & Lorenzo, P. S. Transgenic overexpression of RasGRP1 in mouse epidermis results in spontaneous tumors of the skin. Cancer research 67, 276-280 (2007).
62. Findlay, G. M. et al. Interaction domains of sos1/grb2 are finely tuned for cooperative control of embryonic stem cell fate. Cell 152, 1008-1020 (2013).
63. Yang, D. et al. RasGRP3, a Ras activator, contributes to signaling and the tumorigenic phenotype in human melanoma. Oncogene (2011).
64. Yang, D. et al. RasGRP3 contributes to formation and maintenance of the prostate cancer phenotype. Cancer Res 70, 7905-7917 (2010).
65. Diaz, R. et al. The N-ras proto-oncogene can suppress the malignant phenotype in the presence or absence of its oncogene. Cancer Res 62, 4514-4518 (2002).
66. Matallanas, D. et al. Mutant K-Ras activation of the proapoptotic MST2 pathway is antagonized by wild-type K-Ras. Mol Cell 44, 893-906 (2011).
67. To, M. D. et al. Kras regulatory elements and exon 4A determine mutation specificity in lung cancer. Nature genetics 40, 1240-1244 (2008).
68. Diaz, L. A., Jr. et al. The molecular evolution of acquired resistance to targeted EGFR blockade in colorectal cancers. Nature 486, 537-540 (2012).
69. Misale, S. et al. Emergence of KRAS mutations and acquired resistance to anti-EGFR therapy in colorectal cancer. Nature 486, 532-536 (2012).
70. Ahmed, Z. et al. Grb2 controls phosphorylation of FGFR2 by inhibiting receptor kinase and Shp2 phosphatase activity. J Cell Biol 200, 493-504 (2013).
71. Lin, C. C. et al. Inhibition of basal FGF receptor signaling by dimeric Grb2. Cell 149, 1514-1524 (2012).
72. Wang, Z., Wang, M., Lazo, J. S. & Carr, B. I. Identification of epidermal growth factor receptor as a target of Cdc25A protein phosphatase. J Biol Chem 277, 19470-19475 (2002).
73. Prahallad, A. et al. Unresponsiveness of colon cancer to BRAF(V600E) inhibition through feedback activation of EGFR. Nature 483, 100-103 (2012).
74. Barretina, J. et al. The Cancer Cell Line Encyclopedia enables predictive modelling of anticancer drug sensitivity. Nature 483, 603-607 (2012).
75. Network, C. G. A. Comprehensive molecular characterization of human colon and rectal cancer. Nature 487, 330-337 (2012).
76. Rhodes, D. R. et al. ONCOMINE: a cancer microarray database and integrated data-mining platform. Neoplasia 6, 1-6 (2004).

77. Edgar, R., Domrachev, M. & Lash, A. E. Gene Expression Omnibus: NCBI gene expression and hybridization array data repository. Nucleic Acids Res 30, 207-210 (2002).
78. Sato, T. et al. Single Lgr5 stem cells build crypt-villus structures in vitro without a mesenchymal niche. Nature 459, 262-265 (2009).
79. Nishiyama, Y., Kataoka, T., Yamato, K., Taguchi, T. & Yamaoka, K. Suppression of dextran sulfate sodium-induced colitis in mice by radon inhalation. Mediators of inflammation 2012, 239617 (2012).

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

What is claimed is:

1. A method for selecting a drug therapy for a subject with a cancer selected from the group consisting of colorectal cancer, pancreatic cancer, lung cancer and breast cancer, said method comprising the steps of:
    (a) determining the level of RasGRP1 with an assay to detect the level of RasGRP1 in a sample that comprises cancer cells from the subject;
    (b) selecting an anti-EGFR therapy for the subject if the level of RasGRP1 is lower than a threshold value, wherein the anti-EGFR therapy is an agent that selectively inhibits EGFR expression or activity; and
    (c) administering the anti-EGFR therapy to the patient.

2. The method of claim 1, further comprising determining the presence or absence of a KRAS mutation in an equivalent sample obtained from the subject, wherein the KRAS mutation is G12C, G12R, G12S, G12A, G12D, G12V, G13C, G13R, G13S, G13A, G13D, G13V, G34T, G34A, G34C, G35T, G35C, G35A, G37T, G37C, G37A, G48T, G38A, G38A, Q61K, Q61L, Q61R, Q61H, K117N, A146P, A146T or A146V.

3. The method of claim 1, wherein the anti-EGFR therapy is an agent that binds to EGFR and inhibits activation.

4. The method of claim 1, wherein the cancer is colorectal cancer.

5. The method of claim 1, wherein the sample is a tumor biopsy sample.

6. The method of claim 1, wherein the assay to detect the level of RasGRP1 in the sample detects the level of RasGRP1 RNA.

7. The method of claim 6, wherein the assay that detects the level of RasGRP1 RNA comprises an amplification assay or a hybridization assay.

8. The method of claim 1, wherein the assay that detects the level of RasGRP1 detects the level of RasGRP1 polypeptide.

9. The method of claim 1, wherein the anti-EGFR therapy is an EGFR blocking antibody or an EGFR-selective tyrosine kinase inhibitor.

10. The method of claim 8, wherein the assay comprises performing an immunoassay, immunohistochemistry, western blot analysis, or mass spectrometry.

11. The method of claim 7, wherein the amplification assay is a quantitative amplification assay.

12. A method of treating cancer in subject, wherein the subject has a cancer selected from the group consisting of colorectal cancer, pancreatic cancer, lung cancer, and breast cancer, said method comprising the steps of:
    (a) determining that the patient is likely to be responsive to an anti-EGFR therapy by
        obtaining or having obtained a sample comprising cancer cells from the subject; and
        performing or having performed an assay to detect the level of RasGRP1 in the sample; and
    (b) identifying a level of RasGRP1 that is lower than a threshold value, and then administering an agent that binds to EGFR and inhibits activation.

13. The method of claim 12, wherein the cancer is colorectal cancer.

14. The method of claim 12, wherein the sample is a tumor biopsy sample.

15. The method of claim 12, wherein the level of RasGRP1 RNA is determined in the sample.

16. The method of claim 15, wherein the assay to detect the level of RasGRP1 RNA comprises an amplification assay or a hybridization assay.

17. The method of claim 16, wherein the amplification assay is a quantitative amplification assay.

18. The method of claim 17, wherein the level of RasGRP1 polypeptide is determined in the sample.

19. The method of claim 18, wherein determining the level of RasGRP1 polypeptide comprises performing an immunoassay, immunohistochemistry, western blot analysis, or mass spectrometry.

20. The method of claim 12, wherein the anti-EGFR therapy is an EGFR blocking antibody or an EGFR-selective tyrosine kinase inhibitor.

21. A method of treating cancer in subject, wherein the subject has a cancer selected from the group consisting of colorectal cancer, pancreatic cancer, lung cancer, and breast cancer, said method comprising the steps of:
    (a) determining that the patient is likely to be responsive to an anti-EGFR therapy by
        obtaining or having obtained a sample that comprises cancer cells from the subject; and
        performing or having performed an assay to detect the level of RasGRP1 in the sample; and
    (b) if the level of RasGRP1 is lower than a threshold value, then administering an EGFR blocking antibody or an EGFR-selective tyrosine kinase inhibitor; or if the of RasGRP1 is higher than the threshold value, then administering a non-anti-EGFR therapy that binds to and inhibits a BRAF, AKT, MEK, cMET, or VEGFR kinase.

* * * * *

SEQUENCE LISTING

```
<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: synthetic primer

<400> SEQUENCE: 1
gcagctgtca ataagatcat ccaggc                                26

<210> SEQ ID NO 2
<211> LENGTH: 30
<212> TYPE: DNA
<213> ORGANISM: Artificial Sequence
<220> FEATURE:
<223> OTHER INFORMATION: synthetic primer

<400> SEQUENCE: 2
atattgctga agagcttggc ggcgaatggg                            30

<210> SEQ ID NO 3
<211> LENGTH: 26
<212> TYPE: DNA
<213> ORGANISM: Artificial Sequence
<220> FEATURE:
<223> OTHER INFORMATION: synthetic primer

<400> SEQUENCE: 3
ctatcctcac ttgagtctct ctttcc                                26

<210> SEQ ID NO 4
<211> LENGTH: 55
<212> TYPE: DNA
<213> ORGANISM: Artificial Sequence
<220> FEATURE:
<223> OTHER INFORMATION: synthetic sense oligonucleotide

<400> SEQUENCE: 4
tgatcgctgc aagctttcca ttcaagagat ggaaagcttg cagcgatctt ttttc    55

<210> SEQ ID NO 5
<211> LENGTH: 59
<212> TYPE: DNA
<213> ORGANISM: Artificial Sequence
<220> FEATURE:
<223> OTHER INFORMATION: synthetic antisense oligonucleotide

<400> SEQUENCE: 5
tcgagaaaaa agatcgctgc aagctttcca tctcttgaat ggaaagcttg cagcgatca    59

<210> SEQ ID NO 6
<211> LENGTH: 55
<212> TYPE: DNA
```

```
<213> ORGANISM: Artificial Sequence
<220> FEATURE:
<223> OTHER INFORMATION: synthetic sense oligonucleotide

<400> SEQUENCE: 6
tgattgctgc gagttttcca ttcaagagat ggaaaactcg cagcaatctt ttttc       55

<210> SEQ ID NO 7
<211> LENGTH: 59
<212> TYPE: DNA
<213> ORGANISM: Artificial Sequence
<220> FEATURE:
<223> OTHER INFORMATION: synthetic antisense oligonucleotide

<400> SEQUENCE: 7
tcgagaaaaa agattgctgc gagttttcca tctcttgaat ggaaaactcg cagcaatca   59

<210> SEQ ID NO 8
<211> LENGTH: 55
<212> TYPE: DNA
<213> ORGANISM: Artificial Sequence
<220> FEATURE:
<223> OTHER INFORMATION: synthetic sense oligonucleotide

<400> SEQUENCE: 8
tgacagtgtt gcaatgagtt ttcaagagaa actcattgca acactgtctt ttttc       55

<210> SEQ ID NO 9
<211> LENGTH: 59
<212> TYPE: DNA
<213> ORGANISM: Artificial Sequence
<220> FEATURE:
<223> OTHER INFORMATION: synthetic antisense oligonucleotide

<400> SEQUENCE: 9
tcgagaaaaa agacagtgtt gcaatgagtt tctcttgaaa actcattgca acactgtca   59

<210> SEQ ID NO 10
<211> LENGTH: 55
<212> TYPE: DNA
<213> ORGANISM: Artificial Sequence
<220> FEATURE:
<223> OTHER INFORMATION: synthetic sense oligonucleotide

<400> SEQUENCE: 10
tgacagtgtt gtaatgaatt ttcaagagaa attcattaca acactgtctt ttttc       55

<210> SEQ ID NO 11
<211> LENGTH: 59
<212> TYPE: DNA
<213> ORGANISM: Artificial Sequence
<220> FEATURE:
<223> OTHER INFORMATION: synthetic antisense oligonucleotide

<400> SEQUENCE: 11
tcgagaaaaa agacagtgtt gtaatgaatt tctcttgaaa attcattaca acactgtca   59

<210> SEQ ID NO 12
<211> LENGTH: 22
<212> TYPE: DNA
<213> ORGANISM: Artificial Sequence
<220> FEATURE:
<223> OTHER INFORMATION: synthetic primer

<400> SEQUENCE: 12
aagctccacc aactacagaa ct                                           22
```

```
<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
agggagatga ggtccttgag at                                              22

<210> SEQ ID NO 14
<211> LENGTH: 30
<212> TYPE: DNA
<213> ORGANISM: Artificial Sequence
<220> FEATURE:
<223> OTHER INFORMATION: synthetic probe
<220> FEATURE:
<221> NAME/KEY: misc_feature
<222> LOCATION: (1)..(1)
<223> OTHER INFORMATION: 5' end labeled with FAM (6-carboxyfluorescein)
<220> FEATURE:
<221> NAME/KEY: misc_feature
<222> LOCATION: (30)..(30)
<223> OTHER INFORMATION: 3' end labeled with TAMRA
      (tetramethylrhodamine)

<400> SEQUENCE: 14
ccacatgaaa tcaataaggt tctcggtgag                                      30

<210> SEQ ID NO 15
<211> LENGTH: 18
<212> TYPE: DNA
<213> ORGANISM: Artificial Sequence
<220> FEATURE:
<223> OTHER INFORMATION: synthetic primer

<400> SEQUENCE: 15
gaaggtgaag gtcggagt                                                   18

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
gaagatggtg atgggatttc                                                 20

<210> SEQ ID NO 17
<211> LENGTH: 22
<212> TYPE: DNA
<213> ORGANISM: Artificial Sequence
<220> FEATURE:
<223> OTHER INFORMATION: synthetic probe
<220> FEATURE:
<221> NAME/KEY: misc_feature
<222> LOCATION: (1)..(1)
<223> OTHER INFORMATION: 5' end labeled with FAM (6-carboxyfluorescein)
<220> FEATURE:
<221> NAME/KEY: misc_feature
<222> LOCATION: (30)..(30)
<223> OTHER INFORMATION: 3' end labeled with TAMRA
      (tetramethylrhodamine)

<400> SEQUENCE: 17
aggctgagaa cgggaagctt gt                                              22
```